(12) United States Patent
Delfani et al.

(10) Patent No.: US 7,981,863 B2
(45) Date of Patent: Jul. 19, 2011

(54) TREATMENT OF PARKINSON'S DISEASE WITH PDGF

(75) Inventors: Kioumars Delfani, Sundbyberg (SE); Ann Marie Janson, Stockholm (SE); H. Georg Kuhn, Pattendorf (DE); Karlheinz Plate, Frankfurt (DE); Anne Schanzer, Frankfurt am Main (DE); Frank-Peter Wachs, Obertraubling (DE); Ming Zhao, Solna (SE)

(73) Assignee: Neuronova AB, Stockholm (SE)

( * ) Notice: Subject to any disclaimer, the term of this patent is extended or adjusted under 35 U.S.C. 154(b) by 2483 days.

(21) Appl. No.: 10/246,091

(22) Filed: Sep. 18, 2002

(65) Prior Publication Data

US 2003/0203844 A1 Oct. 30, 2003

Related U.S. Application Data

(60) Provisional application No. 60/323,381, filed on Sep. 19, 2001, provisional application No. 60/326,044, filed on Sep. 28, 2001.

(51) Int. Cl.
*A61K 38/00* (2006.01)
*A61K 38/18* (2006.01)
*C12N 5/00* (2006.01)
*C12N 5/079* (2010.01)
*C12N 5/0797* (2010.01)
*C12N 5/0793* (2010.01)
*C07K 14/49* (2006.01)

(52) U.S. Cl. ............ 514/8.2; 514/1.1; 514/1.2; 514/1.3; 514/7.6; 514/17.7; 435/368

(58) Field of Classification Search ........................ None
See application file for complete search history.

(56) References Cited

U.S. PATENT DOCUMENTS

| | | | | |
|---|---|---|---|---|
| 5,116,873 | A | 5/1992 | Gorio et al. | 514/567 |
| 5,219,759 | A | 6/1993 | Heldin et al. | 435/320.1 |
| 5,653,975 | A * | 8/1997 | Baetge et al. | 424/93.1 |
| 5,980,885 | A * | 11/1999 | Weiss et al. | 424/93.21 |
| 6,040,157 | A | 3/2000 | Hu et al. | 435/69.4 |
| 6,071,889 | A * | 6/2000 | Weiss et al. | 514/44 |
| 6,165,783 | A | 12/2000 | Weiss et al. | 435/325 |
| 6,294,346 | B1 * | 9/2001 | Weiss et al. | 435/7.21 |
| 6,497,872 | B1 | 12/2002 | Weiss et al. | 424/93.1 |
| 2002/0197238 | A1 | 12/2002 | Weiss et al. | 424/93.7 |

FOREIGN PATENT DOCUMENTS

| | | |
|---|---|---|
| AU | 2002308471 B2 | 11/2002 |
| EP | 1 132 098 | 9/2001 |
| WO | WO 93/10806 | 6/1993 |
| WO | WO 99/37751 | 7/1999 |
| WO | WO 99/47677 | 9/1999 |
| WO | WO 01/12236 A2 | 2/2001 |
| WO | WO 01/49849 | 7/2001 |
| WO | WO 01/76620 | 10/2001 |
| WO | WO 02/088330 | 11/2002 |

OTHER PUBLICATIONS

Knight et al. Am J. Surg. 1998. 176: 55S-60S.*
Maysinger et al. Trends Biotechnol. Oct. 1997;15(10):410-8.*
Kawabe et al. Neurosci. Res. 1997. 29: 335-343.*
Abboud et al. (1994). *J. Cellular Physiology* 158: 140-150.
Chiu et al. (1984). *Cell* 37: 123-129.
Collins et al. (1985). *Nature* 316: 748-750.
Dvorak et al. (1995). *American J. Pathology* 146: 1029-1039.
Folkman, Judah (1995). *Nature Medicine* 1: 27-31.
Freed et al. (2001). *N. Engl. J. Med.* 344: 710-719.
Gould et al. (2000). *Biol. Psychiatry* 48: 715-720.
Grinspan et al. (1994). *Annals of Neurology* 36 Supp: S140-S142.
Johansson et al. (1999). *Experimental Cell Res.* 253: 733-736.
Johe et al. (1996). *Genes & Development* 10: 3129-3140.
Johnsson et al. (1984). *EMBO J.* 3: 921-928.
Kwon, Yunhee Kim (2002). *J. Biochem. and Mol. Biol.* 35: 87-93.
Maglione et al. (1991). *Proc. Nall. Acad. Sci. USA* 88: 9267-9271.
Nakayama, Kazuhisa (1997). *Biochem. J.* 327: 625-635.
Ostman et al. (1992). *J. Cell Biol.* 118: 509-519.
Piccini et al. (2000). *Annals of Neurology* 48: 689-695.
Soker et al. (1998). *Cell* 92: 735-745.
Takagi et al. (1991). *Neuron* 7: 295-307.
Thomas, Kenneth (1996). *J. Biol. Chem.* 271: 603-606.
Valenzuela et al. (1997). *Brain Res. Rev.* 24: 77-89.
Williams et al. (1997). *Neuron* 18: 553-562.
International Search Report for PCT/IB02/03998, mailed Feb. 10, 2003.
Nikkhah et al., "Platelet-derived growth factor promotes survival of rat and human mesencephalic dopaminergic neurons in culture", *Exp. Brain Res.*, 92:516-523 (1993).
Erlandsson et al. "Immature Neurons From CNS Stem Cells Proliferate in Response to Platelet-Derived Growth Factor." The Journal of Neuroscience, May 15, 2001, 21(10): 3483-3491.
Jin et al., "Vascular Endothelial Growth Factor Rescues HN33 Neural Cells from Death Induced by Serum Withdrawal", *Journal of Molecular Neuroscience*, 14:197-203 (2000).
Oosthuyse et al., "Deletion of the hypoxia-response element in the vascular endothelial growth factor promoter causes motor neuron degeneration", *Nature Genetics*, 28:131-138 (2001).

* cited by examiner

*Primary Examiner* — Chang-Yu Wang
(74) *Attorney, Agent, or Firm* — Mintz Levin Cohn Ferris Glovsky and Popeo, P.C.; Ivor R. Elrifi; Matthew Pavao

(57) ABSTRACT

The invention relates generally to methods of influencing central nervous system cells to produce progeny useful in the treatment of CNS disorders. More specifically, the invention includes methods of exposing a patient suffering from such a disorder to a reagent that modulates the proliferation, migration, differentiation and survival of central nervous system cells. These methods are useful for reducing at least one symptom of the disorder.

14 Claims, 17 Drawing Sheets

A.

B.

Anti-Flk-1

TREATMENT OF PARKINSON'S DISEASE WITH PDGF

RELATED APPLICATIONS

This application claim the benefit of U.S. Ser. No. 60/323,381 filed Sep. 19, 2001 and U.S. Ser. No. 60/326,044 filed Sep. 28, 2001. The contents of their applications are incorporated herein by reference in its entirety.

FIELD OF THE INVENTION

The invention relates generally to methods of influencing neural stem cells and neural progenitor cells to produce progeny that can replace damaged or missing neurons. More specifically, the invention includes methods of exposing a patient suffering from a disorder to a reagent that regulates the proliferation, migration, differentiation and survival of central nervous system cells via modulation of PDGF or VEGF signalling. These methods are useful for reducing at least one symptom of the disorder.

BACKGROUND OF THE INVENTION

The mammalian nervous system comprises a peripheral nervous system (PNS) and a central nervous system (CNS, comprising the brain and spinal cord), and is composed of two principal classes of cells: neurons and glial cells. The glial cells fill the spaces between neurons, nourishing them and modulating their function. Certain glial cells, such as Schwann cells in the PNS and oligodendrocytes in the CNS, also provide a myelin sheath that surrounds neural processes. The myelin sheath enables rapid conduction along the neuron. In the peripheral nervous system, axons of multiple neurons may bundle together in order to form a nerve fiber. These, in turn, may be combined into fascicles or bundles.

It has been established that neural stem cells (NSCs) exist in the adult mammalian brain. This fact is of particular importance since the adult brain was thought to have very limited regenerative capacity. New neurons are continuously added to specific regions of the adult mammalian CNS. These neurons are derived from multipotent stem cells that originate from the ependymal layer in the lateral ventricular wall (Johansson et al., *Cell* 96:25-34 (1999)). Ependymal cells give rise to proliferating cells in the subventricular zone of the ventricle wall, which in turn form neuroblasts. Following migration and differentiation the neuroblasts generate neurons. NSCs also exist in the hippocampal dentate gyrus (Gould et al., *Biol. Psychiatry* 48:715-720 (2000)). Recently it was demonstrated that the human lateral ventricle and the hippocampus also harbor stem cells capable of generating neurons and glia (Johansson et al., *Exp Cell Research* 253: 733-736 (1999)). The use of adult derived stem cells for tissue repair may help to overcome the ethical problems of embryonic cell research.

The role of stem cells in the adult is to replace cells that are lost by natural cell death, injury or disease. The identifying feature of a stem cell is its ability to exhibit self-renewal or to generate more of itself and, therefore, the simplest definition of a stem cell would be a cell with the capacity for self-maintenance. A more stringent (but still simplistic) definition of a stem cell is provided by Potten and Loeffler (Development, 110:1001, 1990) who have defined stem cells as "undifferentiated cells capable of a) proliferation, b) self-maintenance, c) the production of a large number of differentiated functional progeny, d) regenerating the tissue after injury and e) a flexibility in the use of these options."

CNS disorders encompass numerous afflictions such as neurodegenerative diseases (e.g. Alzheimer's and Parkinson's), acute brain injury (e.g. stroke, head injury, cerebral palsy) and a large number of CNS dysfunctions (e.g. depression, epilepsy, and schizophrenia). Degeneration in a brain region known as the basal ganglia can lead to diseases with various cognitive and motor symptoms, depending on the exact location. The basal ganglia consists of many separate regions, including the striatum (which consists of the caudate and putamen), the globus pallidus, the substantia nigra, substantia innominate, ventral pallidum, nucleus basalis of Meynert, ventral tegmental area and the subthalamic nucleus. Many motor deficits are a result of neuronal degeneration in the basal ganglia. Huntington's Chorea is associated with the degeneration of neurons in the striatum, which leads to involuntary jerking movements in the host. Degeneration of a small region called the subthalamic nucleus is associated with violent flinging movements of the extremities in a condition called ballismus, while degeneration in the putamen and globus pallidus is associated with a condition of slow writhing movements or athetosis. Other forms of neurological impairment can occur as a result of neural degeneration, such as cerebral palsy, or as a result of CNS trauma, such as stroke and epilepsy.

Another example is Parkinson's disease which is a chronic neurodegenerative disease particularly affecting the neurons of the substantia nigra pars compacta and its nigrostriatal projections. Although Parkinson's disease is considered a multisystem disease, it is mainly a movement disorder caused by a continuous, long lasting degeneration of the dopaminergic neurons that are located in the mesencephalic substantia nigra pars compacta.

Parkinson's disease (PD) is characterized by tremors, hypokinesia, rigidity and abnormal posture as the principal visible symptoms. The tremors in PD are of the resting type, since they occur when the muscles are in a state of relaxation. Its main pathological feature is the degeneration of dopaminergic neurons which have their cell bodies in the substantia nigra and their terminals projecting into the neostriatum. Dopamine is thus significantly depleted in the neostriatum of PD patients. Changes to the substantia nigra and the neostriatal complex are linked to the tremors seen in PD. Compounds that damage the nigrostriatal dopaminergic system and cause hypokinesia, rigidity and tremors have the potential to be used as models for studying PD. Chemical agents such as 1-methyl-4-phenyl-1,2,3,6-tetrahydropyridine (MPTP) and 6-hydroxydopamine (6-OHDA) damage the nigrostriatal dopaminergic neurons and are widely used to induce symptoms of PD. The effectiveness of these compounds rely on their ability to cause significant damage to the nigrostriatal dopaminergic system. The levels of symptoms are apparently dependent on the degree of nigrostriatal damage, which is somewhat difficult to control. As a result, the symptoms produced by these agents are predominantly rigidity, hypokinesia and movements are not always consistent. Tremor, the most conspicuous symptom of PD is not a characteristic feature of the MPTP and 6-OHDA models.

Levodopa has been historically the medication of choice in treating Parkinson's disease. However, the currently available levodopa preparations are effective only for a relatively short period and may even be deleterious under certain conditions. Administration of levodopa is especially successful during early stages of the disease. Adverse effects of levodopa, such as dyskinesias and hallucinations that occur at early stages of the disease are dose-dependent. These adverse effects are attributed to hypersensitivity of denervated striatal dopaminergic receptors to exogenous dopamine. At late stages of the disease additional types of adverse effects appear as the response to levodopa becomes unpredictable, fluctuative and the duration of the response is reduced.

In order to cure Parkinson's disease, either a grafting procedure of neural tissues to restore dopamine innervation of the stratium or a pharmacological intervention that prevents neural degeneration and triggers renewal of nigral cells must be developed. Recently, transplantation of embryonic dopaminergic neurons have been applied with varying degrees of success (Piccini et al., *Ann. Neurol.* 48:689-695 (2000); Freed et al., *New Engl. J Med.* 344:710-719 (2001)). However, while transplantation approaches represent an improvement over currently available treatments, they suffer from a number of significant drawbacks. For example, after transplantation some cell types fail to integrate with host tissue. Another disadvantage is that immunological incompatibility between donor and host could result in the rejection of the implanted cells. There is also the potential that the transplanted cells can result in tumor formation or pass infectious agents from the donor tissue to the host. Another significant drawback of transplantation procedures is that due to the invasiveness of the procedures, which carry the risks involved in any major neurosurgical operation, damage to healthy brain tissue could occur.

Various treatments with hormones (U.S. Pat. No. 5,116, 873) and mitogens (U.S. Pat. No. 6,165,783) have been also suggested for restoring the striatal dopamine levels by replenishment of dopamine cells. However, none of the curative treatments have reached the market for larger populations of patients.

Thus, there is a need for improved therapies to treat neurodegenerative diseases. It is also necessary to find therapies for enhancing, improving, repairing, restoring and/or protecting the central nervous system function in a mammal, particularly a human at risk for, or suffering from, a CNS disorder or dysfunction associated with damaged CNS cells. Therefore, this invention fulfills a need in the art for a method for treating central nervous system disease which involves replacing cells lost to the disease.

SUMMARY OF THE INVENTION

This invention relates generally to methods of influencing central nervous system cells to produce progeny that can replace damaged or missing neurons.

In one aspect, this invention provides a method of alleviating a symptom of a diseases or disorders of the nervous system comprising administering PDGF, VEGF or a combination thereof to modulate neural stem cell or neural progenitor cell activity in vivo to a patient suffering from the diseases or disorders of the nervous system. In one embodiment, the PDGF, VEGF or combination thereof is administered in an amount of 0.001 ng/kg/day to 10 mg/kg/day. In another embodiment, the PDGF, VEGF or combination thereof is preferably administered in an amount of 0.01 ng/kg/day to 5 mg/kg/day. In a further embodiment, the PDGF, VEGF or combination thereof is more preferably administered in an amount of 0.1 ng/kg/day to 1 mg/kg/day. In another embodiment, the PDGF, VEGF or combination thereof is most preferably administered in an amount of 0.1 ng/kg/day to 1 µg/kg/day. In one embodiment, a highest dose is given over the time span of 6-24 hours is better than a lower dose given during 1-2 weeks. In another embodiment, the highest dose may also be repeated intermittently. Preferred dosages have been described but would also include the following: PDGF (MPTP study); 2.4 microgram/kg/day (mouse) for 3 days; PDGF (6OHDA study); 0.12 microgram/kg/day (rat) for 12 days (approx weight); PDGF (healthy animals) 0.12 microgram/kg/day (rat) for 7 days (approx weight).

Furthermore, it is highly likely that the intraparenchymal dose to achieve effect is less that the intracerebroventricular dose as the latter is a compartment with a considerably higher wash-out rate.

In one embodiment, the PDGF, VEGF or a combination thereof is administered by injection. Injection can be given subcutaneously, intraperitoneally, intramusclularly, intracerebroventricularly, intraparenchymally, intrathecally or intracranially. Intraparenchymally refers to the parenchyma of the brain. The PDGF, VEGF or a combination thereof can also be administered to the buccal, nasal or rectal mucosa. In one embodiment, the PDGF, VEGF, or combination thereof is administered via peptide fusion or micelle delivery.

In one embodiment, the diseases or disorders of the nervous system is selected from the group consisting of neurodegenerative disorders, neural stem cell disorders, neural progenitor disorders, ischemic disorders, neurological traumas, affective disorders, neuropsychiatric disorders and learning and memory disorders. In a preferred embodiment, the diseases or disorders of the nervous system could be Parkinson's disease and Parkinsonian disorders, Huntington's disease, Alzheimer's disease, Amyotrophic Lateral Sclerosis, spinal ischemia, ischemic stroke, spinal cord injury and cancer-related brain/spinal cord injury. In another embodiment, the disease or disorder of the nervous system could be schizophrenia and other psychoses, depression, bipolar depression/disorder, anxiety syndromes/disorders, phobias, stress and related syndromes, cognitive function disorders, aggression, drug and alcohol abuse, obsessive compulsive behaviour syndromes, seasonal mood disorder, borderline personality disorder, Cerebral palsy, life style (smart) drug, multi-infarct dementia, Lewy body dementia, age related/geriatric dementia, epilepsy and injury related to epilepsy, spinal cord injury, brain injury, trauma related brain/spinal cord injury, anti-cancer treatment related brain/spinal cord tissue injury (radiation and cytostatics), infection and inflammation related brain/spinal cord injury, environmental toxin related brain/spinal cord injury, multiple sclerosis, autism, attention deficit disorders, nacrolepsy and sleep disorders.

In one embodiment, the VEGF is selected from the group consisting of VEGF-A, VEGF-B, VEGF-C and VEGF-D and the activity is proliferation or survival. The VEGF-A could be VEGF-$A_{165}$ or VEGF-$A_{121}$. In another embodiment, the PDGF is selected from the group consisting of PDGF-B, PDGF-BB, PDGF-AB, PDGF-C, PDGF-D, PDGF-CC, PDGF-DD, PDGF-BC, PDGF-AC, PDGF-AD and PDGF-BD and the activity is proliferation, differentiation or survival. In another embodiment, the PDGF is PDGF-A or PDGF-AA and the activity is differentiation or survival. In a further embodiment, the PDGF, VEGF or combination thereof could be a dimer consisting of two subunits, wherein each subunit is selected from the group consisting of PDGF A, PDGF B, PDGF C, PDGF D, VEGF A, VEGF B, VEGF C and VEGF D. In a preferred combination for use in the methods of the invention is a dimer. The dimer may be any homodimers or heterodimer with the following members: PDGFA, PDGFB, PDGFC, PDGFD, VEGFA, VEGFB, VEGFC or VEGFD. Since there is a total of eight possibility for the first member of the dimer and eight possibilities for the second member of the dimer, a total of 64 (8×8) combinations is possible and contemplated (e.g., PDGF AA, PDGF AB, VEGF AA, VEGF AB, PDGFA/VEGFB etc.).

In another aspect, the invention includes a method of modulating a PDGF receptor, VEGF receptor, or a combination thereof, on a neural stem cell or neural progenitor cell, the method comprising exposing the cell expressing the receptor to exogenous reagent, antibody, or affibody, wherein the exposure induces the neural stem cell or neural progenitor cell to proliferate or differentiate. In one emodiment, the VEGF receptor is Flt-1, Flk-1 or Flt-4. In another embodiment, the PDGF receptor is PDGF-α receptor or PDGF-β receptor. The reagent is selected from the group consisting of VEGF-A, VEGF-B, VEGF-C, VEGF-D, PDGF-AA, PDGF-BB, PDGF-AB, PDGF-CC, PDGF-DD, PDGF-BC, PDGF-AC, PDGF-AD and PDGF-BD. The antibody could be a monoclonal or a polyclonal antibody. In one embodiment, the neural stem cell or neural progenitor cell is derived from fetal brain, adult brain, neural cell culture or a neurosphere. In another embodiment, the neural stem cell or neural progenitor cell is derived from tissue enclosed by dura mater, peripheral nerves or ganglia.

In a further aspect, the invention provides a method of drug screening and/or drug discovery using a non-human mammal, the method comprising: (a) administering a PDGF or VEGF agonist to the non-human mammal; and (b) comparing the effect of administration of the PDGF or VEGF agonist in the mammal of step (a) with a referenced non-human mammal not administered the PDGF or VEGF agonist. In one embodiment, the agonist is selected from the group consisting of a peptide, small molecule, soluble receptor and receptor agonist wherein the exposure induces a neural stem cell or neural progenitor cell to proliferate or differentiate. In one embodiment, the soluble receptor is a VEGF receptor, PDGF receptor or a combination thereof. In another embodiment, the VEGF receptor is selected from the group consisting of Flt-1, Flk-1 and Flt-4. In a further embodiment, the PDGF receptor is a PDGF-α receptor, a PDGF-β receptor or a combination thereof.

In another aspect, the invention includes a method for reducing a symptom of a central nervous system disorder in a mammal in need of such treatment comprising administering PDGF, VEGF or a PDGF or VEGF agonist to the mammal. In another aspect, the method further comprises administering a ventricle wall permeability enhancer. In one embodiment, the ventricle wall permeability enhancer is administered before, during or after administration of PDGF, VEGF or a PDGF or VEGF agonist. In another aspect, the ventricle wall permeability enhancer or the PDGF, VEGF or PDGF or VEGF agonist are admixed with a pharmaceutically acceptable carrier. In a further embodiment, the method, further comprises administration of one or more agents selected from the group consisting of stem cell mitogens, survival factors, glial-lineage preventing agents, anti-apoptotic agents, anti-stress medications, neuroprotectants, anti-pyrogenics and a combination thereof.

In one aspect, the invention provides a method for inducing the in situ proliferation or differentiation of a neural stem cell or neural progenitor cell located in the neural tissue of a mammal, the method comprising administering a therapeutically effective amount of PDGF or VEGF to the neural tissue to induce the proliferation or differentiation of the cell. In one embodiment, the administration is systemic or local. In another embodiment, the administration of the PDGF, VEGF or PDGF or VEGF agonist alleviates a symptom of a diseases or disorders of the nervous system.

In a further aspect, the invention includes a method for accelerating the growth of neural stem cells or neural progenitor cells in a desired target tissue in a subject, comprising administering intramuscularly to the subject an expression vector containing a PDGF or VEGF gene in a therapeutically effective amount. In one embodiment, the expression vector is a non-viral expression vector encapsulated in a liposome.

In another aspect, the invention provides a method of enhancing neurogenesis in a patient suffering from a disease or disorder of the central nervous system, by intraventricular infusion of PDGF, VEGF or PDGF or VEGF receptor agonist.

In another aspect, the invention includes a method of increasing the number of dopaminergic neurons in a patient suffering from Parkinson's disease comprising the steps of: (a) infusing the patient with PDGF to a lateral ventricle of the brain; (b) monitoring the patient to determine if there is proliferation and differentiation of NSCs and NPCs; and (c) repeating step (a) until the desired effect is achieved.

In one aspect, the invention provides a method for producing a population of cells enriched for human neural stem cells or human neural progenitor cells which can initiate neurospheres, comprising: (a) contacting a population containing neural stem cells or neural progenitor cells with a reagent that recognizes a determinant on a VEGF or PDGF receptor; and (b) selecting for cells in which there is contact between the reagent and the determinant on the surface of the cells of step (a), to produce a population highly enriched for central nervous system stem cells. In one embodiment, the reagent is a reagent selected from the group consisting of a soluble receptor, a small molecule, a peptide, an antibody and an affibody. In another embodiment, the population containing neural stem cells or neural progenitor cells is obtained from any population of cells which gives rise to neural tissue. The neural tissue could fetal brain or adult brain.

In another aspect, the invention includes a method of activating a VEGF or PDGF receptor on a neural stem cell or neural progenitor cell, the method comprising exposing a neural stem cell or neural progenitor cell expressing a receptor to exogenous reagent, antibody, or affibody, wherein the exposure induces the neural stem cell or neural progenitor cell to proliferate or differentiate. In one embodiment, the neural stem cell or neural progenitor cell is derived from fetal brain, adult brain, neural cell culture or a neurosphere.

In a further aspect, the invention provides an in vitro cell culture comprising a cell population enriched in receptor expressing cells wherein the receptors are selected from the group consisting of Flt-1, Flk-1, Flt-4, PDGF-α and PDGF-β receptor.

In another aspect, the invention provides a method for treating diseases or disorders of the central nervous system comprising administering the population of neural stem cells or neural progenitor cells described in a previous aspect of the invention to a mammal in need thereof.

In one aspect, the invention includes a non-human mammal engrafted with the human neural stem cells or neural progenitor cells described in a previous aspect of the invention. In one embodiment, the non-human mammal is selected from the group consisting of a rat, mouse, rabbit, horse, sheep, pig and guinea pig.

In a further aspect, the invention provides a method of reducing a symptom of a disease or disorder of the central nervous system in a subject comprising the steps of administering into the spinal cord of the subject a composition comprising a population of isolated primary neurons obtained from a fetus; and PDGF, VEGF, a PDGF or VEGF agonist or a combination thereof such that the symptom is reduced.

In another aspect, the invention includes a host cell transformed or transfected with a molecule selected from the group consisting of SEQ ID NOs: 1, 2, 3 and 4. In one embodiment, the host cell is a eukaryotic cell or a prokaryotic cell. In another embodiment, the host cell is selected from the group consisting of a mammalian cell, a bacterial cell, a yeast. In a further embodiment, FuGENE 6 transfection reagent (Roche Diagnostics) is used to transfect the host cell.

In one embodiment, the invention includes a method of gene delivery and expression in a target cell of a mammal, comprising the step of introducing a viral vector into the target cell, wherein the viral vector has at least one insertion site containing a nucleic acid selected from the group consisting of SEQ ID NOs: 1, 2, 3 and 4, the nucleic acid gene operably linked to a promoter capable of expression in the host. In one emodiment, the viral vector is a non-lytic viral vector.

In a further embodiment, the invention includes a method of gene delivery and expression in a target cell of a mammal comprising the steps of: (a) providing an isolated nucleic acid fragment of sequence selected from the group consisting of SEQ ID NOs: 1, 2, 3 and 4; (c) selecting a viral vector with at least one insertion site for insertion of the isolated nucleic acid fragment operably linked to a promoter capable of expression in the target cells; (d) inserting the isolated nucleic acid fragment into the insertion site, and (e) introducing the vector into the target cell wherein the gene is expressed at detectable levels. In one embodiment, the virus is selected from the group consisting of retrovirus, adenovirus, and pox virus. In another embodiment, the pox virus is vaccinia. In a preferred embodiment, the virus is selected from the group consisting of retrovirus, adenovirus, iridoviruses, coronaviruses, togaviruses, caliciviruses and picornaviruses. In another embodiment, the virus is a strain that has been genetically modified or selected to be non-virulent in a host.

In another aspect, the invention includes a method for alleviating a symptom of a disease or disorder of the central nervous system in a patient comprising the steps of: (a) providing a population of neural stem cells or neural progenitor cells; (b) suspending the neural stem cells or neural progentor cells in a solution comprising a mixture comprising a growth factor dimer wherein each half of the dimer is selected from the group consisting of PDGF A, PDGF B, PDGF C, PDGF D, VGEF A, VGEF B, VGEF C, and VGEF D, to generate a cell suspension; (c) delivering the cell suspension to an injection site in the central nervous system of the patient to alleviate the symptom. In one embodiment, the method further comprises the step of injecting the injection site with the growth factor for a period of time before the step of delivering the cell suspension. In another embodiment, the method further comprises the step of injecting the injection site with said growth factor after said delivering step.

Additional aspects, features, embodiments and advantages of the invention will be set forth, in the description that follows, or may be learned from practicing or using the invention. The objects and advantages may be realized and attained by means of the features and combinations particularly pointed out throughout this description and the appended claims. It is to be understood that the foregoing general description and the following detailed description are exemplary and explanatory only and are not to be viewed as being restrictive of the invention as claimed.

DETAILED DESCRIPTION OF THE INVENTION

Figure 1:
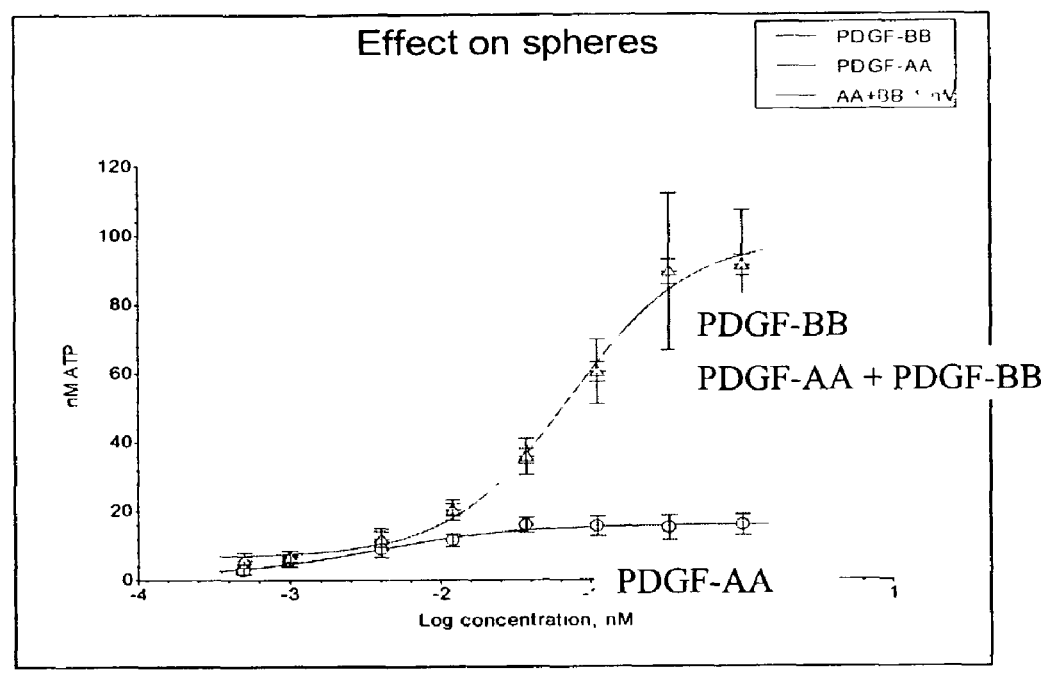
FIG. 1 depicts the effect of PDGFs on proliferation of cultured, non-adherent mouse neurospheres.

It has been discovered that certain reagents are capable of modulating the differentiation, migration, proliferation and survival of neural stern/progenitor cells both in vitro and in vivo. As used herein, the term "modulate" refers to having an affect in such a way as to alter the differentiation, migration, proliferation and survival of neural stem cell (NSC) or neural progenitor cell (NPC) activity. Since undifferentiated, pluripotent stem cells can proliferate in culture for a year or more, the invention described in this disclosure provides an almost limitless supply of neural precursors.

As used herein, the term "neural stem cells" (NSCs) can be identified by their ability to undergo continuous cellular proliferation, to regenerate exact copies of themselves (self-renew), to generate a large number of regional cellular progeny, and to elaborate new cells in response to injury or disease. The terms "neural progenitor cells" or "neural precursor cells" (NPCs) mean cells that can generate progeny that are either neuronal cells (such as neuronal precursors or mature neurons) or glial cells (such as glial precursors, mature astrocytes, or mature oligodendrocytes). Typically, the cells express some of the phenotypic markers that are characteristic of the neural lineage. Typically, they do not produce progeny of other embryonic germ layers when cultured by themselves in vitro unless dedifferentiated or reprogrammed in some fashion.

As used herein, the term "reagent" refers to any substance that is chemically and biologically capable of activating a receptor, including peptides, small molecules, antibodies (or fragments thereof), affibodies and any molecule that dimerizes or multimerizes the receptors or replaces the need for activation of the extracellular domains. In one embodiment, the reagent is a small molecule.

As used herein, the term "antibody" as used in this disclosure refers to both polyclonal and monoclonal antibody. The ambit of the term deliberately encompasses not only intact immunoglobulin molecules, but also such fragments and derivatives of immunoglobulin molecules (such as single chain Fv constructs, diabodies and fusion constructs) as may be prepared by techniques known in the art, and retaining a desired antibody binding specificity. The term "affibody" (U.S. Pat. No. 5,831,012) refers to highly specific affinity proteins that can be designed to bind to any desired target molecule. These antibody mimics can be manufactured to have the desired properties (specificity and affinity), while also being highly robust to withstand a broad range of analytical conditions, including pH and elevated temperature. The specific binding properties that can be engineered into each capture protein allow it to have very high specificity and the desired affinity for a corresponding target protein. A specific target protein will thus bind only to its corresponding capture protein. The small size (only 58 amino acids), high solubility, ease of further engineering into multifunctional constructs, excellent folding and absence of cysteines, as well as a stable scaffold that can be produced in large quantities using low cost bacterial expression systems, make affibodies superior capture molecules to antibodies or antibody fragments, such as Fab or single chain Fv (scFv) fragments, in a variety of Life Science applications.

Preferred reagents of the invention include members of the Vascular Endothelial Growth Factor (VEGF) family and members of the Platelet Derived Growth Factor (PDGF) family. In one embodiment, the reagent may be VEGF-A, VEGF-B, VEGF-C, VEGF-D, PDGF-A, PDGF-B, PDGF-B, PDGF-AA, PDGF-BB or PDGF-AB.

The invention provides a method for in vivo modulation of PDGF and VEGF activity and for therapeutic administration of PDGF and VEGF and drug screening. In one embodiment, PDGF, VEGF or their agonist are administered to neural tissue. In a preferred embodiment, the neural tissue is fetal or adult brain. In yet another embodiment, the population containing neural or neural-derived cells is obtained from a neural cell culture or neurosphere.

Receptors for the invention include members of the VEGF receptors and members of the PDGF receptors. Such receptors may include: Flt-1, Flk-1, Flt-4, PDGF-α, PDGF-β and VEGF receptor.

PDGF Receptors and Their Ligands

PDGF, an autocrine cytokine, is involved in the development of the CNS as well as in the maintenance of the adult CNS. The mechanisms triggered by PDGF include differentiation and survival of dopaminergic neurons. In vitro, PDGF was shown to support differentiation and to influence multipotent stem cells towards a neuronal fate. Johe et al., 1996, Genes Dev 10, 3129-3140; Williams et al., 1997, Neuron 18, 553-562.

PDGF is also a potent mitogen for mesenchymal, glial, and capillary endothelial cells. As such, it acts as a strong chemoattractant for fibroblasts and smooth muscle cells, as well as monocytes and neutrophils. The mitogenic activity of the localized PDGF results in proliferation of these cells at the site of injury, contributing to the process of wound repair.

Purified native PDGF, a glycoprotein of about 30,000 daltons, is composed of two disulfide-linked polypeptide chains. Two forms of these chains, designated A and B, have been identified. The native protein occurs as the homodimer AA or BB or the heterodimer AB, or a mixture thereof. A partial amino acid sequence for the PDGF-A chain has been identified (Johnsson et al. (1984) EMBO J. 3:921-928) and cDNAs encoding two forms of PDGF A-chain precursors have been described (U.S. Pat. No. 5,219,759). The mature A-chain consists of a 104 amino acid polypeptide that is derived by proteolytic processing of a 211 amino acid precursor polypeptide. The cDNA encoding the PDGF-B chain has also been described (Nature (1985) 316:748-750). The mature B-chain consists of a 109 amino acid polypeptide that is derived by proteolytic processing of a 241 amino acid precursor polypeptide. The mature A and B chains of PDGF show sequence identity of 51%, with the eight cysteine residues being conserved in each of the chains (Johnsson et al. (1984) EMBO J. 3:921-928).

The three isoforms of PDGF, PDGF-AA, PDGF-AB, and PDGF-BB, interact differentially with structurally related receptors designated PDGF α and β receptors. Each of these receptors has an extracellular region featuring five immunoglobulin-like domains, a lipophilic transmembrane domain and an intracellular part with a tyrosine kinase domain containing a characteristic insert amino acid sequence. The tyrosine kinase activity of these receptors is essential for transmission of the mitogenic signal into the cell.

The three dimeric forms of PDGF exhibit different binding affinities for the two known PDGF receptor gene products, α and β. The β receptor recognizes the PDGF B chain and is dimerized in the presence of PDGF-BB. The α receptor recognizes the PDGF B and A chains and can be dimerized by PDGF-BB, PDGF-AA, and PDGF-AB (see, for example, Abboud et al (1994) J. Cell. Phys. 158:140-150). The amino acid residue region of PDGF-BB which is involved in binding or activation of the receptor has been narrowed down to residues $Ile^{25}$-$Phe^{37}$ (Giese et al. (1990) Mol. Cell. Biol. 10:5496-5501).

Most recently, an additional member of the PDGF/VEGF family of growth factors was identified, which is called PDGF-C. PDGF-C has a two-domain structure not previously recognized within this family of growth factors, an N-terminal Clr/Cls/embryonic sea urchin protein Uegf/bone morphogenetic protein 1 (CUB) domain, and a C-terminal PDGF/VEGF homology domain (P/VHD). The structure of the P/VHD in PDGF-C shows a low overall sequence identity with other PDGF/VEGF homology domains, although the eight invariant cysteine residues involved in inter- and intramolecular disulfide bond formation are present. The cysteine spacing in the central, most conserved region of this domain is different from other PDGF/VEGF domains, with an insertion of three amino acid residues. Despite the fact that the insertion occurs close to the loop 2 region which has been proposed to be involved in receptor binding, it was shown that this domain of PDGF-CC dimers binds PDGFR-alpha with an affinity almost identical to homodimers of PDGF-A or -B chains. In addition, four extra cysteine residues are present in this domain. Full length and truncated PDGF-CC dimers were found not to bind to VEGFR-1, -2 or -3, or to PDGFR-beta.

PDGF-C requires proteolytic removal of the N-terminal CUB domain for receptor binding and activation of the receptor. This indicates that the CUB domains are likely to sterically block the receptor binding epitopes of the unprocessed dimer. The in vitro and in vivo proteolytically processed proteins are devoid of N-terminal portions corresponding to more than 14-16 kDa as determined from SDS-PAGE analysis that is consistent with a loss of the 110 amino acid long CUB domain and a variable length portion of the hinge region between the CUB and core domains.

PDGF-C is not proteolytically processed during secretion in transfected COS cells indicating that proteolytic removal of the CUB domain occurs extracellularly, and not during secretion. This is in contrast to PDGF-A and -B (Stman et al., J. Cell. Biol., 1992 118 509-519) which appear to be processed intracellularly by furin-like endoproteases (Nakayama et al., Biochem J., 1997 327 625-635).

In situ localization studies demonstrate expression of PDGF-C in certain epithelial structures, and PDGFR-alpha in adjacent mesenchyme, indicating the potential of paracrine signaling in the developing embryo. PDGF-C expression seems particularly abundant at sites of ongoing ductal morphogenesis, indicating a role of the factor in connective tissue remodeling at these sites. The expression pattern is distinct from that of PDGF-A or PDGF-B indicating that the three growth factors have different roles despite their similar PDGFR-alpha binding and signaling activities. This is illustrated by the mouse embryonic kidney, in which PDGF-C is expressed in early aggregates of metanephric mesenchyme undergoing epithelial conversion, whereas PDGF-A is expressed in more mature tubular structures, and PDGF-B by vascular endothelial cells. PDGFR-alpha is expressed in the mesenchyme of the kidney cortex, adjacent to the sites of PDGF-C expression, indicating that this mesenchyme may be targeted specifically by PDGF-C. Indeed, PDGFR-alpha-/-mouse embryos show an extensive loss of the cortical mesenchyme adjacent to sites of PDGF-C expression, not seen in PDGF-A-/-mice or in PDGF-A/B-/-mice, indicating that PDGF-C has an essential role in the development of kidney mesenchyme. Northern blots show PDGF-C mRNA in a variety of human tissues, including heart, liver, kidney, pancreas and ovary.

Another protein in the PDGF family is PDGF-D. Structural predictions based on the PDGF-D sequence and its homology to other growth factors suggests that the polypeptide can form homomultimers or heteromultimers. PDGF-D heteromultimers may comprise a polypeptide from another member of the PDGF/VEGF family of proteins, including VEGF, VEGF-B, VEGF-C, VEGF-D, PDGF-D/PDGF-C, PlGF (Maglione et al., Proc. Natl. Acad. Sci. USA 88:9267-9271, 1991), PDGF-A (Murray et al., U.S. Pat. No. 4,899,919; Heldin et al., U.S. Pat. No. 5,219,759), or PDGF-B (Chiu et al., Cell 37:123-129, 1984; Johnsson et al., EMBO J. 3:921-928, 1984).

The PDGF-D polypeptide chain comprises a growth factor domain, a CUB domain, and an interdomain linking the CUB and growth factor domains. The growth factor domain is characterized by an arrangement of cysteine residues and beta strands that is characteristic of the "cystine knot" structure of the PDGF family. The CUB domain shows sequence homology to CUB domains in the neuropilins (Takagi et al., Neuron 7:295-307, 1991; Soker et al., Cell 92:735-745, 1998), human bone morphogenetic protein-i (Wozney et al., Science 242: 1528-1534, 1988), porcine seminal plasma protein and bovine acidic seminal fluid protein (Romero et al., Nat. Struct. Biol. 4:783-788, 1997), and *X. laevis* tolloid-like protein (Lin et al., Dev. Growth Differ. 39:43-51, 1997).

Binding of PDGF to its receptors initiates numerous biological responses including proliferation, chemotaxis, differentiation and survival. The signal transduction process involves receptor dimerization and activation of intrinsic receptor kinase activity which leads to receptor autophosphorylation at up to nine sites. Subsequently, depending on the cell context the signal relay cascade diverges to involve many different pathways, most of which end with an event regulating transcription (for refs see Valenzuela et al., 1997, Brain Res. Rev 24, 77-89). Receptors for PDGF are expressed in structures relevant for the treatment of Parkinson's disease. See, Valenzuela et al., 1997, Brain Res. Rev 24, 77-89.

PDGF and its receptors participate in various physiological processes such as embryonal development and wound healing. An abnormally high activity of PDGF is believed to play a central role in the etiology of certain adverse pathophysiological situations, such as atherosclerosis and restenosis, as well as in other non-malignant diseases such as pulmonary fibrosis, glomerular nephritis, and rheumatoid arthritis. Moreover, the PDGF B-chain was acquired as the sis oncogene by the acutely transforming simian sarcoma virus. Expression of a PDGF-like growth factor in cells infected with simian sarcoma virus or transfected with the sis oncogene leads to their transformation due to the persistent autocrine stimulation of the resident PDGF receptors. Furthermore, certain human tumors possess PDGF receptors and express the genes for PDGF which suggest that autocrine growth stimulation via PDGF receptors contributes to the malignant phenotype of these tumors.

The nucleic acid sequences for human PDGF-A, PDGF-B, PDGF-C and PDGF-D are represented below:

```
PDGF-A (GenBank entry # NM_002607)
                                                              (SEQ ID NO:1)
ACGCGCGCCCTGCGGAGCCCGCCCAACTCCGGCGAGCCGGGCCTGCGCCTACTCCTCCTCCTCTCCCGGCGGCGG

CTGCGGCGGAGGCGCCGACTCGGCCTTGCGCCCGCCCTCAGGCCCGCGCGGGCGGCGCAGCGAGGCCCCGGGCGGCGG

GTGGTGGCTGCCAGGCGGCTCGGCCGCGGGCGCTGCCCGGCCCCGGCGAGCGGAGGGCGGAGCGCGGCGCCGAGCCG

AGGGCGCGCCGCGGAGGGGGTGCTGGGCCGCGCTGTGCCCGGCCGGGCGGCGGCTGCAAGAGGAGGCCGGAGGCGAGC

GCGGGGCCGGCGGTGGGCGCGCAGGGCGGCTCGCAGCTCGCAGCCGGGGCCGGGCCAGGCGTTCAGGCAGGTGATCGG

TGTGGCGGCGGCGGCGGCGGCGGCCCCAGACTCCCTCCGGAGTTCTTCTTGGGGCTGATGTCCGCAAATATGCAGAAT

TACCGGCCGGGTCGCTCCTGAAGCAGCGCGGGGAGCGAGCGCGGCGGCGGCCAGCACCGGGAACGCACCGAGGAAGA

AGCCCAGCCCCCGCCCTCCGCCCCTTCCGTCCCCACCCCCTACCCGGCGGCCCAGGAGGCTCCCCGGCTGCGGCGCGC

ACTCCCTGTTTCTCCTCCTCCTGGCTGGCGCTGCCTGCCTCTCCGCACTCACTGCTCGCCGGGCGCCGTCCGCCAGCT

CCGTGCTCCCCGCGCCACCCTCCTCCGGGCCGCGCTCCCTAAGGGATGGTACTGAATTTCGCCGCCACAGGAGACCGG
```

-continued

CTGGAGCGCCCGCCCCGCGCCTCGCCTCTCCTCCGAGCAGCCAGCGCCTCGGGACGCGATGAGGACCTTGGCTTGCCT

GCTGCTCCTCGGCTGCGGATACCTCGCCCATGTTCTGGCCGAGGAAGCCGAGATCCCCCGCGAGGTGATCGAGAGGCT

GGCCCGCAGTCAGATCCACAGCATCCGGGACCTCCAGCGACTCCTGGAGATAGACTCCGTAGGGAGTGAGGATTCTTT

GGACACCAGCCTGAGAGCTCACGGGGTCCACGCCACTAAGCATGTGCCCGAGAAGCGGCCCCTGCCCATTCGGAGGAA

GAGAAGCATCGAGGAAGCTGTCCCCGCTGTCTGCAAGACCAGGACGGTCATTTACGAGATTCCTCGGAGTCAGGTCGA

CCCCACGTCCGCCAACTTCCTGATCTGGCCCCCGTGCGTGGAGGTGAAACGCTCCACCGGCTGCTGCAACACGAGCAG

TGTCAAGTGCCAGCCCTCCCGCGTCCACCACCGCAGCGTCAAGGTGGCCAAGGTGGAATACGTCAGGAAGAAGCCAAA

ATTAAAAGAAGTCCAGGTGAGGTTAGAGGAGCATTTGGAGTGCGCCTGCGCGACCACAAGCCTGAATCCGGATTATCG

GGAAGAGGACACGGGAAGGCCTAGGGAGTCAGGTAAAAAACGGAAAAGAAAAAGGTTAAAACCCACCTAAGATGTGAG

GTGAGGATGAGCCGCAGCCCTTTCCTGGGACATGGATGTACATGGCGTGTTACATTCCTGAACCTACTATGTACGGTG

CTTTATTGCCAGTGTGCGGTCTTTGTTCTCCTCCGTGAAAAACTGTGTCCGAGAACACTCGGGAGAACAAAGAGACAG

TGCACATTTGTTTAATGTGACATCAAAGCAAGTATTGTAGCACTCGGTGAAGCAGTAAGAAGCTTCCTTGTCAAAAAG

AGAGAGAGAGAGAGAGAGAGAAAACAAAACCACAAATGACAAAAACAAAACGGACTCACAAAAATATCTAAACTCG

ATGAGATGGAGGGTCGCCCCGTGGGATGGAAGTGCAGAGGTCTCAGCAGACTGGATTTCTGTCCGGGTGGTCACAGGT

GCTTTTTTGCCGAGGATGCAGAGCCTGCTTTGGGAACGACTCCAGAGGGGTGCTGGTGGGCTCTGCAGGGCCCGCAGG

AAGCAGGAATGTCTTGGAAACCGCCACGCGAACTTTAGAAACCACACCTCCTCGCTGTAGTATTTAAGCCCATACAGA

AACCTTCCTGAGAGCCTTAAGTGGTTTTTTTTTTGTTTTGTTTTGTTTTTTTTTTTGTTTTTTTTTTTTT

TTTTTTTACACCATAAAGTGATTATTAAGCTTCCTTTTACTCTTTGGCTAGCTTTTTTTTTTTTTTTTTTTTTT

TTTTTTAATTATCTCTTGGATGACATTTACACCGATAACACACAGGCTGCTGTAACTGTCAGGACAGTGCGACGGTAT

TTTTCCTAGCAAGATGCAAACTAATGAGATGTATTAAAATAAACATGGTATACCTACCTATGCATCATTTCCTAAATG

TTTCTGGCTTTGTGTTTCTCCCTTACCCTGCTTTATTTGTTAATTTAAGCCATTTTGAAAGAACTATGCGTCAACCAA

TCGTACGCCGTCCCTGCGGCACCTGCCCCAGAGCCCGTTTGTGGCTGAGTGACAACTTGTTCCCCGCAGTGCACACCT

AGAATGCTGTGTTCCCACGCGGCACGTGAGATGCATTGCCGCTTCTGTCTGTTGTTGGTGTGCCCTGGTGCCGTGG

TGGCGGTCACTCCCTCTGCTGCCAGTGTTTGGACAGAACCCAAATTCTTTATTTTTGGTAAGATATTGTGCTTTACCT

GTATTAACAGAAATGTGTGTGTGTGGTTTGTTTTTTTGTAAAGGTGAAGTTTGTATGTTTACCTAATATTACCTGTTT

TGTATACCTGAGAGCCTGCTATGTTCTTCTTTTGTTGATCCAAAATTAAAAAAAAAAATACCACCAAC

PDGF-B (GenBank entry # NM_002608)

(SEQ ID NO:2)

ggtggcaacttctcctcctgcggccgggagcggcctgcctgcctccctgcgcacccgcagcctcccccgctgcctccc tagggctcccctccggccgccagcgcccattttcattccctagatagagatactttgcqcgcacacacatatacacg cgcgcaaaaaggaaaaaaaaaaaaaaagcccaccctccagcctcgctgcaaaqagaaaaccggagcagccgcagctc gcagctcgcagctcgcagcccgcagccgcagaggacgcccagagcggcgagcaggcgggcagacggaccgacggact cgcgccgcgtccacctgtcggccgggcccagccgagcgcgcagcgggcacgccgcgcgcgcggagcagccgtgcccgc cgcccgggcccgccgccagggcgcacacgctcccgcccccctacccggcccgggcggagtttgcacctctccctgcc cgggtgctcgagctgccgttgcaaagccaactttggaaaaagttttttgggggagacttgggccttgaggtgcccagc tccgcgctttccgattttgggggccttttccagaaaatgttgcaaaaaagctaagccggcgggcagaggaaaacgcctg tagccggcgagtgaagacgaaccatcgactgccgtgttccttttcctcttggaggttggagtcccctgggcgcccca cacggctagacgcctcggctggttcgcgacgcagccccccggccgtggatgctgcactcgggctcggatccgcccag gtagccggcctcggacccaggtcctgcgcccaggtcctcccctgcccccagcgacggagccggggccgggggcggcg gcgccggggcatgcgggtgagccgcggctgcagaggcctgagcgcctgatcgccgcggacctgagccgagcccaccc ccctccccagcccccaccctggccgcgggggcggcgcgctcgatctacgcgtccggggcccgcggggccgggcccg -continued

```
gagtcggcatgaatcgctgctgggcgctcttcctgtctctctgctgctacctgcgtctggtcagcgccgaggggacc ccattcccgaggagctttatgagatgctgagtgaccactcgatccgctcctttgatgatctccaacgcctgctgcacg gagaccccggagaggaagatggggccgagttggacctgaacatgacccgctcccactctggaggcgagctggagagct tggctcgtggaagaaggagcctgggttccctgaccattgctgagccggccatgatcgccgagtgcaagacgcgcaccg aggtgttcgagatctcccggcgcctcatagaccgcaccaacgccaacttcctggtgtggccgccctgtgtggaggtgc agcgctgctccggctgctgcaacaaccgcaacgtgcagtgccgccccacccaggtgcagctgcgacctgtccaggtga gaaagatcgagattgtgcggaagaagccaatctttaagaaggccacggtgacgctggaagaccacctggcatgcaagt gtgagacagtggcagctgcacggcctgtgacccgaagcccgggggttcccaggagcagcgagccaaaacgccccaaa ctcgggtgaccattcggacggtgcgagtccgccggccccccaagggcaagcaccggaaattcaagcacacgcatgaca agacggcactgaaggagacccttggagcctaggggcatcggcaggagagtgtgtgggcagggttatttaatatggtat ttgctgtattgccccatggggtccttggagtgataatattgtttccctcgtccgtctgtctcgatgcctgattcgga cggccaatggtgcttcccccaccccctccacgtgtccgtccacccttccatcagcgggtctcctcccagcggcctccgg tcttgcccagcagctcaaagaagaaaaagaaggactgaactccatcgccatcttcttcccttaactccaagaacttgg gataagagtgtgagagagactgatggggtcgctctttgggggaaacgggttccttcccctgcacctggcctgggccac acctgagcgctgtggactgtcctgaggagccctgaggacctctcagcatagcctgcctgatccctgaaccccctggcca gctctgaggggaggcacctccaggcaggccaggctgcctcggactccatggctaagaccacagacgggcacacagact ggagaaaaccccctcccacggtgcccaaacaccagtcacctcgtctccctggtgcctctgtgcacagtggcttctttc gttttcgttttgaagacgtggactcctcttggtgggtgtggccagcacaccaagtggctgggtgccctctcaggtggg ttagagatggagtttgctgttgaggtggtgtagatggtgacctgggtatccctgcctcctgccaccccttcctcccc atactccactctgattcacctcttcctctggttcctttcatctctctacctccaccctgcattttcctcttgtcctgg cccttcagtctgctccaccaagggctcttgaacccttattaaggcccagatgaccccagtcactcctctctaggg cagaagactagaggccagggcagcaagggacctgctcatcatattccaacccagccacgactgccatgtaaggttgtg cagggtgtgactgcacaaggacattgtatgcagggagcactgttcacatcatagataaagctgatttgtatatttat tatgacaatttctggcagatgtaggtaaagaggaaaaggatccttttcctaattcacacaaagactccttgtggactg gctgtgcccctgatgcagcctgtggctggagtggccaaataggagggagactgtggtagggcagggaggcaacactg ctgtccacatgacctccatttcccaaagtcctctgctccagcaactgcccttccaggtgggtgtgggacacctgggag aaggtctccaagggagggtgcagccctcttgcccgcaccccctccctgcttgcacacttccccatctttgatccttctg agctccacctctggtggctcctcctaggaaaccagctcgtgggctgggaatgggggagagaagggaaaagatccccaa gaccccctggggtgggatctgagctcccacctcccttcccacctactgcactttccccctttcccgccttccaaaacct gcttccttcagtttgtaaagtcggtgattatattttgggggctttccttttatttttttaaatgtaaaatttatttat attccgtatttaaagttgt
```

PDGF-c (GenBank entry # AF260738)

(SEQ ID NO:3)

```
ggcacgaggattatgtggaaactaccctgcgattctctgctgccagagcaggctcggcgcttccaccccagtgcagcc ttcccctggcggtggtgaaagagactcgggagtcgctgcttccaaagtgcccgccgtgagtgagctctcaccccagtc agccaaatgagcctcttcgggcttctcctgctgacatctgccctggccggccagagacaggggactcaggcggaatcc aacctgagtagtaaattccagttttccagcaacaaggaacagaacggagtacaagatcctcagcatgagagaattatt actgtgtctactaatggaagtattcacagcccaaggtttcctcatacttatccaagaaatacggtcttggtatggaga ttagtagcagtagaggaaaatgtatggatacaacttacgtttgatgaaagatttgggcttgaagaccagaagatgac atatgcaagtatgattttgtagaagttgaggaacccagtgatggaactatattagggcgctggtgtggttctggtact gtaccaggaaaacagatttctaaaggaaatcaaattaggataagatttgtatctgatgaatattttccttctgaacca gggttctgcatccactacaacattgtcatgccacaattcacagaagctgtgagtccttcagtgctaccccttcagct
```

-continued ttgccactggacctgcttaataatgctataactgcctttagtaccttggaagaccttattcgatatcttgaaccagag agatggcagttggacttagaagatctatataggccaacttggcaacttcttggcaaggcttttgtttttggaagaaaa tccagagtggtggatctgaaccttctaacagaggaggtaagattatacagctgcacacctcgtaacttctcagtgtcc ataagggaagaactaaagagaaccgataccattttctggccaggttgtctcctggttaaacgctgtggtgggaactgt gcctgttgtctccacaattgcaatgaatgtcaatgtgtcccaagcaaagttactaaaaaataccacgaggtccttcag ttgagaccaaagaccggtgtcaggggattgcacaaatcactcaccgacgtggccctggagcaccatgaggagtgtgac tgtgtgtgcagagggagcacaggaggatagccgcatcaccaccagcagctcttgcccagagctgtgcagtgcagtggc tgattctattagagaacgtatgcgttatctccatccttaatctcagttgtttgcttcaaggaccttcatcttcagga tttacagtgcattctgaaagaggagacatcaaacagaattaggagttgtgcaacagctcttttgagaggaggcctaaa ggacaggagaaaaggtcttcaatcgtggaaagaaaattaaatgttgtattaaatagatcaccagctayttcagagtt accatgtacgtattccactagctgggttctgtatttcagttctttcgatacggcttagggtaatgtcagtacaggaaa aaaactgtgcaagtgagcacctgattccgttgccttgcttaactctaaagctccatgtcctgggcctaaaatcgtata aaatctggatttttttttttttttttgctcatattcacatatgtaaaccagaacattctatgtactacaaacctggt ttttaaaaaggaactatgttgctatgaattaaacttgtgtcgtgctgataggaaaaaaaaaaaaaaaaaaaaaaaaaa aaaaaaaaa

PDGF-D (GenBank entry # AF336376)

(SEQ ID NO:4)

cgctcggaaagttcagcatgcaggaagtttggggagagctcggcgattagcacagcgacccgggccagcgcagggcga gcgcaggcggcgagagcgcagggcggcgcggcgtcggtcccgggagcagaacccggcttttcttggagcgacgctgt ctctagtcgctgatcccaaatgcaccggctcatctttgtctacactctaatctgcgcaaacttttgcagctgtcggga cacttctgcaaccccgcagagcgcatccatcaaagctttgcgcaacgccaacctcaggcgagatgagagcaatcacct cacagacttgtaccgaagagatgagaccatccaggtgaaaggaaacggctacgtgcagagtcctagattcccgaacag ctacccccaggaacctgctcctgacatggcggcttcactctcaggagaatacacggatacagctagtgtttgacaatca gtttggattagaggaagcagaaaatgatatctgtaggtatgattttgtggaagttgaagtatatccgaaaccagtac cattattagaggacgatggtgtggacacaaggaagttcctccaaggataaaatcaagaacgaaccaaattaaaatcac attcaagtccgatgactactttgtggctaaacctggattcaagatttattattctttgctggaagatttccaacccgc agcagcttcagagaccaactgggaatctgtcacaagctctatttcaggggtatcctataactctccatcagtaacgga tcccactctgattgcggatgctctggacaaaaaattgcagaatttgatacagtggaagatctgctcaagtacttcaa tccagagtcatggcaagaagatcttgagaatatgtatctggacacccctcggtatcgaggcaggtcataccatgaccg gaagtcaaaagttgacctggataggctcaatgatgatgccaagcgttacagttgcactcccaggaattactcggtcaa tataagagaagagctgaagttggccaatgtggtcttctttccacgttgcctcctcgtgcagcgctgtggaggaaattg tggctgtggaactgtcaactggaggtcctgcacatgcaattcagggaaaaccgtgaaaaagtatcatgasgtattaca gtttgagcctggccacatcaagaggagggtagagctaagaccatggctctagttgacatccagttggatcaccatga acgatgcgattgtatctgcagctcaagaccacctcgataagagaatgtgcacatccttacattaagcctgaaagaacc tttagtttaaggagggtgagataagagacccttttcctaccagcaaccaaacttactactagcctgcaatgcaatgaa cacaagtggttgctgagtctcagccttgctttgttaatgccatggcaagtagaaaggtatatcatcaacttctatacc taagaatataggattgcatttaataatagtgtttgaggttatatatgcacaaacacacacagaaatatattcatgtct atgtgtatatagatcaaatgttttttttggtatatataaccaggtacaccagagcttacatatgtttgagttagactc ttaaaatcctttgccaaaataagggatggtcaaatatatgaaacatgtcttagaaaatttaggagataaatttatt ttaaattttgaaacacaaaacaattttgaatcttgctctcttaaagaaagcatcttgtatattaaaaatcaaaagatg aggctttcttacatatacatcttagttgattattaaaaaaggaaaaaggtttccagagaaaaggccaatacctaagca -continued
tttttttccatgagaagcactgcatacttacctatgtggactgtaataacctgtctccaaaaccatgccataataat aagtgctttagaaattaaatcattgtgttttttatgcatttttgctgaggcatccttattcatttaacacctatctcaa aaacttacttagaaggttttttattatagtcctacaaaagacaatgtataagctgtaacagaattttgaattgttttt ctttgcaaaaccccctccacaaaagcaaatcctttcaagaatggcatgggcattctgtatgaacctttccagatggtgt tcagtgaaagatgtgggtagttgagaacttaaaaagtgaacattgaaacatcgacgtaactggaaaccg The amino acid sequences of human PDGF-A, PDGF-B, PDGF-C and PDGF-D are represented below:

PDGF-A (GenBank entry # NM_002607)
(SEQ ID NO:5)
MRTLACLLLLGCGYLAHVLAEEAEIPREVIERLARSQIHSIRDLQRLLEIDSVGSEDSLDTSLRAHGVHATKHVPEKR

PLPIRRKRSTEEAVPAVCKTRTVIYEIPRSQVDPTSANFLIWPPCVEVKRCTGCCNTSSVKCQPSRVHHRSVKVAKVE

YVRKKPKLKEVQVRLEEHLECACATTSLNPDYREEDTGRPRESGKKRKRKRLKPT

PDGF-B (GenBank entry # NM_002608)
(SEQ ID NO:6)
MNRCWALFLSLCCYLRLVSAEGDPIPEELYEMLSDHSIRSFDDLQRLLHGDPGEEDGAELDLNMTRSHSGGELESLAR

GRRSLGSLTIAEPAMIAECKTRTEVFEISRRLIDRTNANFLVWPPCVEVQRCSGCCNNRNVQCRPTQVQLRPVQVRKI

EIVRKKPIFKKATVTLEDHLACKCETVAAARPVTRSPGGSQEQRAKTPQTRVTIRTVRVRRPPKGKHRKFKHTHDKTA

LKETLGA

PDGF-C (GenBank entry # AF260738)
(SEQ ID NO:7)
MSLFGLLLLTSALAGQRQGTQAESNLSSKFQFSSNKEQNGVQDPQHERIITVSTNGSIHSPRFPHTYPRNTVLVWRLV

AVEENVWIQLTFDERFGLEDPEDDICKYDFVEVEEPSDGTILGRWCGSGTVPGKQISKGNQIRIRFVSDEYFPSEPGF

CIHYNIVMPQFTEAVSPSVLPPSALPLDLLNNAITAFSTLEDLIRYLEPERWQLDLEDLYRPTWQLLGKAFVFGRKSR

VVDLNLLTEEVRLYSCTPRNFSVSIREELKRTDTIFWPGCLLVKRCGGNCACCLHNCNECQCVPSKVTKKYHEVLQLR

PKTGVRGLHKSLTDVALEHHEECDCVCRGSTGG

PDGF-D (GenBank entry # AF336376)
(GSEQ ID NO:8)
MHRLIFVYTLICANFCSCRDTSATPQSASIKALRNANLRRDESNHLTDLYRRDETIQVKGNGYVQSPRFPNSYPRNLL

LTWRLHSQENTRIQLVFDNQFGLEEAENDICRYDFVEVEDISETSTIIRGRWCGHKEVPPRIKSRTNQIKITFKSDDY

FVAKPGFKIYYSLLEDFQPAAASETNWESVTSSISGVSYNSPSVTDPTLIADALDKKIAEFDTVEDLLKYFHPESWQE

DLENMYLDTPRYRGRSYHDRKSKVDLDRLNDDAKRYSCTPRNYSVNIREELKLANVVFFPRCLLVQRCGGNCGCGTVN

WRSCTCNSGKTVKKYHEVLQFEPGHIKRRGRAKTMALVDIQLDHHERCDCICSSRPPR

VEGF Receptors and Their Ligands

The growth of new blood vessels from existing endothelium (angiogenesis) is tightly controlled in healthy adults by opposing effects of positive and negative regulators. Under certain pathological conditions, including proliferative retinopathies, rheumatoid arthritis, psoriasis and cancer, positive regulators prevail and angiogenesis contributes to disease progression (reviewed in Folkman (1995) Nature Medicine 1:27-31). In cancer, the notion that angiogenesis represents the rate limiting step of tumor growth and metastasis (Folkman (1971) New Engl. J. Med. 285:1182-1186) is now supported by considerable experimental evidence (reviewed in Aznavoorian et al. (1993) Cancer 71:1368-1383; Fidler and Ellis (1994) Cell 79:185-188; Folkman (1990) J. Natl. Cancer Inst. 82:4-6).

A number of angiogenic growth factors have been described to date among which vascular endothelial growth factor (VEGF) appears to play a key role as a positive regulator of physiological and pathological angiogenesis (reviewed in Brown et al. (1996) Control of Angiogenesis (Goldberg and Rosen, eds.) Birkhauser, Basel, in press; Thomas (1996) J. Biol. Chem. 271:603-606). VEGF is a secreted disulfide-linked homodimer that selectively stimulates endothelial cells to proliferate, migrate, and produce matrix-degrading enzymes (Conn et al. (1990) Proc. Natl. Acad. Sci. USA 87:1323-1327); Ferrara and Henzel (1989) Biochem. Biophys. Res. Commun. 161:851-858); Gospodarowicz et al. (1989) Proc. Natl. Acad. Sci. USA 7311-7315); Pepper et al. (1 991) Biochem. Biophys. Res. Commun. 181:902-906; Unemori et al. (1992) J. Cell. Physiol. 153:557-562), all of which are processes required for the formation of new vessels. In addition to being the only known endothelial cell specific mitogen, VEGF is unique among angiogenic growth factors in its ability to induce a transient increase in blood vessel permeability to macromolecules (hence its original and alternative name, vascular permeability factor, VPF) (Dvorak et al. (1979) J. Immunol. 122:166-174; Senger et al. (1983) Science 219:983-985; Senger et al. (1986) Cancer Res. 46:5629-5632). Increased vascular permeability and the resulting deposition of plasma proteins in the extravascular space assists the new vessel formation by providing a provisional matrix for the migration of endothelial cells (Dvorak et al. (1995) Am. J. Pathol. 146:1029-1039). Hyperpermeability is indeed a characteristic feature of new vessels, including those associated with tumors (Dvorak et al. (1995) Am. J. Pathol. 146:1029-1039). Furthermore, compensatory angiogenesis induced by tissue hypoxia is also now known to be mediated by VEGF (Levy et al. (1996) J. Biol. Chem. 2746-2753); Shweiki et al. (1992) Nature 359:843-845).

VEGF occurs in four forms (VEGF-121, VEGF-165, VEGF-189, VEGF-206) as a result of alternative splicing of the VEGF gene (Houck et al. (1991) Mol. Endocrin. 5:1806-1814; Tischer et al. (1991) J. Biol. Chem. 266:11947-11954). The two smaller forms are diffusable while the larger two forms remain predominantly localized to the cell membrane as a consequence of their high affinity for heparin. VEGF-165 also binds to heparin and is the most abundant form. VEGF-121, the only form that does not bind to heparin, appears to have a lower affinity for the receptors (Gitay-Goren et al. (1996) J. Biol. Chem. 271:5519-5523) as well as lower mitogenic potency (Keyt et al. (1996) J. Biol. Chem. 271:7788-7795). $VEGF_{165}$ is the most predominant protein, but transcripts of $VEGF_{121}$ may be more abundant. $VEGF_{206}$ is rarely expressed and has been detected only in fetal liver. Recently, other splice variants of 145 and 183 aa have also been described. The 165, 189 and 206 aa splice variants have heparin-binding domains, which help anchor them in extracellular matrix and are involved in binding to heparin sulfate and presentation to VEGF receptors. This binding is a key factor for VEGF potency (i.e., the heparin-binding forms are more active). Several other members of the VEGF family have been cloned, including VEGF-B, -C, and -D. Placenta growth factor (PlGF) is also closely related to VEGF-A. VEGF-A, -B, -C, -D, and PlGF are all distantly related to platelet-derived growth factors-A and -B.

Most types of cells, but usually not endothelial cells themselves, secrete VEGF. Currently, three high-affinity tyrosine kinase receptors for VEGF have been identified, of which VEGF receptor (VEGF)-Flk-1/KDR (VEGFR-2) is exclusively expressed in vascular endothelial cells. Vascular endothelial growth factor (VEGF) was originally discovered as an endothelial-specific growth factor. The biological effects of VEGF are mediated by two tyrosine kinase receptors (Flk-1 and Flk-1/KDR) whose expression is highly restricted to cells of endothelial origin (de Vries et al. (1992) Science 255:989-991; Millauer et al. (1993) Cell 72:835-846; Terman et al. (1991) Oncogene 6:519-524). While the expression of both functional receptors is required for high affinity binding, the chemotactic and mitogenic signaling in endothelial cells appears to occur primarily through the KDR receptor (Park et al. (1994) J. Biol. Chem. 269:25646-25654; Seetharam et al. (1995) Oncogene 10:135-147; Waltenberger et al. (1994) J. Biol. Chem. 26988-26995). The importance of VEGF and VEGF receptors for the development of blood vessels has recently been demonstrated in mice lacking a single allele for the VEGF gene (Carmeliet et al. (1996) Nature 380:435-439; Ferrara et al. (1996) Nature 380:439-442) or both alleles of the Flt-1 (Fong et al. (1995) 376:66-70) or Flk-1 genes (Shalaby et al. (1995) Nature 376:62-66). In each case, distinct abnormalities in vessel formation were observed resulting in embryonic lethality.

VEGF is produced and secreted in varying amounts by virtually all tumor cells (Brown et al. (1997) Regulation of Angiogenesis (Goldberg and Rosen, Eds.) Birkhauser, Basel, pp. 233-269). Direct evidence that VEGF and its receptors contribute to tumor growth was recently obtained through a demonstration that the growth of human tumor xenografts in nude mice could be inhibited by neutralizing antibodies to VEGF (Kim et al. (1993) Nature 362:841-844), by the expression of dominant-negative VEGF receptor Flk-1 (Millauer et al. (1996) Cancer Res. 56:1615-1620; Millauer et al. (1994) Nature 367:576-579), by low molecular weight inhibitors of Flk-1 tyrosine kinase activity (Strawn et al. (1966) Cancer Res. 56:3540-3545) or by the expression of antisense sequence to VEGF mRNA (Saleh et al. (1996) Cancer Res. 56:393-401). Importantly, the incidence of tumor metastases was also found to be dramatically reduced by VEGF antagonists (Claffey et al. (1996) Cancer Res. 56:172-181).

In addition to their use as anticancer agents, VEGF inhibitors may be useful in a wide variety of proliferative diseases characterized by excessive angiogenesis, including psoriasis, ocular disorders, collagen vascular diseases and rheumatoid arthritis. Although most tumor types are known to produce VEGF, until recently none has been shown to express functional VEGF receptors.

While the predominant role of this growth factor in the formation of new blood vessels is unquestioned, recent observations indicate that VEGF also has direct effects on neurons and glial cells, and stimulates their growth, survival and axonal outgrowth. Because of these pleiotropic effects, VEGF has now been implicated in several neurological disorders both in the preterm infant (leukomalacia) and the adult (stroke, neurodegeneration, cerebral and spinal trauma, ischemic and diabetic neuropathy, nerve regeneration). It is not known if the effect of VEGF in these disorders relates to its angiogenic activity or direct neurotrophic effect.

It is known that VEGF is involved in the formation of new blood vessels during embryonic development as well as in a variety of pathological conditions. Although VEGF primarily stimulates endothelial cells, it may also act on other cell types. Indeed, VEGF, Flt-1 and Flk-1 have recently been implicated in stroke, spinal cord ischemia and in ischemic and diabetic neuropathy.

The nucleic acid sequence for human VEGF-165 (GenBank # AF486837) is represented below:

```
ATGAACTTTCTGCTGTCTTGGGTGCATTGGAGCCTTGCCTTGCTGCTCTA

CCTCCACCATGCCAAGTGGTCCCAGGCTGCACCCATGGCAGAAGGAGGAG

GGCAGAATCATCACGAAGTGGTGAAGTTCATGGATGTCTATCAGCGCAGC

TACTGCCATCCAATCGAGACCCTGGTGGACATCTTCCAGGAGTACCCTGA

TGAGATCGAGTACATCTTCAAGCCATCCTGTGTGCCCCTGATGCGATGCG

GGGGCTGCTGCAATGACGAGGGCCTGGAGTGTGTCCCCACTGAGGAGTCC

AACATCACCATGCAGATTATGCGGATCAAACCTCACCAAGGCCAGCACAT

AGGAGAGATGAGCTTCCTACAGCACAACAAATGTGAATGCAGACCAAAGA

AAGATAGAGCAAGACAAGAAAATCCCTGTGGGCCTTGCTCAGAGCGGAGA

AAGCATTTGTTTGTACAAGATCCGCAGACGTGTAAATGTTCCTGCAAAAA

CACAGACTCGCGTTGCAAGGCGAGGCAGCTTGAGTTAAACGAACGTACTT

GCAGATGTGACAAGCCGAGGCGGTGA
```

The amino acid sequence for human VEGF-165 (GenBank # AF486837) is represented below:

(SEQ ID NO:3)
MNFLLSWVHWSLALLLYLHHAKWSQAAPMAEGGGQNHHEVVKFMDVYQRS

YCHPIETLVDIFQEYPDEIEYIFKPSCVPLMRCGGCCNDEGLECVPTEES

NITMQIMRTKPHQGQHIGEMSFLQHNKCECRPKKDRARQENPCGPCSERR

KHLFVQDPQTCKCSCKNTDSRCKARQLELNERTCRCDKPRR

This invention demonstrates the functional role of VEGF for neural stem cells in vitro and in vivo. The data indicate a specific localization and function of the VEGF receptor Flk-1 in brain regions with neural stem cell activity. The VEGF-receptor Flk-1 is expressed not only in blood vessels but also in the ependymal zone of the ventricle wall, a region that is currently thought to be a possible origin for neural stem cells. VEGF exerts a strong influence on neural stem cell activity by increasing the generation of new neurons in the hippocampus and the olfactory bulb, when directly applied to the adult rodent brain. Neural stem cell cultures express VEGF as well as its receptor Flk-1, suggesting an autocrine role of VEGF in cultured neural stem cells. Using defined cell culture medium, it is shown that VEGF enhances the expansion of neural stem cells in vitro.

The invention provides a method of activating a receptor on a neural stem cell. The method comprises exposing a neural stem cell expressing a receptor to exogenous reagent, which induces the neural stem cell to proliferate, differentiate or migrate.

This invention can be practiced using stem cells of various types. Neural stem cells and progenitor cells can be obtained from any mammal, as well as fetal or adult tissue. In a preferred embodiment, the mammal is a human. NSCs/NPCs can be derived from central nervous system tissue selected from the group consisting of the hippocampus, ventricle wall, neocortex, cerebellum, septal and striatal parenchymal, basal forebrain, hindbrain, mesencephalon, diencephalon, septum and spinal cord. In a preferred embodiment, the NSC/NPC is derived from the ventricle wall.

Neither the PDGF nor VEGF families are limited to the disclosed nucleic acid and amino acid sequences. Other sequences can be retrieved from GenBank including, for example, the GenBank entry numbers: NM002607, NM033023, M12783, AF486837, AF024710, AK098750, AF022375, NM_003376, M27281, M32977, AY047581, AF430806, X62568, AF091352, AF214570, AB021221, AJ010438, S85192, BC019867, BC011177, AK056914 and AF062645.

Production of Reagents

Reagents for treatment of patients are recombinantly produced, purified and formulated according to well known methods.

Reagents of the invention, and individual moieties or analogs and derivatives thereof, can be chemically synthesized. A variety of protein synthesis methods are common in the art, including synthesis using a peptide synthesizer. See, e.g., *Peptide Chemistry, A Practical Textbook*, Bodasnsky, Ed. Springer-Verlag, 1988; Merrifield, Science 232: 241-247 (1986); Barany, et al, Intl. J. Peptide Protein Res. 30: 705-739 (1987); Kent, Ann. Rev. Biochem. 57:957-989 (1988), and Kaiser, et al, Science 243: 187-198 (1989). The peptides are purified so that they are substantially free of chemical precursors or other chemicals using standard peptide purification techniques. The language "substantially free of chemical precursors or other chemicals" includes preparations of peptide in which the peptide is separated from chemical precursors or other chemicals that are involved in the synthesis of the peptide. In one embodiment, the language "substantially free of chemical precursors or other chemicals" includes preparations of peptide having less than about 30% (by dry weight) of chemical precursors or non-peptide chemicals, more preferably less than about 20% chemical precursors or non-peptide chemicals, still more preferably less than about 10% chemical precursors or non-peptide chemicals, and most preferably less than about 5% chemical precursors or non-peptide chemicals.

Chemical synthesis of peptides facilitates the incorporation of modified or unnatural amino acids, including D-amino acids and other small organic molecules. Replacement of one or more L-amino acids in a peptide with the corresponding D-amino acid isoforms can be used to increase the resistance of peptides to enzymatic hydrolysis, and to enhance one or more properties of biologically active peptides, i.e., receptor binding, functional potency or duration of action. See, e.g., Doherty, et al., 1993. J. Med. Chem. 36: 2585-2594; Kirby, et al., 1993, J. Med. Chem. 36:3802-3808; Morita, et al., 1994, FEBS Lett. 353: 84-88; Wang, et al., 1993 Int. J. Pept. Protein Res. 42: 392-399; Fauchere and Thiunieau, 1992. Adv. Drug Res. 23: 127-159.

Introduction of covalent cross-links into a peptide sequence can conformationally and topographically constrain the peptide backbone. This strategy can be used to develop peptide analogs of reagents with increased potency, selectivity and stability. A number of other methods have been used successfully to introduce conformational constraints into peptide sequences in order to improve their potency, receptor selectivity and biological half-life. These include the use of (i) $C_\alpha$-methylamino acids (see, e.g., Rose, et aL, Adv. Protein Chem. 37: 1-109 (1985); Prasad and Balaram, *CRC Crit. Rev. Biochem.*, 16: 307-348 (1984)); (ii) $N_\alpha$-methylamino acids (see, e.g., Aubry, et al., Int. J. Pept. Protein Res., 18: 195-202 (1981); Manavalan and Momany, Biopolymers, 19: 1943-1973 (1980)); and (iii) α,β-unsaturated amino acids (see, e.g., Bach and Gierasch, Biopolymers, 25: 5175-S192 (1986); Singh, et al., Biopolymers, 26: 819-829 (1987)). These and many other amino acid analogs are commercially available, or can be easily prepared. Additionally, replacement of the C-terminal acid with an amide can be used to enhance the solubility and clearance of a peptide.

Alternatively, a reagent may be obtained by methods well-known in the art for recombinant peptide expression and purification. A DNA molecule encoding the protein reagent can be generated. The DNA sequence is known or can be deduced from the protein sequence based on known codon usage. See, e.g., Old and Primrose, *Principles of Gene Manipulation* $3^{rd}$ ed., Blackwell Scientific Publications, 1985; Wada et al., Nucleic Acids Res. 20: 2111-2118(1992). Preferably, the DNA molecule includes additional sequence, e.g., recognition sites for restriction enzymes which facilitate its cloning into a suitable cloning vector, such as a plasmid. Nucleic acids may be DNA, RNA, or a combination thereof. Nucleic acids encoding the reagent may be obtained by any method known within the art (e.g., by PCR amplification using synthetic primers hybridizable to the 3'- and 5'-termini of the sequence and/or by cloning from a cDNA or genomic library using an oligonucleotide sequence specific for the given gene sequence, or the like). Nucleic acids can also be generated by chemical synthesis.

Any of the methodologies known within the relevant art regarding the insertion of nucleic acid fragments into a vector may be used to construct expression vectors that contain a chimeric gene comprised of the appropriate transcriptional/ translational control signals and reagent-coding sequences. Promoter/enhancer sequences within expression vectors may use plant, animal, insect, or fungus regulatory sequences, as provided in the invention.

A host cell can be any prokaryotic or eukaryotic cell. For example, the peptide can be expressed in bacterial cells such as *E. coli*, insect cells, fungi or mammalian cells (such as Chinese hamster ovary cells (CHO) or COS cells). Other suitable host cells are known to those skilled in the art. In one embodiment, a nucleic acid encoding a reagent is expressed in mammalian cells using a mammalian expression vector. Examples of mammalian expression vectors include pCDM8 (Seed (1987) Nature 329:840) and pMT2PC (Kaufman et al. (1987) EMBO J 6: 187-195). Furthermore, transgenic animals containing nucleic acids that encode PDGF may also be used to express peptides of the invention.

The host cells, can be used to produce (i.e., overexpress) peptide in culture. Accordingly, the invention further provides methods for producing the peptide using the host cells of the invention. In one embodiment, the method comprises culturing the host cell of invention (into which a recombinant expression vector encoding the peptide has been introduced) in a suitable medium such that peptide is produced. The method further involves isolating peptide from the medium or the host cell. Ausubel et al., (Eds). In: *Current Protocols in Molecular Biology*. J. Wiley and Sons, New York, N.Y. 1998.

An "isolated" or "purified" recombinant peptide or biologically active portion thereof is substantially free of cellular material or other contaminating proteins from the cell or tissue source from which the peptide of interest is derived. The language "substantially free of cellular material" includes preparations in which the peptide is separated from cellular components of the cells from which it is isolated or recombinantly produced. In one embodiment, the language "substantially free of cellular material" includes preparations of peptide having less than about 30% (by dry weight) of peptide other than the desired peptide (also referred to herein as a "contaminating protein"), more preferably less than about 20% of contaminating protein, still more preferably less than about 10% of contaminating protein, and most preferably less than about 5% contaminating protein. When the peptide or biologically active portion thereof is recombinantly produced, it is also preferably substantially free of culture medium, i.e., culture medium represents less than about 20%, more preferably less than about 10%, and most preferably less than about 5% of the volume of the peptide preparation.

The invention also pertains to variants of a reagent that function as either agonists (mimetics) or as antagonists. Variants of a reagent can be generated by mutagenesis, e.g., discrete point mutations. An agonist of a reagent can retain substantially the same, or a subset of, the biological activities of the naturally occurring form of the reagent. An antagonist of the reagent can inhibit one or more of the activities of the naturally occurring form of the reagent by, for example, competitively binding to the receptor. Thus, specific biological effects can be elicited by treatment with a variant with a limited function. In one embodiment, treatment of a subject with a variant having a subset of the biological activities of the naturally occurring form of the reagent has fewer side effects in a subject relative to treatment with the naturally occurring form of the reagent.

Preferably, the analog, variant, or derivative reagent is functionally active. As utilized herein, the term "functionally active" refers to species displaying one or more known functional attributes of a full-length reagent. "Variant" refers to a reagent differing from naturally occurring reagent, but retaining essential properties thereof. Generally, variants are overall closely similar, and in many regions, identical to the naturally occurring reagent.

Variants of the reagent that function as either agonists (mimetics) or as antagonists can be identified by screening combinatorial libraries of mutants of the reagent for peptide agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential sequences is expressible as individual peptides, or alternatively, as a set of larger fusion proteins (e.g., for phage display) containing the set of sequences therein. There are a variety of methods which can be used to produce libraries of potential variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential sequences. Methods for synthesizing degenerate oligonucleotides are known in the art (see, e.g., Narang (1983) Tetrahedron 39:3; Itakura et al. (1984) Annu Rev Biochem 53:323; Itakura et al. (1984) Science 198:1056; Ike et al. (1983) Nucl. Acids Res. 11:477.

Derivatives and analogs of the reagent or individual moieties can be produced by various methods known within the art. For example, the polypeptide sequences may be modified by any number of methods known within the art. See e.g., Sambrook, et al., 1990. *Molecular Cloning: A Laboratory Manual*, 2nd ed., (Cold Spring Harbor Laboratory Press; Cold Spring Harbor, N.Y.). Modifications include: glycosylation, acetylation, phosphorylation, amidation, derivatization by known protecting/blocking groups, linkage to an antibody molecule or other cellular reagent, and the like. Any of the numerous chemical modification methodologies known within the art may be utilized including, but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

Derivatives and analogs may be full length or other than full length, if said derivative or analog contains a modified nucleic acid or amino acid, as described infra. Derivatives or analogs of the reagent include, but are not limited to, molecules comprising regions that are substantially homologous in various embodiments, of at least 30%, 40%, 50%, 60%, 70%, 80%, 90% or preferably 95% amino acid identity when: (i) compared to an amino acid sequence of identical size; (ii) compared to an aligned sequence in that the alignment is done by a computer homology program known within the art (e.g., Wisconsin GCG software) or (iii) the encoding nucleic acid is capable of hybridizing to a sequence encoding the aforementioned peptides under stringent (preferred), moderately stringent, or non-stringent conditions. See, e.g., Ausubel, et al., *Current Protocols in Molecular Biology*, John Wiley and Sons, New York, N.Y., 1993.

Derivatives of the reagent may be produced by alteration of their sequences by substitutions, additions or deletions that result in functionally-equivalent molecules. One or more amino acid residues within the reagent may be substituted by another amino acid of a similar polarity and net charge, thus resulting in a silent alteration. Conservative substitutes for an amino acid within the sequence may be selected from other members of the class to which the amino acid belongs. For example, nonpolar (hydrophobic) amino acids include alanine, leucine, isoleucine, valine, proline, phenylalanine, tryptophan and methionine. Polar neutral amino acids include glycine, serine, threonine, cysteine, tyrosine, asparagine, and glutamine. Positively charged (basic) amino acids include arginine, lysine and histidine. Negatively charged (acidic) amino acids include aspartic acid and glutamic acid.

The reagent can be administered locally to any loci implicated in the CNS disorder pathology, i.e. any loci deficient in neural cells as a cause of the disease. For example, the reagent can be administered locally to the ventricle of the brain, substantia nigra, striatum, locus ceruleous, nucleus basalis Meynert, pedunculopontine nucleus, cerebral cortex, and spinal cord.

Neural stem cells and their progeny can be induced to proliferate and differentiate in vivo by administering to the host a reagent, alone or in combination with other agents, or by administering a pharmaceutical composition containing the reagent that will induce proliferation and differentiation of the cells. Pharmaceutical compositions include any substance that blocks the inhibitory influence and/or stimulates neural stem cells and stem cell progeny to proliferate and ultimately differentiate. Such in vivo manipulation and modification of these cells allows. cells lost, due to injury or disease, to be endogenously replaced, thus obviating the need for transplanting foreign cells into a patient.

Antibodies

Included in the invention are antibodies to be used as reagents. The term "antibody" as used herein refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and an $F_{ab}$ expression library. In general, antibody molecules obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

An isolated protein of the invention intended to serve as an antigen, or a portion or fragment thereof, can be used as an immunogen to generate antibodies that immunospecifically bind the antigen, using standard techniques for polyclonal and monoclonal antibody preparation. The full-length protein can be used or, alternatively, the invention provides antigenic peptide fragments of the antigen for use as immunogens. An antigenic peptide fragment comprises at least 6 amino acid residues of the amino acid sequence of the full length protein and encompasses an epitope thereof such that an antibody raised against the peptide forms a specific immune complex with the full length protein or with any fragment that contains the epitope. Preferably, the antigenic peptide comprises at least 10 amino acid residues, or at least 15 amino acid residues, or at least 20 amino acid residues, or at least 30 amino acid residues. Preferred epitopes encompassed by the antigenic peptide are regions of the protein that are located on its surface; commonly these are hydrophilic regions.

In certain embodiments of the invention, at least one epitope encompassed by the antigenic peptide is a region of PDGF, VEGF or a PDGF or VEGF receptor that is located on the surface of the protein, e.g., a hydrophilic region. A hydrophobicity analysis of the human those protein sequences will indicate which regions of the polypeptide are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, *Proc. Nat. Acad. Sci. USA* 78: 3824-3828; Kyte and Doolittle 1982, *J Mol. Biol.* 157: 105-142, each incorporated herein by reference in their entirety. Antibodies that are specific for one or more domains within an antigenic protein, or derivatives, fragments, analogs or homologs thereof, are also provided herein.

The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. A PDGF or VEGF ligand or receptor polypeptide or a fragment thereof comprises at least one antigenic epitope. An anti-PDGF or VEGF antibody of the present invention is said to specifically bind to the antigen when the equilibrium binding constant ($K_D$) is $\leq 1$ µM, preferably $\leq 100$ nM, more preferably $\leq 10$ nM, and most preferably $\leq 100$ pM to about 1 pM, as measured by assays such as radioligand binding assays or similar assays known to those skilled in the art.

Various procedures known within the art may be used for the production of polyclonal or monoclonal antibodies directed against a protein of the invention, or against derivatives, fragments, analogs homologs or orthologs thereof (see, for example, Antibodies: A Laboratory Manual, Harlow E, and Lane D, 1988, Cold Spring Harbor Laboratory Press, Cold Spring Harbor, N.Y., incorporated herein by reference). Some of these antibodies are discussed below.

Polyclonal Antibodies

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), adjuvants usable in humans such as Bacille Calmette-Guerin and *Corynebacterium parvum*, or similar immunostimulatory agents. Additional examples of adjuvants which can be employed include MPL-TDM adjuvant (monophosphoryl Lipid A, synthetic trehalose dicorynomycolate).

The polyclonal antibody molecules directed against the immunogenic protein can be isolated from the mammal (e.g., from the blood) and further purified by well known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

Monoclonal Antibodies

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen binding site capable of immunoreacting with a particular epitope of the antigen characterized by a unique binding affinity for it.

Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). It is an objective, especially important in therapeutic applications of monoclonal antibodies, to identify antibodies having a high degree of specificity and a high binding affinity for the target antigen.

After the desired hybridoma cells are identified, the clones can be subcloned by limiting dilution procedures and grown by standard methods (Goding, 1986). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Humanized Antibodies

The antibodies directed against the protein antigens of the invention can further comprise humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin and contain minimal sequence derived from a non-human immunoglobulin. Humanization can be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. (See also U.S. Pat. No. 5,225,539.) In some instances, Fv framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; and Presta, Curr. Op. Struct. Biol., 2:593-596 (1992)).

Human Antibodies

Fully human antibodies essentially relate to antibody molecules in which the entire sequence of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized in the practice of the present invention and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries (Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (Bio/Technology 10, 779-783 (1992)); Lonberg et al. (Nature 368 856-859 (1994)); Morrison (Nature 368, 812-13 (1994)); Fishwild et al, (Nature Biotechnology 14, 845-51 (1996)); Neuberger (Nature Biotechnology 14, 826 (1996)); and Lonberg and Huszar (Intern. Rev. Immunol. 13 65-93 (1995)).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

$F_{ab}$ Fragments and Single Chain Antibodies

According to the invention, techniques can be adapted for the production of single-chain antibodies specific to an antigenic protein of the invention (see e.g., U.S. Pat. No. 4,946, 778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit. Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from E. coli and chemically coupled to form bispecific antibodies. Shalaby et al., J. Exp. Med. 175:217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994). Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA or TETA. Another bispecific antibody of interest binds the protein antigen described herein and further binds tissue factor (TF).

Immunoliposomes

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Antibody Therapeutics

Antibodies of the invention, including polyclonal, monoclonal, humanized and fully human antibodies, may used as therapeutic agents such as one of this invention. Such agents will generally be employed to treat or prevent a disease or pathology, specifically neurological disease, in a subject. An antibody preparation, preferably one having high specificity and high affinity for its target antigen, is administered to the subject and will generally have an effect due to its binding with the target. Such an effect may be one of two kinds, depending on the specific nature of the interaction between the given antibody molecule and the target antigen in question. In the first instance, administration of the antibody may abrogate or inhibit the binding of the target with an endogenous PDGF or VEGF ligand to which it naturally binds. In this case, the antibody binds to the target and masks a binding site of the naturally occurring ligand, wherein the ligand serves as an effector molecule. Thus, the receptor mediates a signal transduction pathway for which ligand is responsible.

Alternatively, the effect may be one in which the antibody elicits a physiological result by virtue of binding to an effector binding site on the target molecule. In this case the target, a PDGF or VEGF receptor having an endogenous ligand which needs to be modulated, binds the antibody as a surrogate effector ligand, initiating a receptor-based signal transduction event by the receptor.

A therapeutically effective amount of an antibody of the invention relates generally to the amount needed to achieve a therapeutic objective. As noted above, this may be a binding interaction between the antibody and its target antigen that, in certain cases, interferes with the functioning of the target, and in other cases, promotes a physiological response. The amount required to be administered will furthermore depend on the binding affinity of the antibody for its specific antigen and the rate at which an administered antibody is depleted from the free volume of the subject to which it is administered.

Diseases and Disorders

Diseases and disorders that are characterized by altered (relative to a subject not suffering from the disease or disorder) levels or biological activity may be treated with therapeutics that antagonize (i.e., reduce or inhibit) or activate PDGF or VEGF activity. Therapeutics that antagonize activity may be administered in a therapeutic or prophylactic manner. Therapeutics that may be utilized include, but are not limited to: (i) an aforementioned peptide, analog, derivatives, fragments or homologs thereof; (ii) antibodies to an aforementioned peptide; (iii) nucleic acids encoding an aforementioned peptide; (iv) administration of antisense nucleic acid and nucleic acids that are "dysfunctional" (i.e., due to a heterologous insertion within the coding sequences of coding sequences to an aforementioned peptide) that are utilized to "knockout" endogenous function of an aforementioned peptide by homologous recombination (see, e.g., Capecchi, 1989. *Science* 244:1288-1292); or (v) modulators (i.e., inhibitors, agonists and antagonists, including additional peptide mimetic of the invention or antibodies specific to a peptide of the invention) that alter the interaction between an aforementioned peptide and its binding partner.

Diseases and disorders that are characterized by altered (relative to a subject not suffering from the disease or disorder) levels or biological activity may be treated with therapeutics that increase (i.e., are agonists to) activity. Therapeutics that upregulate activity may be administered in a therapeutic or prophylactic manner. Therapeutics that may be utilized include, but are not limited to, an aforementioned peptide, analog, derivatives, fragments or homologs thereof; or an agonist that increases bioavailability.

Increased or decreased levels can be detected by quantifying peptide and/or RNA, by obtaining a patient tissue sample (e.g., from biopsy tissue) and assaying it in vitro for RNA or peptide levels, structure and/or activity of the expressed peptides (or mRNAs of an aforementioned peptide). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, and the like).

Therapeutic Methods

Another aspect of the invention pertains to methods of modulating PDGF and VEGF expression or activity for therapeutic purposes. The modulatory method of the invention involves contacting a cell with an agent that modulates one or more of the activities of PDGF and/or VEGF protein activity associated with the cell. An agent that modulates this protein activity can be an agent as described herein, such as a nucleic acid or a protein, a naturally-occurring cognate ligand of a PDGF or VEGF receptor, a peptide, a PDGF or VEGF peptidomimetic, or other small molecule. In one embodiment, the agent stimulates the activity of the PDGF or VEGF signalling pathway. Examples of such stimulatory agents include active PDGF and VEGF protein and a nucleic acid molecule encoding PDGF or VEGF that has been introduced into the cell. In another embodiment, the agent inhibits PDGF or VEGF signaling. Examples of such inhibitory agents include antisense nucleic acid molecules and antibodies. These modulatory methods can be performed in vitro (e.g., by culturing the cell with the agent) or, alternatively, in vivo (e.g., by administering the agent to a subject). As such, the invention provides methods of treating an individual afflicted with a disease or disorder, specifically a neurological disorder. In one embodiment, the method involves administering an reagent (e.g., an reagent identified by a screening assay described herein), or combination of reagents that modulate (e.g., up-regulates or down-regulates) PDGF and VEGF expression or activity. In another embodiment, the method involves administering a PDGF and VEGF protein or nucleic acid molecule as therapy to modulate proliferation, differentiation or survival of NSCs/NPCs.

Stimulation of PDGF or VEGF activity is desirable in situations in which PDGF and/or VEGF are abnormally downregulated and/or in which increased PDGF or VEGF activity is likely to have a beneficial effect. One example of such a situation is where a subject has a disorder characterized by aberrant cell proliferation and/or differentiation (e.g., Parkinson's disease and Alzheimer's disease). As shown in Example 5, PDGF-BB can counteract the MPTP-induced neuronal loss similar to that seen in Parkinson's disease.

Determination of the Biological Effect of the Therapeutic

In various embodiments of the invention, suitable in vitro or in vivo assays are performed to determine the effect of a specific therapeutic and whether its administration is indicated for treatment of the affected tissue.

In various specific embodiments, in vitro assays may be performed with representative stem cells or newly differentiated cells involved in the patient's disorder, to determine if a given therapeutic exerts the desired effect upon the cell type(s). Compounds for use in therapy may be tested in suitable animal model systems including, but not limited to rats, mice, chicken, cows, monkeys, rabbits, and the like, prior to testing in human subjects. Similarly, for in vivo testing, any of the animal model system known in the art may be used prior to administration to human subjects.

Pharmaceutical Compositions

The invention provides methods of influencing central nervous system cells to produce progeny that can replace damaged or missing neurons in the central nervous system by exposing a patient, suffering from a neurological disease or disorder, to a reagent (e.g. PDGF, VEGF) in a suitable formulation through a suitable route of administration, that modulates NSC or NPC activity in vivo. A "neurological disease or disorder" is a disease or disorder which results in the disturbance in the structure or function of the central nervous system resulting from developmental abnormality, disease, injury or toxin. Examples of neurological diseases or disorders include neurodegenerative disorders (e.g. associated with Parkinson's disease, Alzheimer's disease, Huntington's disease, Shy-Drager Syndrome, Progressive Supranuclear Palsy, Lewy Body Disease or Amyotrophic Lateral Sclerosis); ischemic disorders (e.g. cerebral or spinal cord infarction and ischemia, stroke); traumas (e.g. caused by physical injury or surgery, and compression injuries; affective disorders (e.g. stress, depression and post-traumatic depression); neuropsychiatric disorders (e.g. schizophrenia, multiple sclerosis or epilepsy); and learning and memory disorders.

This invention provides a method of treating a neurological disease or disorder comprising administering a reagent that modulates neural stem cell or neural progenitor cell activity in vivo to a mammal. The term "mammal" refers to any mammal classified as a mammal, including humans, cows, horses, dogs, sheep and cats. In one embodiment, the mammal is a human.

The invention provides a regenerative cure for neurodegenerative diseases by stimulating ependymal cells and subventricular zone cells to proliferate, migrate and differentiate into the desired neural phenotype targeting loci where cells are damaged or missing. In vivo stimulation of ependymal stem cells is accomplished by locally administering a reagent to the cells in an appropriate formulation. By increasing neurogenesis, damaged or missing neurons can be replaced in order to enhance brain function in diseased states.

A pharmaceutical composition useful as a therapeutic agent for the treatment of central nervous system disorders is provided. For example, the composition includes a reagent of the invention, which can be administered alone or in combination with the systemic or local co-administration of one or more additional agents. Such agents include preservatives, ventricle wall permeability increasing factors, stem cell mitogens, survival factors, glial lineage preventing agents, anti-apoptotic agents, anti-stress medications, neuroprotectants, and anti-pyrogenics. The pharmaceutical composition preferentially treats CNS diseases by stimulating cells (e.g., ependymal cells and subventricular zone cells) to proliferate, migrate and differentiate into the desired neural phenotype, targeting loci where cells are damaged or missing.

A method for treating a subject suffering from a CNS disease or disorder is also provided. This method comprises administering to the subject an effective amount of a pharmaceutical composition containing a reagent (I) alone in a dosage range of 0.5 ng/kg/day to 500 ng/kg/day, (2) in a combination with a ventricle wall permeability increasing factor, or (3) in combination with a locally or systemically co-administered agent.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., chimeric peptide) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Nucleic acid molecules encoding a proteinaceous agent can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) PNAS 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

In another embodiments, the reagent is administered in a composition comprising at least 90% pure reagent. The reagent can be, for example, heterodimers or homodimers of PDGF-A, PDGF-B, PDGF-AA, PDGF-BB, PDGF-AB, VEGF-A, VEGF-B, VEGF-C, VEGF-D or a PDGF or VEGF receptor, or any combination thereof.

Preferably the reagent is formulated in a medium providing maximum stability and the least formulation-related side-effects. In addition to the reagent, the composition of the invention will typically include one or more protein carrier, buffer, isotonic salt and stabilizer.

In some instances, the reagent can be administered by a surgical procedure implanting a catheter coupled to a pump device. The pump device can also be implanted or be extracorporally positioned. Administration of the reagent can be in intermittent pulses or as a continuous infusion. Devices for injection to discrete areas of the brain are known in the art (see, e.g., U.S. Pat. Nos. 6,042,579; 5,832,932; and 4,692,147).

Reagents containing compositions can be administered in any conventional form for administration of a protein. A reagent can be administered in any manner known in the art in which it may either pass through or by-pass the blood-brain barrier. Methods for allowing factors to pass through the blood-brain barrier include minimizing the size of the factor, providing hydrophobic factors which may pass through more easily, conjugating the protein reagent or other agent to a carrier molecule that has a substantial permeability coefficient across the blood brain barrier (see, e.g., U.S. Pat. No. 5,670,477).

Reagents, derivatives, and co-administered agents can be incorporated into pharmaceutical compositions suitable for administration. Such compositions typically comprise the agent and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Modifications can be made to the agents to affect solubility or clearance of the peptide. Peptidic molecules may also be synthesized with D-amino acids to increase resistance to enzymatic degradation. In some cases, the composition can be co-administered with one or more solubilizing agents, preservatives, and permeation enhancing agents.

For example, the composition can include a preservative or a carrier such as proteins, carbohydrates, and compounds to increase the density of the pharmaceutical composition. The composition can also include isotonic salts and redox-control agents.

In some embodiments, the composition administered includes the reagent and one or more agents that increase the permeability of the ventricle wall, i.e. "ventricle wall permeability enhancers." Such a composition can help an injected composition penetrate deeper than the ventricle wall. Examples of suitable ventricle wall permeability enhancers include, for example, liposomes, VEGF (vascular endothelial growth factor), IL-s, TNFα, polyoxyethylene, polyoxyethylene ethers of fatty acids, sorbitan monooleate, sorbitan monolaurate, polyoxyethylene monolaurate, polyoxyethylene sorbitan monolaurate, fusidic acid and derivatives thereof, EDTA, disodium EDTA, cholic acid and derivatives, deoxycholic acid, glycocholic acid, glycodeoxycholic acid, taurocholic acid, taurodeoxycholic acid, sodium cholate, sodium glycocholate, glycocholate, sodium deoxycholate, sodium taurocholate, sodium glycodeoxycholate, sodium taurodeoxycholate, chenodeoxycholic acid, urosdeoxycholic acid, saponins, glycyrrhizic acid, ammonium glycyrrhizide, decamethonium, decamethonium bromide, dodecyltrimethylammonium bromide, and dimethyl-β-cyclodextrin or other cyclodextrins.

Drug Screening

The invention also provide a method of using the receptors or receptor/reagent complexes for analyzing or purifying certain stem or progenitor cell populations, using e.g. antibodies, against the receptors or receptor/reagent complexes.

In another aspect, the invention provides a method for screening for reagents that influence stem and progenitor cells. In some applications, neural cells (undifferentiated or differentiated) are used to screen factors that promote maturation into neural cells, or promote proliferation and maintenance of such cells in long-term culture. For example, candidate reagents are tested by adding them to cells in culture at varying dosages, and then determining any changes that result, according to desirable criteria for further culture and use of the cells. Physical characteristics of the cells can be analyzed by observing cell and neurite growth with microscopy. The induction of expression of increased levels of proliferation, differentiation and migration can be analyzed with any technique known in the art which can identify proliferation and differentiation. Such techniques include RT-PCR, in situ hybridisation, and ELISA.

In one aspect, novel receptor/reagents in undifferentiated neurospheres was examined using RT-PCR techniques. In particular, genes that are up-regulated in these undifferentiated neurospheres were identified. As used herein, the term "up-regulation" refers to a process that increases reagent/receptor interactions due to an increase in the number of available receptors. The presence of these genes suggests a potential role in the mediation of signal transduction pathways in the regulation of NSC/NPC function. Furthermore, by knowing the levels of expression of the receptors or their various reagents, it is possible to diagnose disease or determine the role of stem and progenitor cells in the disease. By analyzing the genetic or amino-acid sequence variations in these genes or gene products, it is possible to diagnose or predict the development of certain diseases. Such analysis will provide the necessary information to determine the usefulness of using stem or progenitor cell based treatments for disease.

In another aspect, in situ hybridization is performed on adult mouse brain sections to determine which cells in the adult brain express these signalling pathways. This data is helpful in determining treatment options for various neurological diseases.

In yet another aspect, quantitative PCR is performed on RNA prepared from undifferentiated and differentiated neurospheres In some embodiments, certain receptor-reagent combinations reveal much higher expression in the undifferentiated neurospheres as compared to neurospheres that have been induced to differentiate, while in other embodiments, other receptor-reagent combinations reveal the opposite. Undifferentiated neurospheres (which are rapidly proliferating cells with the capacity to differentiate into neurons and glial cells, which express higher levels of these receptor-reagent combinations) are involved in the pathways of proliferation and differentiation of NSC/NPC. For certain signalling pathways, the data indicating that they are expressed more in differentiated neurospheres suggests a role for this receptor-reagent combination in cells embarking or proceeding on a differentiation pathway.

To determine the effect of a potential reagent on neural cells, a culture of NSCs/NPCs derived from multipotent stem cells can be obtained from normal neural tissue or, alternatively, from a host afflicted with a CNS disease or disorder. The choice of culture will depend upon the particular agent being tested and the effects one wishes to achieve. Once the cells are obtained from the desired donor tissue, they are proliferated in vitro in the presence of a proliferation-inducing reagent.

The ability of various biological agents to increase, decrease or modify in some other way the number and nature of the stem cell progeny proliferated in the presence of the proliferative factor can be screened on cells proliferated by the methods previously discussed. For example, it is possible to screen for reagents that increase or decrease the proliferative ability of NSCs/NPCs which would be useful for generating large numbers of cells for transplantable purposes. In these studies precursor cells are plated in the presence of the reagent in question and assayed for the degree of proliferation and survival or progenitor cells and their progeny can be determined. It is possible to screen neural cells which have already been induced to differentiate prior to the screening. It is also possible to determine the effects of the reagent on the differentiation process by applying them to precursors cells prior to differentiation. Generally, the reagent will be solubilized and added to the culture medium at varying concentrations to determine the effect of the agent at each dose. The culture medium may be replenished with the reagent every couple of days in amounts so as to keep the concentration of the reagent somewhat constant.

Changes in proliferation are observed by an increase or decrease in the number of neurospheres that form and/or an increase or decrease in the size of the neurospheres, which is a reflection of the rate of proliferation and is determined by the numbers of precursor cells per neurosphere.

Using these screening methods, it is possible to screen for potential drug side-effects on prenatal and postnatal CNS cells by testing for the effects of the biological agents on stem cell and progenitor cell proliferation and on progenitor cell differentiation or the survival and function of differentiated CNS cells.

Other screening applications of this invention relate to the testing of pharmaceutical compounds for their effect on neural tissue. Screening may be done either because the compound is designed to have a pharmacological effect on neural cells, or because a compound designed to have effects elsewhere may have unintended side effects on the nervous system. The screening can be conducted using any of the neural precursor cells or terminally differentiated cells of the invention.

Effect of cell function can be assessed using any standard assay to observe phenotype or activity of neural cells, such as receptor binding, proliferation, differentiation, survival-either in cell culture or in an appropriate model.

Therapeutic Uses

The fact that neural stem cells are located in the tissues lining ventricles of mature brains offers several advantages for the modification and manipulation of these cells in vivo and the ultimate treatment of various neurological diseases, disorders, and injury that affect different regions of the CNS. Therapy for these diseases can be tailored accordingly so that stem cells surrounding ventricles near the affected region would be manipulated or modified in vivo using the methods described herein. The ventricular system is found in nearly all brain regions and thus allows easier access to the affected areas. In order to modify the stem cells in vivo by exposing them to a composition comprising a reagent, it is relatively easy to implant a device that administers the composition to the ventricle and thus, to the neural stem cells. For example, a cannula attached to an osmotic pump may be used to deliver the composition. Alternatively, the composition may be injected directly into the ventricles. The neural stem cell progeny can migrate into regions that have been damaged as a result of injury or disease. Furthermore, the close proximity of the ventricles to many brain regions would allow for the diffusion of a secreted neurological agent by the stem cells or their progeny.

In an additional embodiment, a reagent of the invention is administered locally, as described above, in combination with an agent administered locally or systemically. Such agents include, for example, one or more stem cell mitogens, survival factors, glial-lineage preventing agents, anti-apoptotic agents, anti-stress medications, neuroprotectants, and anti-pyrogenics, or any combination thereof.

The agent is administered systemically before, during, or after administration of the reagent of the invention. The locally administered agent can be administered before, during, or after the reagent administration.

For example, when the reagent is PDGF, stem cell mitogens, e.g., EGF, FGF, VEGF, IGF-1, and insulin can be locally co-administered before, during and/or after a PDGF infusion. Additionally, in some aspects of the invention, survival factors, such as GDNF, CNTF, BDNF, NT-4, NGF, and erythropoietin can be locally co-administered before, during and/or after PDGF infusion.

For treatment of Huntington's Disease, Alzheimer's Disease, Parkinson's Disease, and other neurological disorders affecting primarily the forebrain, a reagent alone or with an additional agent or agents is delivered to the ventricles of the forebrain to affect in vivo modification or manipulation of the stem cells. For example, Parkinson's Disease is the result of low levels of dopamine in the brain, particularly the striatum. It is therefore advantageous to induce a patient's own quiescent stem cells to begin to divide in vivo and to induce the progeny of these cells to differentiate into dopaminergic cells in the affected region of the striatum, thus locally raising the levels of dopamine.

Normally the cell bodies of dopaminergic neurons are located in the substantia nigra and adjacent regions of the mesencephalon, with the axons projecting to the striatum. The methods and compositions of the invention provide an alternative to the use of drugs and the controversial use of large quantities of embryonic tissue for treatment of Parkinson's disease. Dopamine cells can be generated in the striatum by the administration of a composition comprising a reagent of the invention to the lateral ventricle.

For the treatment of MS and other demyclinating or hypomyelinating disorders, and for the treatment of Amyotrophic Lateral Sclerosis or other motor neuron diseases, a reagent of the invention, alone or with an additional agent or agents is delivered to the central canal.

In addition to treating CNS tissue immediately surrounding a ventricle, a reagent of the invention, alone or with an additional agent or agents can be administered to the lumbar cistern for circulation throughout the CNS.

In other aspects, neuroprotectants can also be co-administered systemically or locally before, during and/or after infusion of a regent of the invention. Neuroprotectants include antioxidants (agents with reducing activity, e.g., selenium, vitamin E, vitamin C, glutathione, cysteine, flavinoids, quinolines, enzymes with reducing activity, etc), Ca-channel modulators, Na-channel modulators, glutamate receptor modulators, serotonin receptor agonists, phospholipids, unsaturated- and polyunsaturated fatty acids, estrogens and selective estrogen receptor modulators (SERMS), progestins, thyroid hormone and thyroid hormone-mimicking compounds, cyclosporin A and derivatives, thalidomide and derivatives, methylxanthines, MAO inhibitors; serotonin-, noradrenaline and dopamine uptake blockers; dopamine agonists, L-DOPA, nicotine and derivatives, and NO synthase modulators.

Certain reagents of the invention may be pyrogenic following IV injection (in rats; Am. J. Physiol. Regul. Integr. Comp. Physiol. 2000 278:R1275-81). Thus, in some aspects of the invention, antipyrogenic agents like cox2 inhibitors, indomethacin, salisylic acid derivatives and other general anti-inflammatory/anti-pyrogenic compounds can be systemically or locally administered before, during and/or after administration of the reagent of the invention.

In another aspect of the invention, anti-apoptotic agents including caspase inhibitors and agents useful for antisense-modulation of apoptotic enzymes and factors can be administered before, during, or after administration of the reagent of the invention.

Stress syndromes lower neurogenesis, therefore in some aspects, it may be desirable to treat a subject with anti-stress medications such as, e.g., anti-glucocorticoids (e.g., RU486) and beta-blockers, administered systemically or locally before, during and/or after infusion of the reagent of the invention.

Methods for preparing the reagent dosage forms are known, or will be apparent, to those skilled in this art.

The amount of reagent to be administered will depend upon the exact size and condition of the patient, but will be from 0.5 ng/kg/day to 500 ng/kg/day in a volume of 0.001 to 10 ml.

The duration of treatment and time period of administration of reagent will also vary according to the size and condition of the patient, the severity of the illness and the specific composition and method being used.

The effectiveness of each of the foregoing methods for treating a patient with a CNS disease or disorder is assessed by any known standardized test for evaluating the disease.

Other features of the invention will become apparent in the course of the following description of exemplary embodiments which are given for illustration of the invention and are not intended to be limiting thereof. All references, patents and patent applications cited are hereby incorporated by reference in their entirety.

EXAMPLES

Example 1

The effect of PDGFs on Proliferation of Cultured, Non-Adherent Mouse Neurospheres Neurosphere Cultures The anterior lateral wall of the lateral ventricle of 5-6 week old mice was enzymatically dissociated in 0.8 mg/ml hyaluronidase and 0.5 mg/ml trypsin in DMEM containing 4.5 mg/ml glucose and 80 units/ml DNase at 37° C. for 20 min. The cells were gently triturated and mixed with three volumes of Neurosphere medium (DMEM/F12, B27 supplement, 125 mM HEPES pH 7.4) containing 20 ng/ml EGF (unless otherwise stated), 100 units/ml penicillin and 100 µg/ml streptomycin. After passing through a 70 µm strainer, the cells were pelleted at 160×g for 5 min. The supernatant was subsequently removed and the cells resuspended in Neurosphere medium supplemented as above, plated out in culture dishes and incubated at 37° C. Neurospheres were ready to be split approximately 7 days after plating.

To split the neurospheres, cells were collected by centrifugation at 160×g for 5 min. The conditioned supernatant (conditioned medium) was removed and saved. The neurospheres were resuspended in 0.5 ml Trypsin/EDTA in HBSS (1×), incubated at 37° C. for 2 min and triturated gently to aid dissociation. Following a further 3 min incubation at 37° C. and trituration, 3 volumes of ice cold Neurosphere medium medium w/o EGF were added to stop further trypsin activity. The cells were pelleted at 220×g for 4 min, and resuspended in a 1:1 mixture of fresh Neurosphere medium and conditioned medium. EGF was supplemented to 20 ng/ml and the culture plated out and incubated at 37° C.

Neurosphere Assays

NSCs, cultured as described above, from passage 2 were seeded in DMEM/F12 supplemented with B27 into a 96-well plate as single cells (10000 cells/well), to which agents were added at the concentrations indicated (1 nM-0.0005 nM). When cells were grown as adherent culture they were seeded in medium+B27 supplemented with 1% Fetal Calf Serum, after 6 hours when the cells had adhered, the medium was changed to serum free medium and agents were added in the same concentrations as indicated. The PDGFs used in the in vitro experiments were human recombinant PDGF-AA and human recombinant PDGF-BB.

Intracellular ATP Assay

Intracellular ATP levels have previously been shown to correlate to cell number (Crouch, Kozlowski et al. 1993). After 3 days of treatment, intracelluar ATP was measured using the ATP SL kit (Biothema) according to the manufacturer's instructions.

Results

Figure 2:
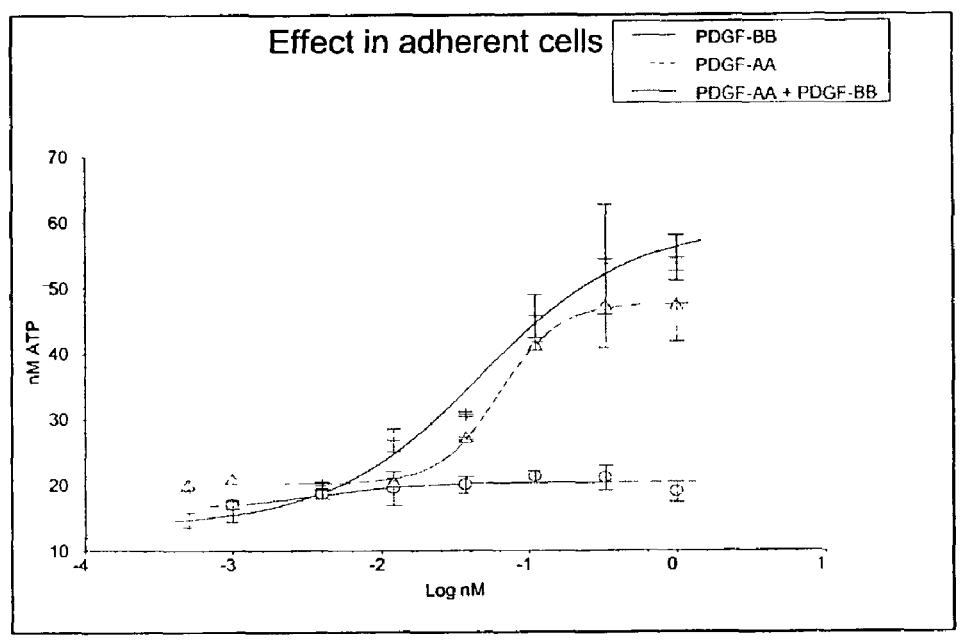
FIG. 2 shows the effect of PDGFs on proliferation of adherent cultured mouse NSC/progenitor cells.

In growth media supplemented with B27, PDGF-BB had a concentration dependent proliferative effect. The effect of PDGF-AA was weaker compared to BB, and when added together PDGF-AA did not alter the proliferative effect of PDGF-BB (FIG. 1). Considering the binding pattern, PDGF-AA binds only $\alpha\alpha$ PDGF receptor dimers while PDGF-BB binds all three possible combinations ($\alpha\alpha$, $\alpha\beta$ or $\beta\beta$), therefore, these results indicated that the proliferative effect was due to binding to $\beta\beta$ (or $\alpha\beta$) receptors. Similar results were also obtained if cells were grown as a more differentiated adherent culture (possibly progenitor cells) on poly-d-lysine (FIG. 2).

Example 2

Effects of PDGF-AA on GFAP and $\beta$-III Tubulin in Mouse Cultured Neural Stemcells/Progenitors NSCs, cultured as described above, were seeded from passage 2 into DMEM/F12 supplemented with B27 into a 24-well plate (poly-D-lysine-coated) as single cells (70.000 cells/well), to which PDGF-AA was added at the concentration of 1 nM. The cells were then differentiated for 5 days changing medium plus/minus PDGF-AA every 48 hours. At day 6 the cells were harvested and Western blots were performed as described elsewhere (Patrone C et al (1999) Proc Natl Acad Sci USA. 96(19):10905-10). A neuronal marker antibody against $\beta$-III Tubulin, 1:5000 (BioSite), or a glial marker antibody against glial fibrillary acidic protein (GFAP) 1:5000, (DAKO) was used to measure phenotypic fates.

Under certain conditions, in adherent cultures of adult neuronal stem cells treated with PDGF-AA for 6 days there was a downregulation of GFAP in comparison to treatment with EGF (left panel). The baseline media contains EGF whereas the media for the PDGF treated cells contain both EGF and PDGF. In contrast, a significant increase of the neuronal specific $\beta$-III Tubulin marker was observed (right panel) as a response to treatment with PDGF-AA compared to treatment with EGF. This result implicates PDGF-AA in differentiation of neural stem cells into neurons. Sample loads were normalized to protein and DNA content.

Figure 3:
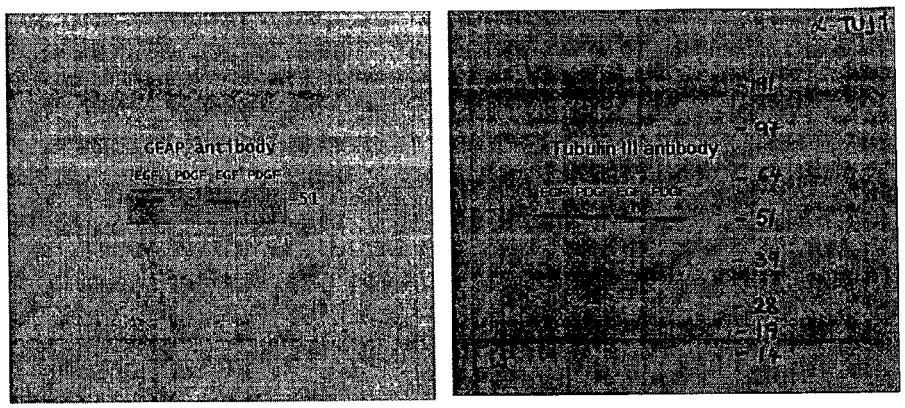
FIG. 3 is Western blots showing the effect of PDGF-AA in cultured neurospheres. Downregulation of GFAP (left); upregulation of β-III Tubulin (right).
Figure 4:
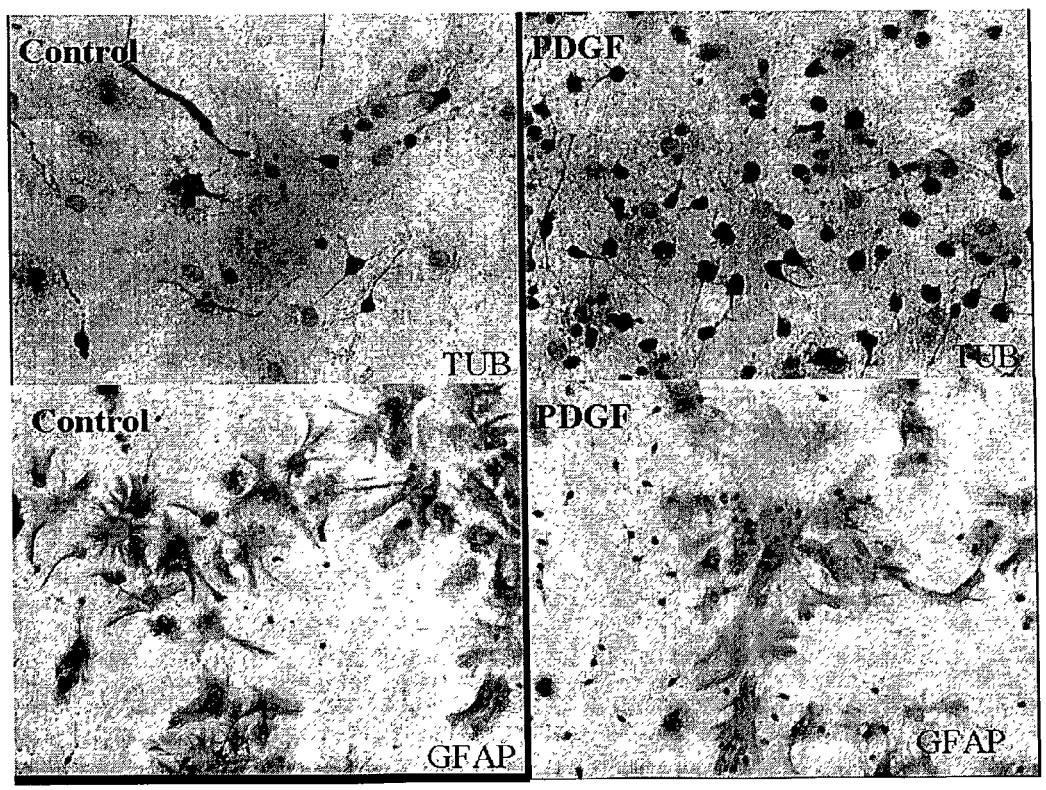
FIG. 4 depicts the effect of PDGF-AA in cultured mouse NCCs/neural progenitor cells (NPCs). Upper panel: adult mouse NSCs treated with PDGF-AA for 6 days switch from an undifferentiated (left panel) to a neuronal phenotype (right panel) increasing the specific neuronal marker β-III Tubulin. Lower panel: in contrast to the above, adult mouse NSCs treated with PDGF-AA for 6 days significantly decrease the specific expression of the glial specific marker GFAP indicating that the astroglial component was reduced in presence of PDGF-AA.

In another set of experiments the effects of PDGF-AA were studied with immunocytochemical methods in fixed adherently cultured neural stem cells. In these experiments a similar result to the Western-study was observed, e.g., an upregulation of $\beta$-III Tubulin and a down regulation of GFAP (FIG. 3). In other experiments with PDGF-AA, analyzed by immunocytochemistry, it was shown that the factor caused a general shift from a stem cell phenotype to a progenitor phenotype in that cultures contained both of the markers, GFAP and $\beta$-III Tubulin. However, in all instances there was no overlap between markers, suggesting that PDGF-AA promotes differentiation to both glial and neural lineages via distinct pathways (FIG. 4). In concurrent experiments the effect of PDGF-BB was also studied. Similar effects as those observed with AA was obtained with BB (data not shown).

Example 3

The Effect of PDGF-AA and PDGF-BB on Neural Differentiation (III Tubulin) of Mouse Neural Stem Cells Differentiation Adult mouse neuroperes were dissociated with trypsin (Gibco) into single cells and transferred to poly-D-Lysine plates (BD) in the above culture medium, without growth factors, supplemented with 1% Fetal Calf Serum (Gibco). The cells were incubated over night to adhere to the plate. The medium was changed to culture medium, without growth factors, supplemented with 1 nM PDGF-AA or PDFG-BB (both from R&D Systems). The medium with new substance added every second day. The cells were incubated for a total of 7 days.

Immunohistochemistry

The cells were washed two times with PBS (Gibco) and fixed for 15 min RT with 4% Formaldehyde (Sigma) and permeabilized 20 min RT in 0.1% Triton X-100 (Sigma) in PBS. After fixation and permeabilization the cells were labelled with mouse monoclonal anti-$\beta$-III Tubulin (1:500 Promega). Primary antibody was visualized with anti mouse Texas-Red (1:100 Vector Laboratories). All antibodies were diluted in PBS with 0.1% Triton X-100.

Protein Expression Analysis With Western Blot

The cells were washed twice with PBS (Gibco) and lysed with 200 ul lysis buffer/well. The lysis buffer contained PBS, 0.1% Triton X-100, 1 mM EDTA and 1 tab1. Protease inhibitor cocktail (Roche). The samples were run on a 4-12% Bis-Tris gel (Novex) under reduced conditions with MOPS buffer (Novex) and blotted onto a Hybond ECL nitrocellulose membrane (Amersham Biotech). Blocked in 5% ECL-Block (Amersham Biotech) in PBS+0.1% Tween 20 (Sigma). The membranes were labelled with mouse monoclonal anti-$\beta$-III Tubulin (1:5000 Promega). The primary antibody was detected using a secondary antibody anti-mouse-HRP (1:10000 Amersham Biotech) and ECL Plus+ Western Blot Detection Kit (Amersham Biotech). All antibodies were diluted in PBS with 0.1% Triton X-100, 1% ECL Block. The signal were then captured on ECL Hyper Film (Amersham Biotech)

Figure 5:
FIG. 5 shows the effect of PDGF-AA and PDGF-BB on neuronal differentiation of adult mouse stem cells. Compared to the control (panel A) the stimulation with PDGF-AA (panel B) and PDGF-BB (panel C) significantly increase the number of β-III Tubulin positive cells in culture.
Figure 6:
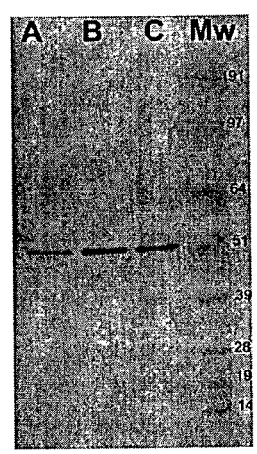
FIG. 6 is a Western blot showing the effect of PDGF-AA and PDGF-BB on neuronal differentiation of adult mouse stem cells. Compared with the control (A) the stimulation with PDGF-AA (B) and PDGF-BB (C) significantly increased levels of β-III Tubulin protein. Sample loads were normalized.

As measured qualitatively (FIG. 5) and quantitatively (FIG. 6), PDGF-AA and PDGF-BB trigger neuronal differentiation of cultured mouse neural stem cells/progenitors.

Example 4

In Vivo Neurogenic Action of BB in Healthy Rats After ICV Infusion

Male rats (12 hours light/dark regime; feeding and drinking ad libitum; 5 animals in standard cage) were infused (Alzet minipumps) in the left lateral ventricle with human recombinant PDGF-BB for 7 days at a daily dose of 36 ng/day (8 animals/group). Human recombinant BDNF (brain derived neurotrophic factor) was used as a positive control (Pencea V et al., J. Neurosci Sep. 1 (2001), 21(17):6706-17). Bromodeoxyuridine (BrdU) was also included in the infusion vehicle (artificial cerebrospinal fluid) to enable measurement of proliferation by quantitation of BrdU incorporation in the DNA. Animals were sacrificed at 7 (proliferation) or 28 days (neurogenesis) after start of treatment and brains were dissected and prepared for sectioning and immunohistochemistry (Pencea V et al., J. Neurosci Sep. 1 (2001), 21(17):6706-17).

Figure 7:
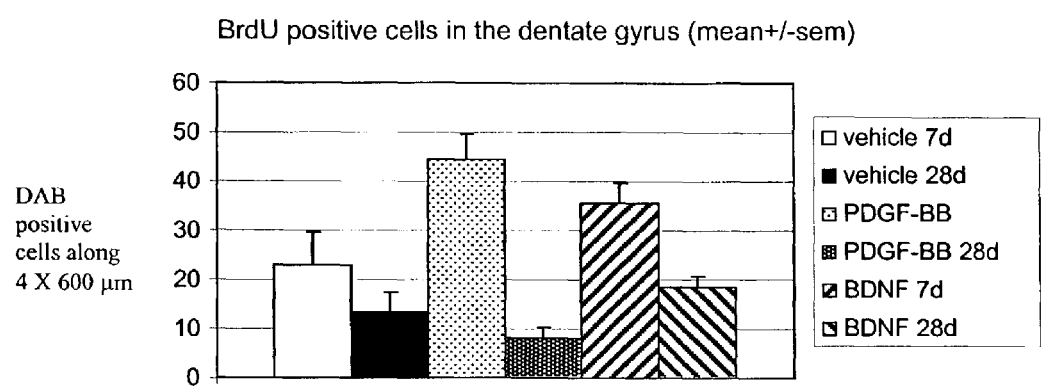
FIG. 7 represents the effect of PDGF-BB on the number of BrdU positive cells in the dentate gyrus.

Proliferation was measured by BrdU incorporation and diaminobenzidine (DAB) staining of HRP conjugated secondary antibodies (FIG. 7). Cells were counted in a phase contrast microscope. Neural phenotype was assessed by staining for neuronal marker NeuN by immunocytochemistry using a fluorescence readout. The secondary antibodies were labeled with FITC or Alexa Fluor568. In double staining analyses designed to measure neurogenesis, BrdU and NeuN were quantitated by fluorescence (above) and counting of cells was done in a confocal microscope. For further experimental details, see Pencea V et al., J. Neurosci Sep. 1 (2001), 21(17):6706-17. A number of brain regions were analysed.

7-Day Group (Proliferation)

TABLE 1

PDGF-BB increased proliferation of the ventricle wall in comparison to vehicle-treated animals. The mean values of two sections, m3 × 600 micrometer counted along the lateral ventricle wall were the following (mean +/− sem):

| Condition: | Cell count: | |
|---|---|---|
| vehicle | 134 +/10 | |
| PDGF-BB | 216 +/−25 | (p < 0.05 to vehicle, ANOVA) |
| reference compound (BDNF) | 177 +/−15 | (p < 0.05 to vehicle, ANOVA) |

In the dentate gyrus of the hippocampus and the olfactory bulb there was no significant effect recorded on the proliferation marker BrdU by either compound. A nonsignificant tendency towards more BrdU cells (proliferation) were recorded (Table 1).

28-Day Group (Neurogenesis)

In BrdU labeling analyses, in the dentate gyrus, the CA1 and the alveus there was no significant effect of PDGF or BDNF, rather a (non-significant) tendency for decrease of BrdU positive cells in comparison to vehicle-treated animals (not shown).

Double labeling analyses revealed that the ratio of NeuN positive cells to BrdU positive cells was similar (no significant difference) in all three groups in all areas investigated (dentate gyrus, CA1, alveus, subventricular zone, striatum) (not shown).

In the subventricular zone there was a slight effect of BDNF to increase the number of proliferating cells. PDGF had no such statistically significant effect (not shown).

Figure 8:
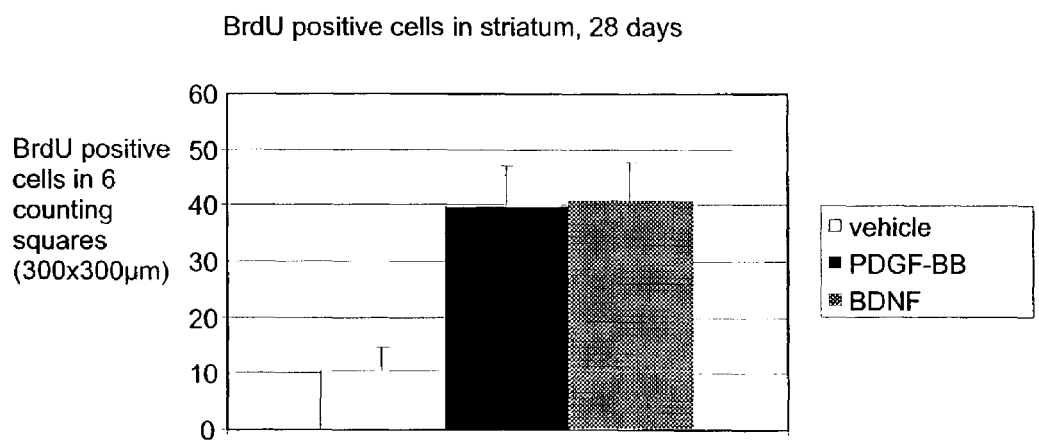
FIG. 8 shows the effect of PDGF-BB on BrdU positive cells in the striatum.

In the striatum there was a significant increase in BrdU positive cells after-infusion of PDGF-BB and BDNF in comparison to vehicle-treated animals (Table 2, FIG. 8). The results revealed that vehicle and factor groups show the same ratio of double labelled cells, it is concluded that infusion of PDGF-BB (and BDNF) significantly increase neurogenesis in the striatum in comparison to vehicle treated animals.

TABLE 2

The effect of PDGF-BB on BrdU positive cells in the striatum.

Cells were counted in 300 × 300 μm squares

| Vehicle | 10.6 ± 4.2 |
| PDGF-BB | 40 ± 6.8 (p < 0.01 to vehicle, ANOVA) |
| BDNF | 39.8 ± 7.3 (p < 0.01 to vehicle, ANOVA) |

In the striatum there was a gradient of BrdU-labeled cells from ventricle to cortex which indicates that the cells may originate from the subventricular zone. In the CA1/alveus region no such gradient was observed.

Example 5

PDGF-BB Counteracts MPTP-Induced Neuronal Loss in Substantia Nigra Pars Compacta Animals Ten-week old male C57B1/6 mice (25 g, B&K Universal, Stockholm, Sweden).

Drug Delivery

PDGF-BB (Sigma) was administered directly into the right lateral ventricle of the brain using osmotic pumps (Alza 1003D, delivery of 1.0 μl/h for three days) and brain infusion kits. The drug solution was prepared as follows: 10 μg PDGF-BB was dissolved in 10 μl 1M HAc, after which pH was adjusted to 7.4 by adding 10 μl NaOH. A buffer was added (100 ml 0.01M PBS containing 5 mg/ml BSA and 20 mM Hepes) to a final volume of 4,000 μl. Each minipump was connected to a brain infusion needle, which was stereotaxically placed in the right lateral ventricle of the mouse brain in deeply anesthetized mice (chloral hydrate 60 mg/kg intraperitoneal). The pump was placed subcutaneously in the neck. The delivery rate of PDGF-BB was 0.1 μg/h/kg body weight. $^3$H-thymidine (6.7 Ci/ml, NEN) was given for three days via another Alzet pump which was placed intraperitoneally.

One hour after the pumps were inserted, the neurotoxin 1-methyl-4-phenyl-1,2,3,6-tetrahydropyridine (MPTP HCl, Sigma) was given subcutaneously (40 mg/kg).

Two months later, animals were anesthetized with choral hydrate (60 mg/kg ip) and sacrificed by intracardial infusion of fixative (4% paraformaldehyde in 0.1 M phosphate buffered saline (PBS) containing 0.4% picric acid. After dissection, postfixation in the same fixative continued for 1.5 h followed by cryoprotection. After dissection of the midbrain, the two sides of the brain were separated with a cut along the ventro-dorsal midline and the tissue was postfixed in the same solution and cryoprotected in sucrose. Cryostat sections were prepared as follows: a randomly chosen half-brain was cut into 40 μm thick sections through the full rostro-caudal extension of substantia nigra pars compacta. A randomly chosen series of every 6$^{th}$ section was taken to perform free-floating immunohistochemistry using a polyclonal anti-tyrosine hydroxylase antibody (diluted 1:400, Pel-Freez) in order to identify dopaminergic neurons in the tissue. To visualize the antibody, the avidin-biotin peroxidase kit (Vector) with 0.03% DAB as chromagen was used adding 0.01% $H_2O_2$. Cresyl violet was employed to identify the nucleolus, Nissl substance and glia cells (Chan et al., 1997; Walters et al., 1999). The other half of the brain was sectioned in 10 µm thick sections on glass and a randomly chosen series of every 6$^{th}$ section was immunohistochemically stained for tyrosine hydroxylase in dopaminergic neurons as previously described. To detect incorporation of the $^3$H-thymidine nucleotide in brain cells, the sampled slides were dipped in NTB2 nuclear track emulsion (Kodak) and stored in light-tight boxes at −20° C. for four weeks. The granular black label was developed in D-19 (Kodak, diluted 1:2 with d.w. at 16-18° C.).

Analysis

The total number of dopaminergic neurons in the substantia nigra pars compacta was estimated with an optical fractionator using a 100× oil immersion objective to detect the neuronal sampling unit, the nucleolus (Janson and Møller, 1993) (coefficient of error for each estimate was <0.09). Volume of the neurons was estimated with the rotator in vertical sections (Janson and Møller, 1993). Proliferation of new neurons was shown as black dots over cells where the radioactive nucleotide was incorporated.

Infusion of PDGF Causes Nigral Neurons to Proliferate

PDGD-BB completely counteracted the MPTP-induced loss of tyrosine hydroxylase positive nerve cells after an MPTP lesion. Mice were lesioned with MPTP and treated with PDGF. Neurons of the substantia nigra were stained with Nissl stain and then counted. Animals were also infused with tritiated thymidine in order to allow for measurement of proliferation. Upon the analysis of the number of cells in the substantia nigra in the MPTP lesioned mice after infusion of PDGF, not only did the cell number in the structure double but cells were also positive for proliferation. For example, neural cells of the substantia nigra had also incorporated tritiated thymidine in their nuclei as shown by observing black autoradiographic grains over nuclei of Nissl stained cells. Quantitative results are summarized in Table 3.

TABLE 3

Total number of tyrosine hydroxylase neurons in the bilateral substantia nigra pars compacta in MPTP-lesioned animals treated with PDGF-BB intraventricularly.

| | |
|---|---|
| Saline (n = 6) | 11,900 ± 100 |
| PDGF-BB (n = 3) | 12,300 ± 300 |
| MPTP + Saline (n = 6) | 5,500 ± 700* |
| MPTP + PDGF-BB (n = 3) | 10,000 ± 200 |

Mean ± S.E.M, number of animals in each group within parenthesis. Statistical analysis was performed with ANOVA followed by Scheffe's post-hoc test.
* = P < 0.001, different from all other animal groups. For details on animals and treatment, see text.

Figure 9:
FIG. 9 depicts a large neuron in the MPTP-lesioned mouse receiving PDGF. This tyrosine hydroxylase-positive (brown) nerve cell with a violet nucleolus in the centrally placed nucleus without brown staining had an estimated volume of 10,900 $\mu m^3$. Anti-tyrosine hydroxylase was visualized with the avidin-biotin-peroxidase-DAB method and cresyl violet was employed as counterstain. Bar=10 μm.
Figure 10:
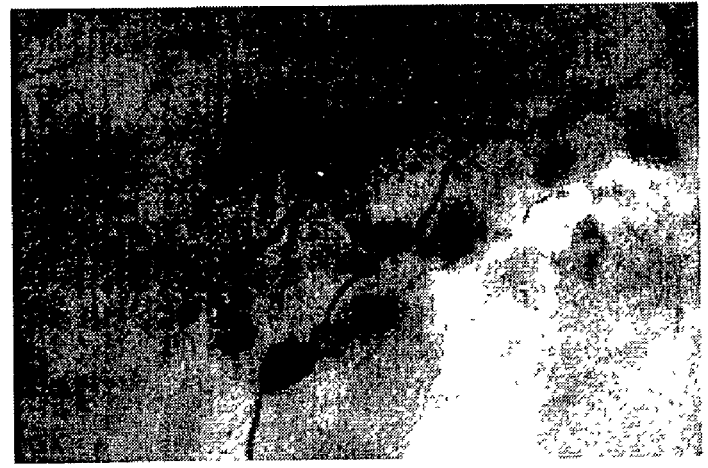
FIG. 10 represents a small tyrosine hydroxylase-positive neuron in the MPTP-lesioned PDGF-treated mouse. The cell had an estimated volume of 170 $\mu m^3$, e.g. similar to a small glia cell, but demonstrated a clear neuronal bipolar phenotype with long dendrites that extended for more than 100 μm in the 40 μm thick section.
Figure 11:
FIG. 11 shows a $^3$H thymidine label (black dots) over a substantia nigra neuron (Nissl stain) in a PDGF-treated MPTP-lesioned mouse. Bar=10 μm.

In the PDGF-BB+MPTP group, the size of the nigral dopamine neurons varied substantially. Whereas some neurons were found to be greater than the usual size of dopamine neurons (FIG. 9), others were instead unusually small (FIG. 10). The former may represent stimulation of neuronal growth in neurons surviving the lesion, whereas the latter, small bipolar tyrosine hydroxylase positive neurons, may result from a process where new nerve cells are recruited to the nigral neuronal population from progenitor cells. Stimulation of proliferation of NSCs/NPCs as well as enhanced migration into substantia nigra and differentiation into a dopaminergic phenotype is suggested to be the mechanism for the increased cell numbers in the lesioned animals treated with PDGF-BB. The involvement of increased proliferation in the increased cell numbers is indicated by the finding of a granular black label representing $^3$H-thymidine over nigral nerve cells (FIG. 11).

Example 6

PDGFR-A and PDGFR-B Genes are Expressed in Cultured Human Neural Stem Cells

Human Stem Cell (HSC) Cultures

A biopsy from the anterior lateral wall of the lateral ventricle was taken from an adult human patient and enzymatically dissociated in PDD (Papain 2.5 U/ml; Dispase 1 U/ml; Dnase I 250 U/ml) in DMEM containing 4.5 mg/ml glucose and 37° C. for 20 min. The cells were gently triturated and mixed with three volumes of Human Stem Cell Plating Medium (HSCPM) (DMEM/F12; 10% FBS). The cells were pelleted at 250×g for 5 min. The supernatant was subsequently removed and the cells resuspended in HSCPM, plated out on fibronectin coated culture dishes and incubated at 37° C. in 5% $CO_2$. The following day the expansion of the culture was initiated by change of media to HSC culture media (DMEM/F12; BIT 9500; EGF 20 ng/ml; FGF2 20 ng/ml). The HSC were split using trypsin and EDTA under standard conditions. FBS was subsequently added to inhibit the reaction and the cells collected by centrifugation at 250×g for 5 min. The HSC were replated in HSC culture media.

RT-PCR

The following primer pairs were designed to specifically identify the presence of pdgfr-a, and pdgfr-b gene expression in HSC cultures. Estimated band sizes for each primer pair are given below:

| | | Band size (base pairs) |
|---|---|---|
| PDGFR-A | aaccgtgtataagtcagggaaacg (SEQ ID NO:9) | 355 |
| | Ccgcacctctacaacaaaatgtttg (SEQ ID NO:10) | |
| | Aaccgtgtataagtcagggaaacg (SEQ ID NO:11) | 507 |
| | Tggccactgtcttcttccttagca (SEQ ID NO:12) | |
| PDGFR-B | gtctctgtgaacgcagtgcagactg (SEQ ID NO:13) | 338 |
| | Gcaaattgtagtgtgcccacctct (SEQ ID NO:14) | |
| | Gtctctgtgaacgcagtgcagactg (SEQ ID NO:15) | 382 |
| | Aggcctcgaacactacctgcagtg (SEQ ID NO:16) | |

HSC were prepared and cultured as stated above. Total RNA isolated using Qiagen's RNeasy Mini Kit according to the manufacturer's instructions and DNase treated using Ambion Dnase I and according to protocol. Life Technology's One-Step RT-PCR Kit was used to detect the presence of pdgfr-a and pdgfr-b mRNA. Briefly, 50 ng of total RNA was used in each reaction, with an annealing temperature of 54° C. To further ensure that genomic contamination of the total RNA did not give rise to false positive results, an identical reaction in which the RT-taq polymerase mix was replaced by taq polymerase alone and was run in parallel with the experimental RT-PCR. The reactions were electrophoresed on a 1.5% agarose gel containing ethidium bromide and the bands visualised under UV light.

Figure 12:
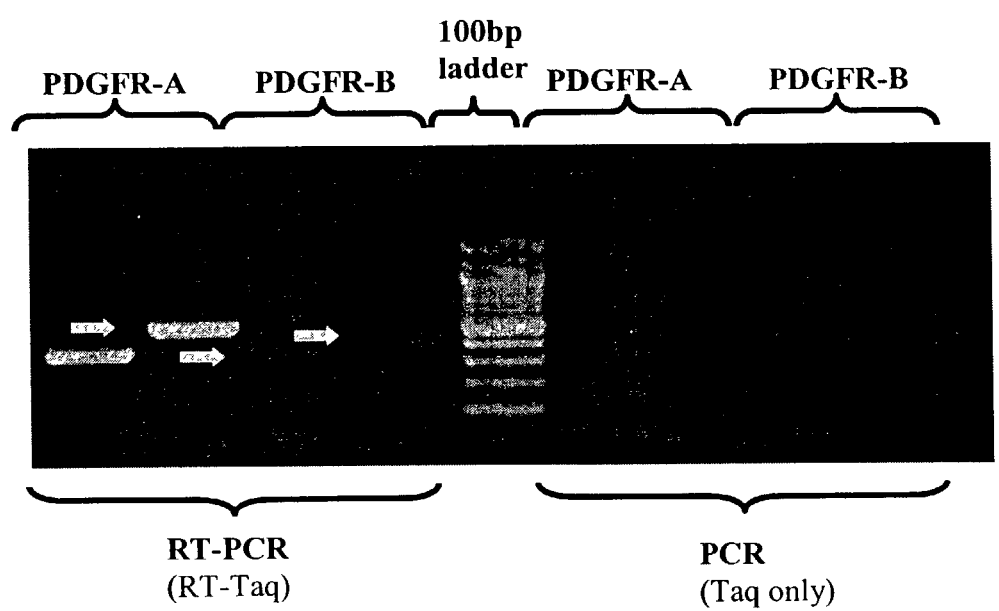
FIG. 12 shows that PDGFR-A and PDGFR-B genes are expressed in cultured human neural stem cells.

RT-PCR was performed on total RNA prepared from cultured HSC using primer pairs specific for the above genes (FIG. 12). The bands indicated with a white arrow correspond to the bands of the desired size (PDGFR-A [lane1 355 bp; lane2 507 bp], PDGFR-B [lane3 338 bp; lane4 382 bp]), verifying that they represent correct product. A parallel control experiment without using any reverse transcriptase, only taq polymerase, ruled out false positive bands through genomic contamination.

Example 7

The Effects of i.c.v. Infused PDGF-BB in 6-OHDA Lesioned Rats

BDNF, which has been previously shown to increase neurogenesis in the normal intact brain (Pencea et al., 2001), was used as a reference compound. Both PDGF and BDNF increased the numbers of newly formed cells in the substantia nigra and striatum at 12 weeks following treatment, as detected with BrdU-staining. At 5 weeks after treatment, neuronal phenotyping of BrdU-labeled cells with NeuN in the striatum revealed a significant increase in newly generated neurons.

Animals and Surgical Procedures

Animal handling and surgical procedures were carried out according to the ethical and regulatory permits set forth by Jordbruksverket and Lund University. Adult female Sprague-Dawley rats (B&K Universal AB) rats weighing 220-250 g, were housed in pairs with a 12 h light-dark cycle with free access to food and water. To lesion the substantia nigra, rats were fixed into a stereotaxic frame and 6-OHDA (3 mg in 0.02% ascorbate saline, Sigma) was injected at a rate of 1 µl/min in 2 deposits of 2 and 2.5 µl into the right ascending mesostriatal forebrain bundle at the following coordinates: 4.4 mm caudal to bregma, 1.2 mm lateral to midline, 7.8 mm below dura; 4.0 mm caudal, 0.8 mm lateral, 8.0 mm below dura, respectively (Paxinos and Watson, 1998). Three weeks after 6-OHDA injections, the completeness of the lesion was assessed with the amphetamine-induced rotation test. D-methylamphetamine (2.5 mg, i.p.) was injected 5 min prior to placing the rat in an automated rotormeter bowl that measured the number of rotations over 90 min. Rats that exhibited over 5 net ipsilateral (to the lesioned hemisphere) turns per min advanced to the next phase of the study to have osmotic minipumps implanted.

Before implantation, an Alzet Model 2002 osmotic minipump (200 µl; flow rate: 0.5 µl/h, 12 µl/day) was prefilled with 200 µl of compound solution (see below) and placed in a NaCl (0.9%) solution warmed in water bath (37° C.) 36 hrs before implantation. Rats were anesthetized with halothane in a mixture of nitrous oxide/oxygen (70:30) and maintained with 2-3% halothane. For implantation, rats were placed in a stereotaxic frame and the cannula of the Alzet Brain Infusion kit II was placed into the right lateral ventricle (coordinates: AP=−0.3 mm posterior bregma, L=1.5 mm lateral to satura sagittalis, 4.5 mm the dura; Paxinos and Watson, 1998), and secured to the skull with screws and dental cement. The minipump was then placed subcutaneously in the mid-scapular region. The scalp was treated with lidocaine gel before suturing. Twelve days after insertion, the rats were briefly anaesthetized with halothane in order to remove the pump. Removed pumps had the remaining solution volume and weight recorded.

Growth Factors and Experimental Design

The effects of infused PDGF-BB and BDNF following 6-OHDA lesions were investigated at 2 different time points: at 12 days or 5 weeks after minipump insertion. Rats receiving human PDGF-BB (order # 220-BB-050; 50 µg, R&D Systems) each had 36 ng/d of PDGF dissolved in 0.1 M PBS (3 µg/ml). Rats receiving human recombinant BDNF (order # 248-BD-025; 25 µg, R&D Systems) each had 12 ng/d of BDNF dissolved in 0.1 M PBS (1 µg/ml). BrdU was co-administered with the compound solution in the minipumps by dissolving it into the 0.1 M PBS medium. Control rats received only BrdU/PBS infusions.

Tissue Processing and Immunohistochemistry

Brain tissue was obtained by anesthetizing the rat and transcardially perfusing with 0.9% saline followed by 4% paraformaldehyde (PFA). Brains were stored PFA for 2 hours, then transferred to 20% sucrose PBS and sectioned coronally on a sledge microtome at 30 µm thickness. Free-floating sections were stored in Walter's antifreeze solution at 4° C. until staining.

To detect for newly generated BrdU-positive cells, sections were incubated for 30 min in 2 M HCl at 37° C. to denature DNA, and subsequently incubated in blocking serum (5% normal horse serum in 0.1 M PBS containing 0.25% Triton X-100 for 1 hr). Following blocking, incubation of monoclonal rat anti-BrdU antibody (Harlan Sera Lab, UK) in 2% blocking solution occurred at a dilution of 1:100 at 4° C. for 36 hrs. The sections were then incubated with biotin-horse-anti-mouse antibody (1:200) (Vector, CA) in 2% blocking solution for 2 hr and visualized with DAB-NiCl Vectastain Elite kit. The procedure for doubling labeling of BrdU with NeuN or TH was similar, except that a monoclonal rat anti-BrdU antibody (1:100; Sigma, Sweden) was incubated either with a monoclonal mouse anti-NeuN antibody (1:100; Chemicon, USA) or with a monoclonal anti-TH antibody (1:1000; Pelfreeze) in the appropriate 2% blocking solution in the dark for 36 to 48 hrs. For immunofluorescent visualization, sections were incubation in secondary antibodies: Cy3-conjugated donkey anti-rat (1:200; Jackson ImmunoResearch, PA) for BrdU; a biotinylated horse anti-mouse antibody (1:200; BA2001, Vector, CA) for NeuN; and a FITC-conjugated goat anti-rat (1:200;) for TH. After 2 hrs of incubation at room temperature, a further 2 hr incubation with Alexa Fluor 488 conjugated goat anti-mouse secondary antibody (1:200; Molecular Probes, Netherlands) for NeuN was required. All sections were mounted onto glass slides and cover slipped with Prolong Antifade mounting medium (Molecular Probes).

Quantitative Analyses

All analyses were conducted by an observer blind to the treatment conditions. In the substantia nigra, the number of BrdU-labeled cells was determined with conventional epifluorescence or light microscopy with a 40× objective. All cells were counted bilaterally from 5 to 7 coronal sections per rat, located between 4.8 to 6.0 mm posterior to bregma. All counts were pooled together for each rat and are reported as mean number of cells per lesioned substantia nigra.

In the striatum, the number of BrdU-labeled cells was determined using stereological cell number and volume estimations. Three sections, taken from 10 parallel series of 30 µm thick coronal sections located between 1.6 mm anterior to 0.2 mm posterior to bregma, were analyzed for each rat. A modified optical fractionator method (Gundersen & Jensen 1987) was employed, with an 40× objective fitted on an Olympus BH-2 microscope, a X-Y-Z step motor stage run by a PC computer, a CCD-IRIS color video camera, and CAST-GRID software (Olympus, Denmark). For systematic sampling, the frame area and counting interval was set to allow for at least 200 cells to be sampled from each region of interest.

The optical dissector was set to sample all cells below the first 2 μm from the surface of the section.

For the longer delay time groups (5 weeks) co-localization of BrdU-positive cells with TH in the substantia nigra, and NeuN in the striatum, was assessed using a confocal scanning light microscope (Leica DM IRE3 microscope, Leica Confocal Software Version 2.77). Fifty cells from the lesioned hemisphere were analyzed for each rat, from the same regions where BrdU cell counts were conducted.

Statistical analyses were performed by ANOVA, with alpha set at 0.05.

Newly Generate Cells in the Striatum

Figure 13:
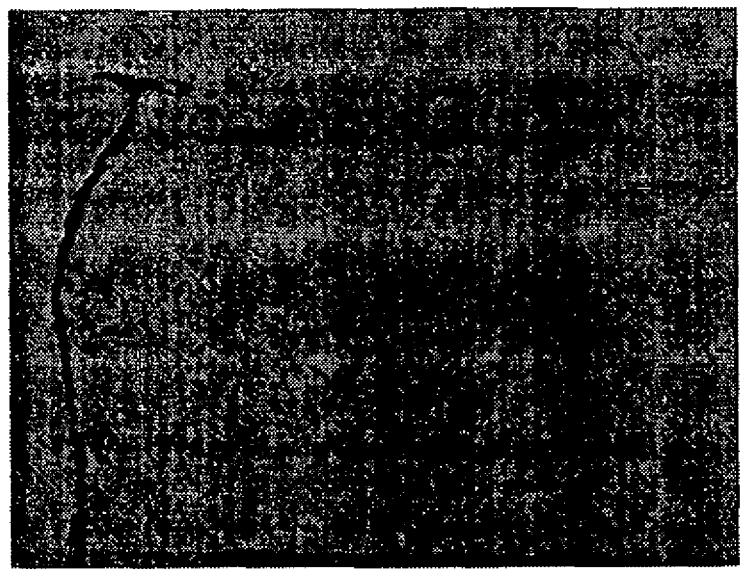
FIG. 13 shows immunohistochemically stained BrdU-labeled cells in the striatum at 5 weeks after PDGF infusion. (A) PBS control, (B) PDGF treated.
Figure 13:
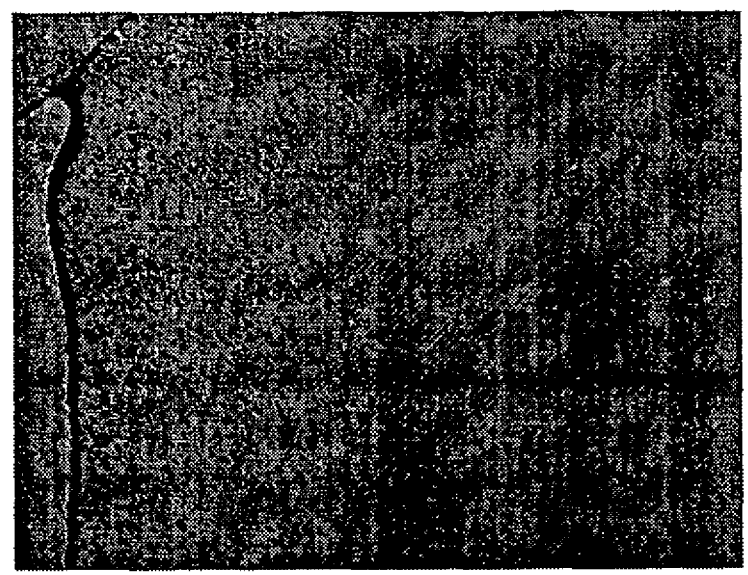
Figure 14:
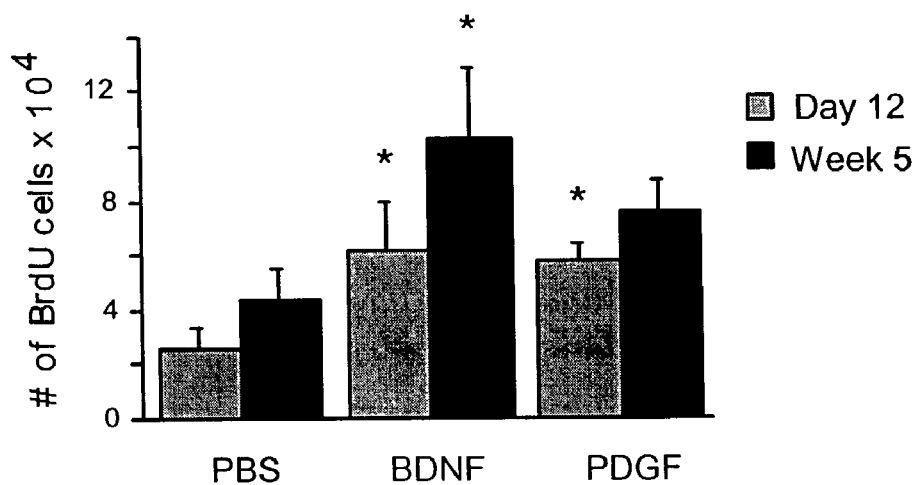
FIG. 14 represents the number of BrdU-labeled cells in the striatum at 12 days and 5 weeks after PDGF or BDNF infusion. *$p<0.05$ compared to PBS infused controls. Means±SEM.
Figure 15:
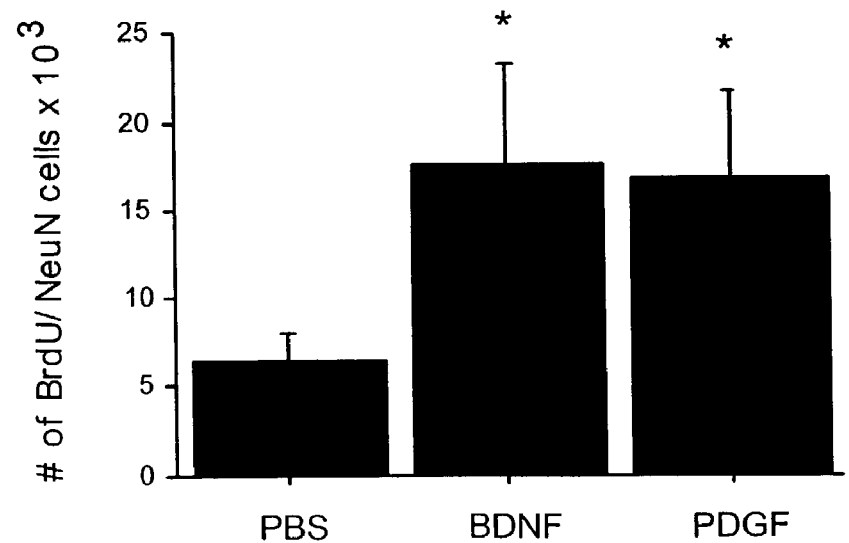
FIG. 15 depicts the number of BrdU/NeuN double-labelled cells in the striatum at 5 weeks after PDGF or BDNF infusion. Note that due to heterogeneity of variance with groups, data were logarithmically transformed. *$p<0.05$ compared to PBS infused controls. Means±SEM.

Substantial numbers of BrdU labelled cells were observed in the 6-OHDA denervated striatum (27-fold greater than non-lesioned hemisphere). Both PDGF and BDNF treatment significantly elevated the numbers of BrdU labelled cells in the denervated striatum as compared to PBS infusion (FIG. 13), with no differences between the two growth factors (FIG. 14). These significant increases in cell numbers were primarily observed at 12 days after infusion, such that only the BDNF rats exhibited significant increases at 5 weeks. At Week 5, there was no statistically significant differences in the proportion of newly generated neurons, such that: 15.3% of PBS, 16.6% of BDNF, and 20.9% of PDGF treated rats had BrdU cells in the striatum co-labelled with NeuN. Importantly, when estimating the absolute number of BrdU/NeuN double labelled cells, PDGF and BDNF treatment was found to have generated significantly more neurons (FIG. 15).

Newly Generate Cells in the Substantia Nigra

Figure 16:
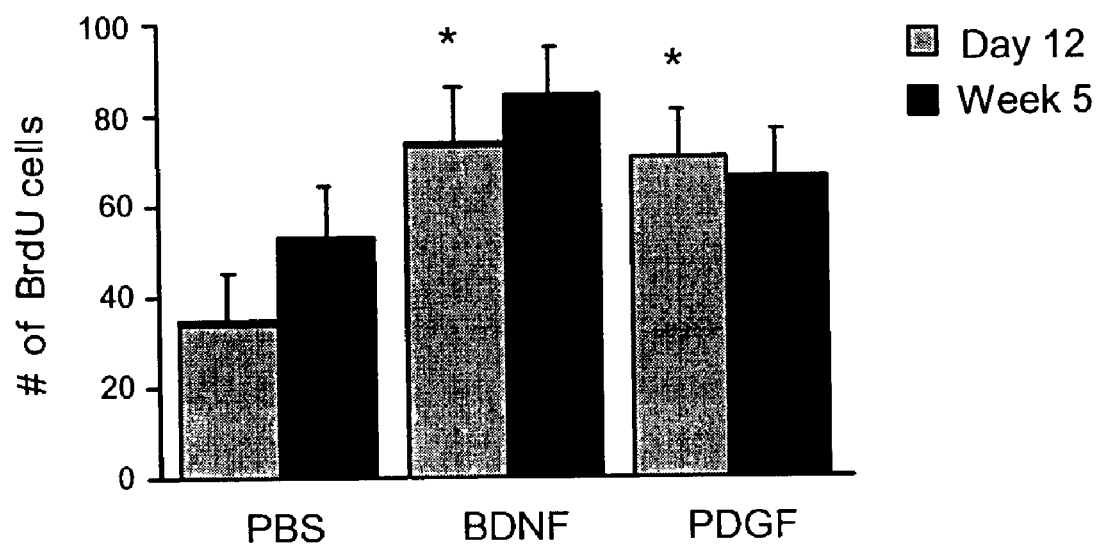
FIG. 16 shows the number of BrdU-labeled cells in the substantia nigra at 12 days and 5 weeks after PDGF or BDNF infusion. *$p<0.05$ compared to PBS infused controls. Means±SEM.

Substantial numbers of BrdU labelled cells were observed in both the lesioned and non-lesioned substantia nigra; however, the lesioned hemisphere had significant more cells (30% over non-lesioned side). Despite the infusions of growth factors being made into the lateral ventricle (over 5 mm distance from the substantia nigra), both PDGF and BDNF treatment significantly elevated the numbers of BrdU labelled cells in the lesioned nigra as compared to PBS treatment, with no differences between the two growth factors (FIG. 16). These significant increases in cell numbers were only observed at 12 days after infusion, and not at 5 weeks.

Overall, it was found that the administration of PDGF to a damaged brain can induce newly formed cells to migrate and differentiate to neurons in the denervated striatum, and potentially into the damaged substantia nigra as well. These promising results support the therapeutic use of PDGF to restore neurons lost in Parkinson's disease.

Example 8

Figure 17:
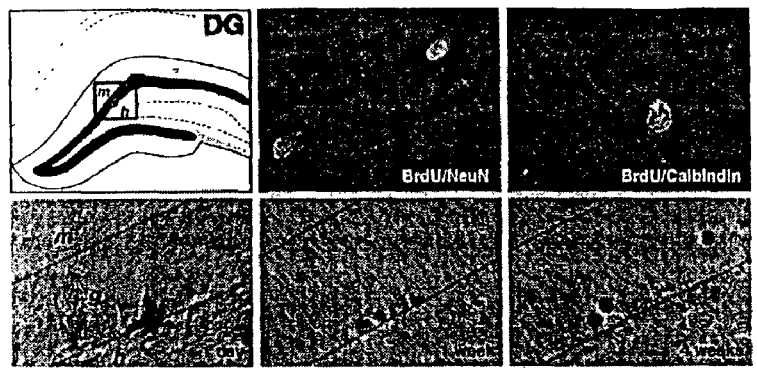
FIG. 17 depicts neurogenesis in the hippocampus which is characterized by proliferative clusters of cells along the border between the granule cell layer (g) and the hilus region (h). These cells begin to migrate into the granule cell layer about 1 week after their last cell division and can be colabeled with markers for granule cells (e.g., NeuN and Calbindin).
Figure 18:
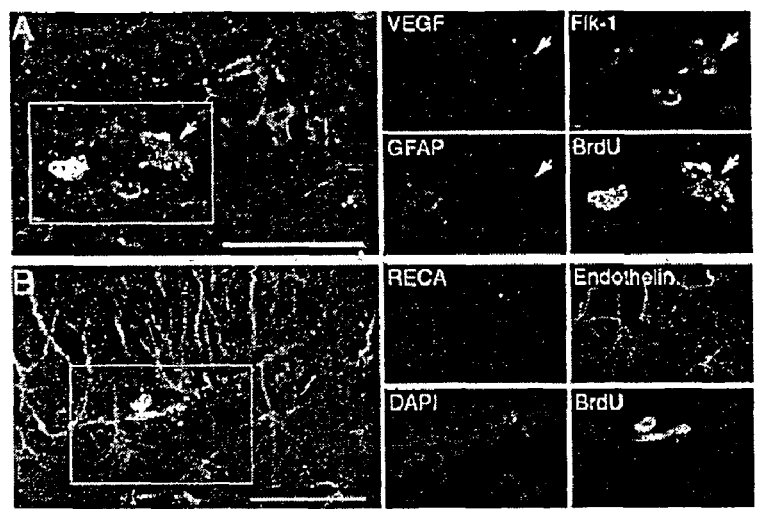
FIG. 18 represents Flk-1-positive cells in the dentate gyrus. Frequently Flk-1 positive cells are associated with clusters of proliferating cells. These clusters contain endothelial cells as well as NSCs/NPCs. (A) Multiple immunofluorescence with BrdU, VEGF and Flk-1. Note the colocalization of Flk-1 and BrdU. (B) BrdU positive cells are associated with blood vessels as shown with RECA staining (rat endothelial cell antigen).
Figure 19:
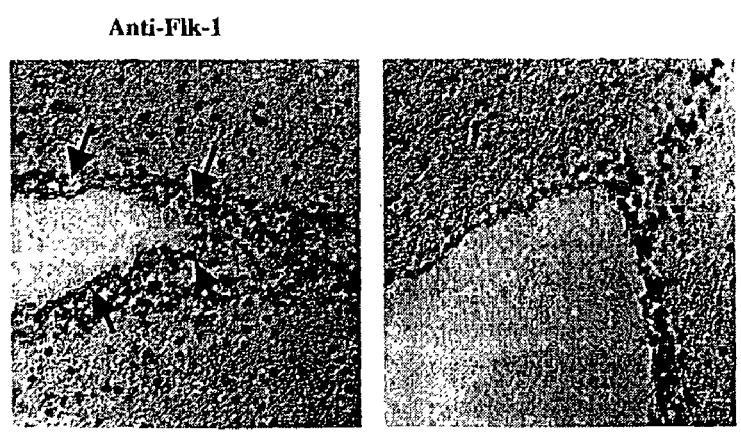
FIG. 19 shows the localization of Flk-1 immunoreactive cells in the ventricle wall. The ependymal layer of the ventricle wall shows intense immunoreactivity for Flk-1. Since neural stem cells can be generated from ependymal cells of the ventricle wall, Flk-1 could function as a stem cell marker and has perhaps a function in stem cell recruitment.

Localization of the VEGF Receptor Flk-1 in the Ventricle Wall of the Adult Brain FIG. 17 depicts neurogenesis in the hippocampus which is characterized by proliferative clusters of cells along the border between the granule cell layer (g) and the hilus region (h). These cells begin to migrate into the granule cell layer about 1 week after their last cell division and can be colabeled with markers for granule cells (e.g., NeuN and Calbindin). The VEGF receptor Flk-1 is highly expressed in the lateral dentate gyrus and ventricle wall (FIGS. 18 and 19, respectively). Immunostaining suggested localization in the ependymal layer (FIGS. 18 and 19). Ependymal cells also express Notch-1, which plays an important role in determining the neural fate of ectodermal cells (Johansson et al., 1999). Isolated individual ependymal cells can form neural stem cell (neurospheres) in culture (Johansson et al., 1999).

Example 9

Stimulation of Adult Neurogenesis by VEGF-Infusion

Figure 20:
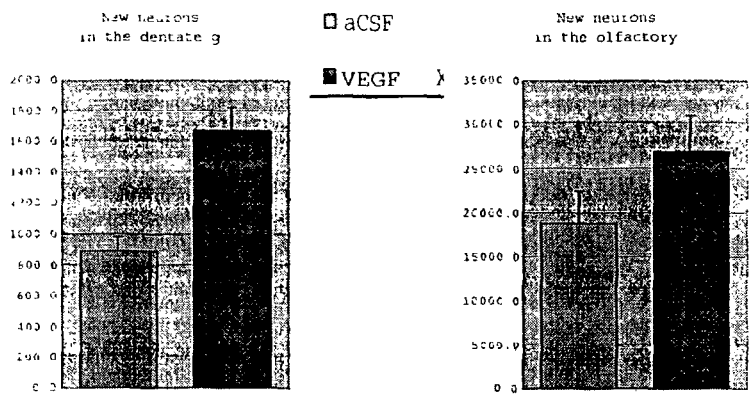
FIG. 20 represents intracerebroventricular infusion of VEGF. VEGF was infused via osmotic minipumps for 7 days into the lateral ventricle of adult rats. Increased BrdU labeling in the granule cell layer of the dentate gyrus is observed 4 weeks after infusion of VEGF into the lateral ventricle.

In a first experiment it was shown that neuronal production in the adult hippocampus is stimulated by infusion of VEGF into the lateral ventricle. Here, proliferating cells were labeled with BrdU during 7 days of continuous VEGF infusion. Four weeks later, when the newborn cells have differentiated into granule cells, a marked increase in BrdU labeled cells is observed in the dentate gyrus (FIG. 20). It can be inferred from this result that VEGF is a potent activator of neurogenesis in the adult brain.

Example 10

Expression of VEGF and Flk-1 in Neural Stem Cell Cultures

Figure 21:
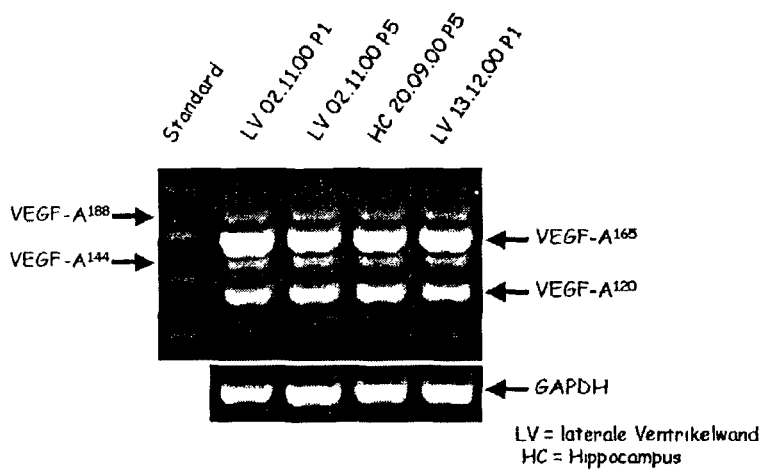
FIG. 21 shows VEGF mRNA levels. Neurospheres were cultured in a defined medium in the presence of EGF and FGF. Using RT-PCR, the MRNA from these cells was examined for the expression of 4 different isoforms of VEGF. GADPH expression served as quality control of the mRNA.
Figure 22:
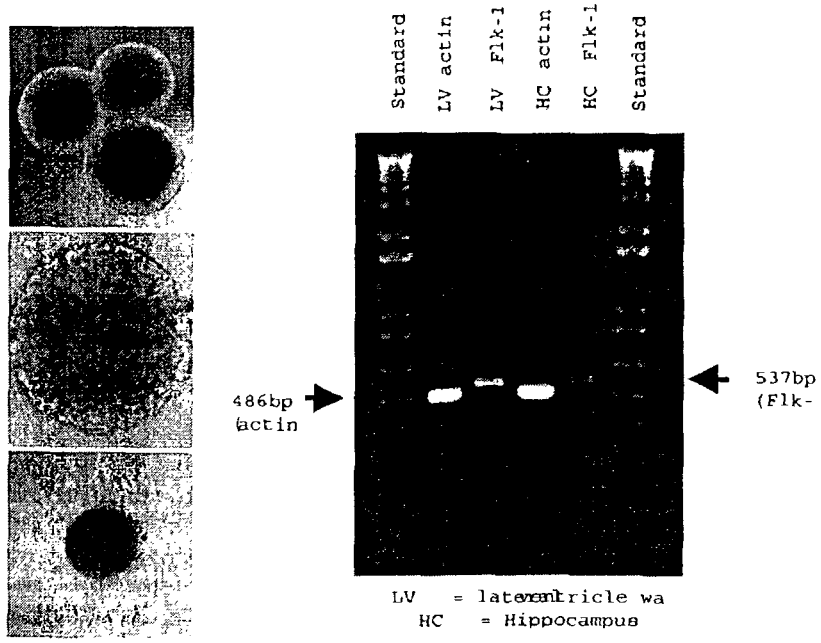
FIG. 22 shows Flk-1 mRNA levels. Left. Neural stem cells from the lateral ventricle wall (LV) and hippocampus (HC) of the adult rodent can be grown as neurospheres using defined medium and the growth factors FGF-2 and EGF. Right. From spheres under growth condition mRNA was isolated and RT-PCT for Flk-1 was performed. Actin was used as a control for mRNA amount.
Figure 23:
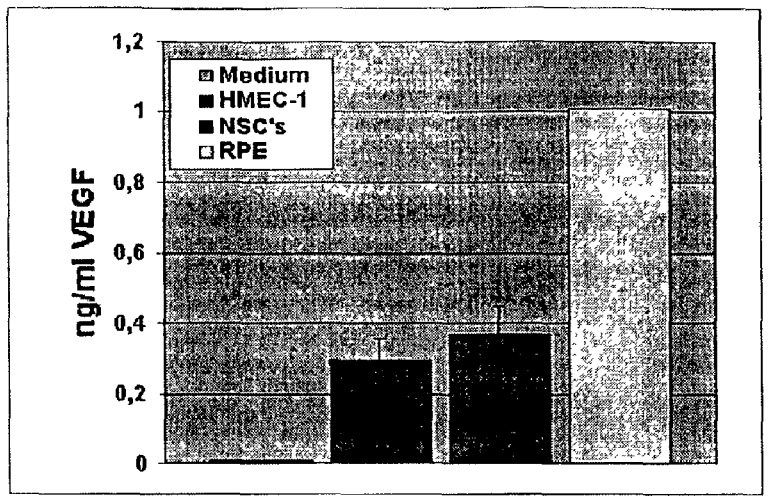
FIG. 23 shows the release of VEGF protein. Competitive ELISA for quantification of VEGF-secretion was used on adult NSCs from the rat lateral ventricle wall. As a positive control, the endothelial cell line HMEC-1 and primary retinal pigment epithelial cells (RPE) were used.

In order to analyze the functional consequences of VEGF stimulation in culture, it is important to know whether Flk-1 is expressed in neural stem cell cultures. Using RT-PCR we were recently able to show that neural stem cell cultures (neurospheres) from the ventricle wall and from the hippocampus express VEGF mRNA (FIG. 21) and Flk-1 mRNA (FIG. 22). Moreover, VEGF release was detected by Elisa assay (FIG. 23). This result shows that VEGF has an autocrine function in neural stem cell cultures. In FIG. 21, it was described, by using RT-PCR, that isoforms of VEGF are expressed by neurospheres when cultured in the presence of EGF and FGF. GADPH was used as a quality control of the mRNA.

Example 11

VEGF in Neural Stem Cell Cultures

Neural stem cells were prepared according to the attached protocol. Cells were grown in serum-free medium, subcloned and used between passage 6 and 10. If not otherwise mentioned the experiments consisted of triplets for analysis and were independently repeated at least 3 times.

Basal Medium: Neurobasal medium (NB, Gibco BRL) & B27 supplement (Gibco BRL).

Growth Medium: NB, B27 supplement+20 ng/ml of FGF-2 (R&D Systems)+20 ng/ml EGF (R&D Systems)+2 μg/ml heparin (Sigma, Germany).

Cells were plated in Growth medium at 10.000 cells/ml and after 2 days switched to the experimental condition. Cells were kept under the experimental condition for 7 days.

VEGF (mouse recombinant $VEGF_{164}$) was used at 50 ng/ml.

VEGF-Receptor Inhibitor PADQ (4-[(4-Chloro-2-fluoro) phenylamino-6,7-dimethoxyquinazoline, Calbiochem): A potent inhibitor of VEGF receptor (Flt-1 and Flk-1) tyrosine kinase activity. IC50=2.0 mM and 0.1 mM for Flt-1 and Flk-1, respectively. VEGFR-Inhibitor was used at 100 nM (IC50 for flk-1)

VEGF-Receptor Inhibitor SU1498—(E)-3-(3,5-Diisopropyl-4-hydroxyphenyl)-2-[(3-phenyl-n-propyl)amino-carbonyl]acrylonitrile (Calbiochem): A potent and selective inhibitor of the vascular endothelial growth factor (VEGF) receptor kinase Flk-1 (IC50=700 nM).

SU1498 has only a weak inhibitory effect on PDGF-receptor (IC50>50 mM), EGF-receptor (IC50>100 mM), and HER2 (IC50>100 mM) kinases.
SU1498 was used at 700 nM (IC50 for Flk-1).

Cell Culture Methods

Primary Cell Cultures for Growing Spheres of Neural Stem Cells From Adult Lateral Ventricle Wall Adult female Fischer-344 rats (3-4 months; Charles River, Germany) were killed via cervical dislocation, the brains of each rat were removed and stored at 4° C. in DPBS (PAN, Germany) with 4.5 g/L glucose (Merck, Germany) (DPBS/glu). Overlying meninges and blood vessels were removed. Ependymal zone including subependymal/subventricular zone form the lateral wall of the lateral ventricle were aseptically removed. The dissected tissue was transferred to fresh DPBS/glu, washed once, transferred to petri-dishes and dissociated mechanically into a single cell suspension. The cell suspension was washed in DPBS/glu in order to rinse off excess blood and resuspended in PPD-solution containing 0.01% Papain (Worthington Biochemicals, England), 0.1% dispase II (Boehringer, Germany), 0.01% DNase I (Worthington Biochemicals, England) and 12.4 mM $MgSO_4$ in HBSS (PAN, Germany) without $Mg^{++}/Ca^{++}$ (PAA, Germany) and digested for 30 to 40 min at room temperature. The cell solution was triturated every 10 min. Dissociated cells were collected and resuspended in serum-free DMEM/F12 medium containing 2 mM L-glutamine and 0.1 g/L penicillin/streptomycin and washed three times with accurate trituration with a blue tip. Finally the single cell suspension was resuspended in Neurobasal medium (Gibco BRL, Germany) supplemented with B27 (Gibco BRL, Germany) (NB/B27), 2 mM L-glutamine (PAN, Germany), 0.1 g/L penicillin/streptomycin (PAN, Germany), 2 µg/ml heparin (Sigma, Germany), 20 ng/ml bFGF-2 (R&D Systems, Germany) and 20 ng/ml EGF (R&D Systems, Germany). Live cells were counted by trypan blue exclusion assay in a hemocytometer. Cells were seeded in T-25 culture flasks and cultures were maintained at 37° C. in an incubator with 95% air, 5% $CO_2$. Single cells began to form spheres within 5 to 7 days of suspension culture and continued to grow in mass and number over the next weeks. Media were changed every 7 days.

Passaging of Cells

The culture medium containing floating neurospheres was collected in a 15 ml centrifuge tube and centrifuged at 800 rpm. The pellet was resuspended in 200 µl of Accutase (Innovative Cell Technologies Inc., USA, distributed by PAA, Germany) and triturated about 10 times using a pipette. Then, the cell suspension was incubated at 37° C. for 10 min. Dissociated spheres were again triturated and resuspended in 800 µl of NB/B27 medium. An aliquot was counted by trypan blue exclusion assay in a hemocytometer to determine the amount of live and dead cells. $1 \times 10^5$ cells were plated in T75 culture flasks for long term passaging (10 ml of culture medium per flask) in NB/B27 medium. The cells obtained after Accutase-treatment of primary neurospheres proliferated and yielded secondary neurospheres. Secondary neurospheres were passaged 7 to 9 days after plating primary neurosphere cells. Similar to primary cultures and primary neurospheres, single cells obtained after dissociation of secondary neurospheres proliferated and yielded tertiary neurospheres.

Proliferation Test

Various media and supplements were used to study the most optimal conditions for neural stem cell cultures. Neurobasal medium (Gibco BRL, Germany) or DMEM/F12 (1:1) medium (PAN, Germany) were either supplemented with B27 (Gibco BRL, Germany), N2 (Gibco BRL, Germany), or BIT9500 (StemCell Technologies Inc., Canada). Human low density lipoproteins (LDL, Sigma, Germany) were added to the BIT9500-containing media at a final concentration of 40 µg/µl according to the manufacturer. All media contained 2 mM L-glutamine, 0.1 g/L penicillin/streptomycin, 2 µg/ml heparin (Sigma, Germany), 20 ng/ml bFGF (R&D Systems, Germany), and 20 ng/ml EGF (R&D Systems, Germany). $1 \times 10^4$ cells per well were seeded in 12-well plates in a volume of 1 ml and grown under standard conditions. At day 7 the grown neurospheres were counted, dissociated by Accutase and live cells were counted by trypan blue exclusion assay in a hemocytometer.

BrdU ELISA

Neural stem cell were plated at 10000 cells/ml well and cultured for 7 days during which VEGF, PADQ or SU 1498 were added every second day. 24 hr before DNA isolation cells were pulsed with 5 µM BrdU. Cells were harvested and resuspended in 200 µl PBS. After treatment with 4 µl RNAse (100 mg/ml, Roche), DNA was isolated using the DNeasy KIT (Qiagen). After determining the concentration, DNA was treated with 0.25 M NaOH for 30 min. followed by 0.25 M HCL and buffering with 0.2 M $KH_2PO_4$ (pH 7). DNA was transferred to 96 wells plates (DNA Binding Plates, Costar) in a concentration series starting at 2 ng/µl and were incubated over night in the presence of 50 mM $Na_2HPO_4$. After washing in PBS, unspecific binding to the wells was blocked with 3% BSA/PBS for 30 min. With intermittent washes in PBS, a mouse anti BrdU antibody (Roche-Boehringer, 1:500) was incubated for 1 hr, followed by incubation with donkey-anti mouse POD (Jackson, 1:1000) for 1 hr. After PBS rinses developing reagent OPD was applied for 1 hr and the optical density was determined at 450 nm.

Clonally-Derived Cultures

Figure 26:
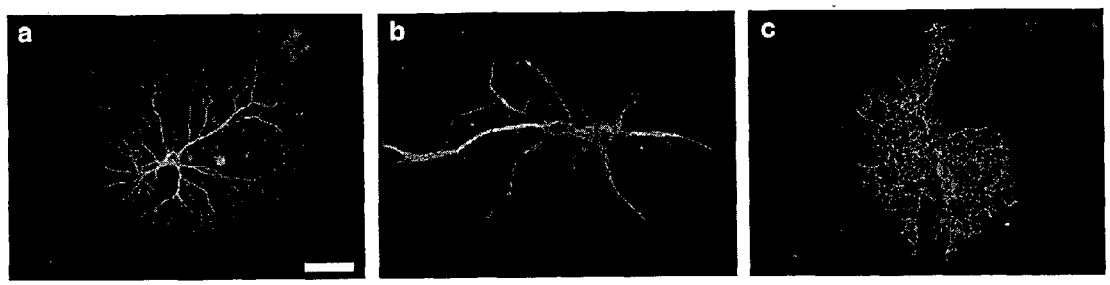
FIG. 26 shows the lineage potential of clonally-derived rat neural stem cell cultures. Individual clones derived from rat lateral ventricle wall cultured on poly-ornithin/laminin matrix were differentiated in NB/B27 medium supplemented with 1% FCS for 7 days and immunostained for the presence of (a) neurons with βIII-tubulin, (b) astrocytes with GFAP or (c) oligodendrocytes with GalC (bar=40 μm).

The in vitro effect of VEGF was analyzed using neural stem cells isolated from the lateral ventricle wall of the adult rat brain. Previously reported in vitro data on VEGF was derived from primary cultures. The analysis has now been repeated and extended using clonally-derived neural stem cells, thus excluding the possibility that VEGF acts on non-stem cell derived cells which could be present in the primary cell preparation. These clonally derived neural stem cells are multipotent and produce the three major cell types of the brain: neurons, astrocytes and oligodendrocytes (FIG. 26).

VEGF Stimulation in Neural Stem Cell Cultures

Figure 24:
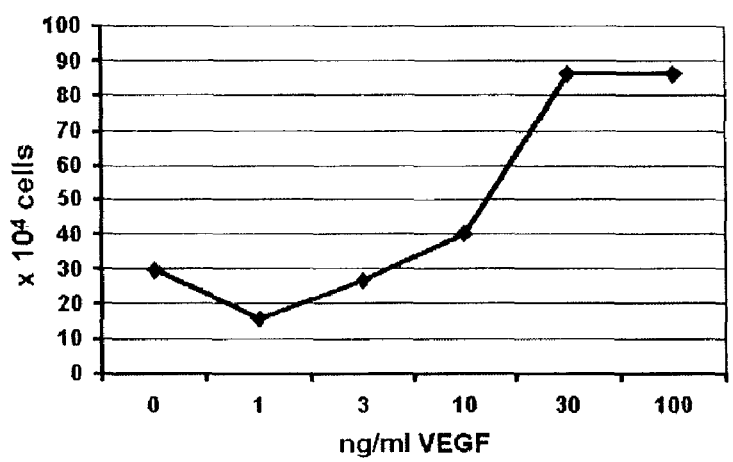
FIG. 24 depicts VEGF-dependent proliferation of NSCs. Neurosphere cultures were grown in serum free medium containing EGF/FGF-2. VEGF was added to this medium in different concentrations for 7 days and the total number of NSCs was counted.
Figure 25:
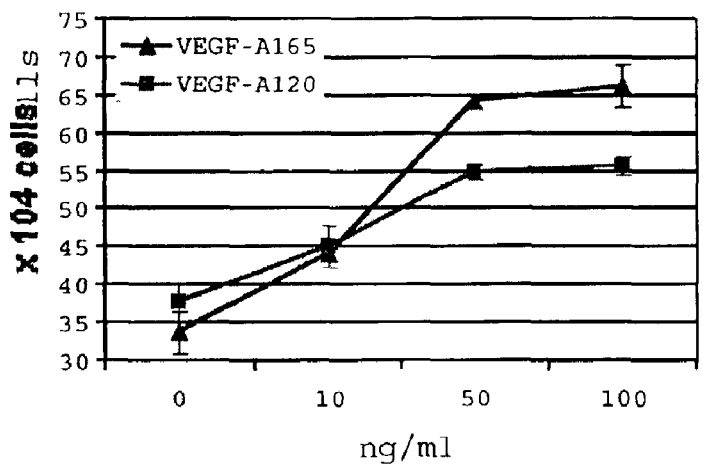
FIG. 25 shows that the effect of VEGF is modulated via the Flk-1 receptor. NSC cultures were stimulated for 7 days with different concentrations of VEGF-$A_{165}$ (triangle) and VEGF-$A_{121}$ (squares). VEGF-$A_{165}$ bind to all VEGF-receptors whereas VEGF-$A_{121}$ binds preferentially to the Flk-1 receptor.

VEGF has a dose-dependent stimulatory effect on the proliferation of neural stem cells from the adult rat brain (FIG. 24). Since VEGF can act via several receptors, two VEGF isoforms were compared, which have different receptor affinity. VEGF-$A_{165}$ can bind to flk-1, flt-1 and neuropilin-1 whereas VEGF-$A_{121}$ can only bind to the Flk-1 receptor. Both isoforms showed a significant stimulation of neural stem cell cultures, suggesting that the proliferation-enhancing effect of VEGF in neural stem cell cultures is mainly mediated by Flk-1 signaling (FIG. 25).

VEGF Effects on Neural Stem Cell Expansion

Figure 27:
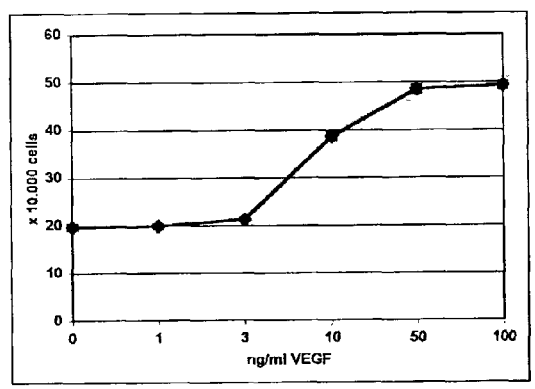
FIG. 27 is a Dose-Response-Curve for VEGF in rat neural stem cells from the adult lateral ventricle wall. The dose-response curve was performed on clonally derived neural stem cells. Maximal growth activity can be observed starting at 50 ng/ml.

When VEGF was added to the growth medium which already contains EGF and FGF-2 as mitogens, a 2.5 fold increase in the number of cells was observed after 7 days. The ED50 is in the range of 10 ng/ml and maximal stimulation was reached at 50 ng/ml (FIG. 27). VEGF is therefore a potent co-factor for the expansion of neural stem cell cultures.

Figure 28:
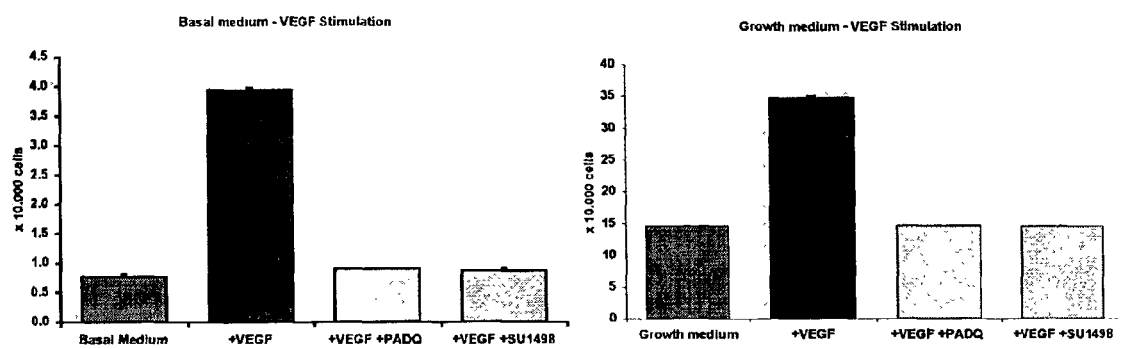
FIG. 28 (A) In basal medium VEGF (50 ng/ml) stimulates the expansion of neural stem cell cultures about 5-fold. The VEGF-Receptor inhibitors PADQ and SU1498 are both able to block the VEGF response at concentrations specific for VEGF receptor flk-1. Total cell counts at 7 days after treatment. (B) In growth conditions (including EGF and FGF-2), VEGF stimulates the expansion of neural stem cell cultures about 2-fold. The VEGF-Receptor tyrosine kinase inhibitors PADQ and SU1498 are both able to block the VEGF response. Total cell counts at 7 days after treatment in growth medium

When VEGF was added to the basal medium, a 5-fold increase in the number of cells was detected after 7 days (FIG. 28, left panel). Two VEGF receptor tyrosine kinase inhibitors were effective in blocking the VEGF effect at their respective ED50 concentration for Flk-1 (FIG. 28, left panel). These compounds were used at concentrations which specifically block the VEGF receptor Flk-1. Under growth conditions (Basal medium+EGF+FGF-2+heparin) the VEGF receptor antagonists were also able to block the effect of the exogenously applied VEGF (FIG. 28, right panel).

Endogenous VEGF Expression and Release

Figure 29:
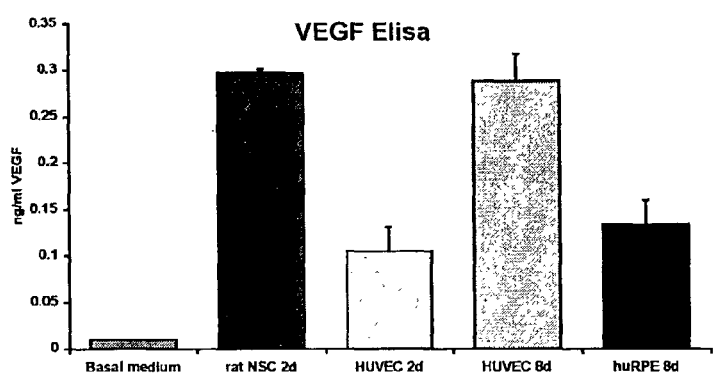
FIG. 29 shows VEGF production and release into the cell culture medium. Cells were cultured in serum free medium and medium was collected at 2 days (2 d) or 8 days (8 d) in medium. HUVEC: Human umbilical vein endothelial cells, huRPE: human retinal pigment epithelial cells.

It has been previously shown that Flk-1 is expressed in neural stem cell cultures. When determining the expression and release of VEGF into the culture medium of clonally-derived neural stem cell cultures (FIG. 29) it was found that rat neural stem cells are a prominent source of VEGF in comparison to other cell types, which are known to express VEGF. HUVEC cells needed about 8 days to produce the same amount of VEGF and human retinal pigment epithelial cells produced substantially less.

Figure 30:
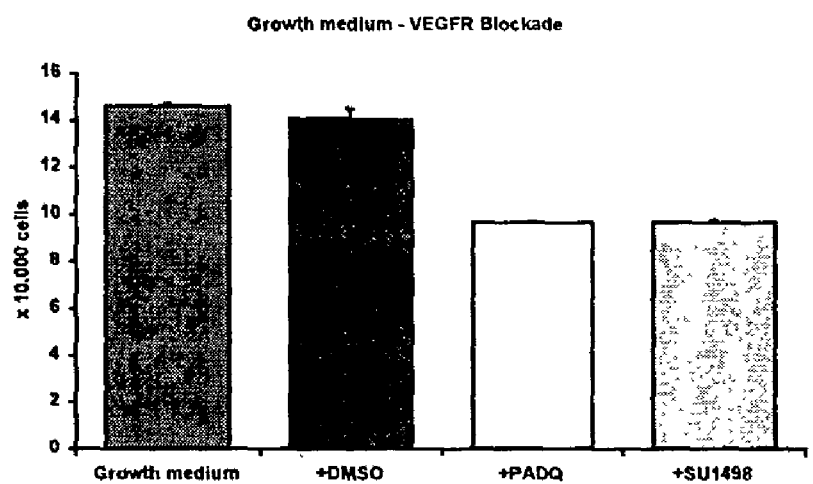
FIG. 30 represents NSCs under growth conditions (with EGF and FGF-2) VEGF-receptor-Tyrosine kinase receptor blocker PADQ and SU1498 are both able to significantly reduce the growth of neural stem cell cultures. DMSO was used to dissolve the inhibitors and had no effect on the growth rate. Total cell counts at 7 days after treatment.

Since Flk-1 is present and VEGF is spontaneously released into the medium by neural stem cells, it was tested whether VEGF and its receptor Flk-1 play an endogenous role in the expansion of neural stem cell cultures. When VEGF receptor inhibitors were added to the growth medium containing recombinant EGF and FGF-2 but no recombinant VEGF, a 30% reduced growth rate was observed (FIG. 30). These data suggest that EGF and FGF-2 exert their ability to expand neural stem cell cultures in part through the production and release of VEGF.

Mechanism of VEGF Action in Vivo

Figure 31:
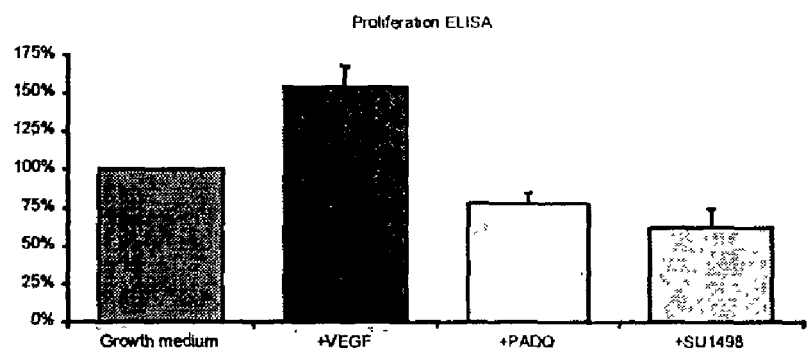
FIG. 31 shows that BrdU incorporation is increased under VEGF and reduced under VEGF receptor blockade. Neural stem cell cultures were treated with 50 ng/ml VEGF, 100 nM PADQ or 700 nM SU1498 for 7 days. BrdU (10 μM) was added to the culture medium 24 hrs before cells were harvested and lysed. DNA was extracted and BrdU content was determined using an anti-BrdU-ELISA. The data are presented as percent changes in optical density compared to control (Growth medium).

In order to determine whether the enhanced expansion of neural stem cultures under VEGF is due to increased proliferation or reduced cell death, neural stem cells were analyzed using a proliferation ELISA (see experimental details) and an apoptosis ELISA (Cell Death Detection ELISA, Roche Applied Sciences) according to the manufacturers protocol. Cells grown in the presence of VEGF incorporated more BrdU and in the presence of VEGF receptor blockers less BrdU (FIG. 31), suggesting that VEGF stimulates proliferation in vitro.

Figure 32:
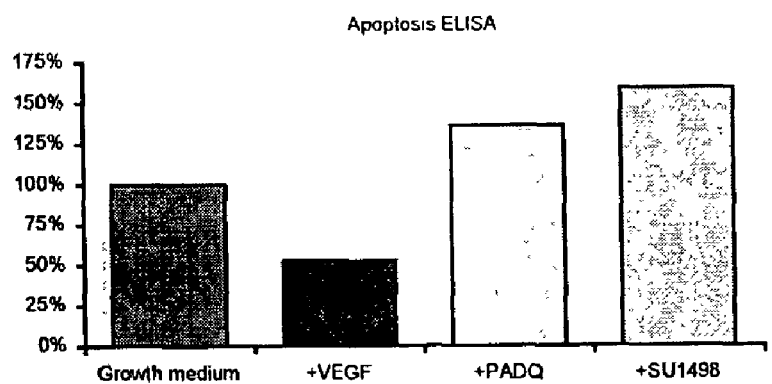
FIG. 32 shows that DNA fragementation is increased under VEGF and reduced under VEGF receptor blockade. Neural stem cell cultures were treated with 50 ng/ml VEGF, 100 nM PADQ or 700 nM SU1498 for 7 days. BrdU (10 μM) was added to the culture medium 24 hrs before cells were harvested and lysed. DNA was extracted and BrdU content was determined using an anti-BrdU-ELISA. The data are presented as percent changes in optical density compared to control (Growth medium).

However, using an apoptosis ELISA, an anti-apoptotic activity was also detected, since VEGF reduced the amount of DNA strand breaks, a hallmark of apoptotic cell death, whereas VEGFR blocker increased the DNA strand breaks (FIG. 32).

VEGF can exert both a proliferative and survival-promoting effect. FGF-2 has been previously shown to promote neuronal survival at a lower concentration (0.5-1 ng/ml) and to promote proliferation of neural stem cells and progenitors at a higher concentration (10-20 ng/ml, see Ray et al. 1993, PNAS 90:3602-3606). VEGF could act in a similar dose-dependent manner.

Increased Efficiency to Generate Neural Stem Cell Cultures After VEGF Infusion

Figure 33:
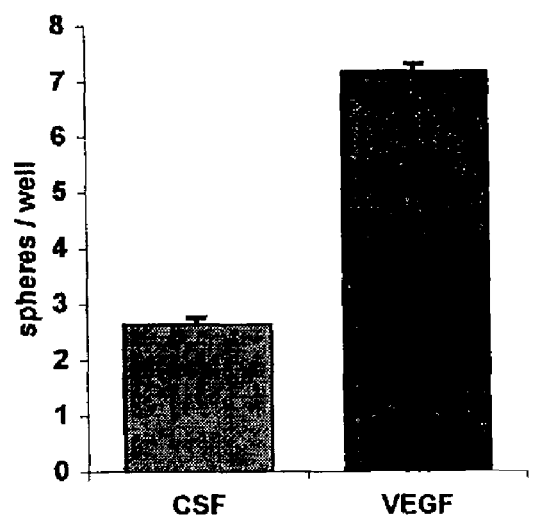
FIG. 33 represents in vitro generation of spheres is stimulated by intraventricular VEGF infusion. After 7 days of intraventricular infusion of either artificial cerebrospinal fluid (CSF) or VEGF, cells were isolated from the lateral ventricle wall, seeded at 10000 cells/well in Growth medium (Neurobasal+B27+EGF+FGF-2+heparin) and grown in culture for 3 weeks. The efficiency to generate spheres from the lateral ventricle wall is substantially increased by previous in vivo infusion of VEGF. It was concluded from this finding, that VEGF stimulates the multipotent neural stem cells of the lateral ventricle wall in vivo leading to a facilitated neural stem cell growth in vitro.

VEGF was infused into the lateral ventricle of adult rats. After isolating and seeding cells from the lateral ventricle wall in order to establish neural tem cell cultures, the number of spheres that formed after several weeks was significantly increased in cultures from VEGF-treated animals compared to aCSF controls (FIG. 33).

Overall, the results showed that VEGF and the VEGF receptor Flk-1 are expressed in vivo in close spatial relation to sites of neurogenesis. VEGF and the VEGF receptor Flk-1 are expressed in vitro in clonally-derived neural stem cell cultures. VEGF increased the generation of new neurons in vivo and the expansion of neural stem cell in vitro. Blocking the endogenous VEGF receptor signaling diminished the ability to expand neural stem cell cultures. Proliferation as well as cell survival were promoted by VEGF and reduced after blocking VEGF receptor signaling. It is therefore concluded that endogenously produced VEGF acts in an auto- or paracrine fashion to promote neural stem and progenitor cell growth/survival in vitro and the generation of neurons in vivo.

Example 11

Expression in Neural Stem Cells.

Human Stem Cell (HSC) Cultures

A biopsy from the anterior lateral wall of the lateral ventricle was taken from an adult human patient and enzymatically dissociated in Papain, Dispase and Dnase I in DMEM containing 4.5 mg/ml glucose and 37° C. for 20 min. The cells were gently triturated and mixed with three volumes of Human Stem Cell Plating Medium (HSCPM) (DMEM/F12; 10% FBS). The cells were pelleted at 250×g for 5 min. The supernatant was subsequently removed and the cells resuspended in HSCPM, plated out on fibronectin coated culture dishes and incubated at 37° C. in 5% $CO_2$. The following day the expansion of the culture was initiated by change of media to HSC culture media (DMEM/F12; BIT 9500; EGF 20 ng/ml; FGF2 20 ng/ml). The HSC were split using trypsin and EDTA under standard conditions. FBS was subsequently added to inhibit the reaction and the cells collected by centrifugation at 250×g for 5 min. The HSC were replated in HSC culture media.

RT-PCR

The following primer pairs were designed to specifically identify the presence of vegf, flt-1, flt-4, and flk-1 gene expression in HSC cultures. Estimated band sizes for each primer pair are given below:

|  |  | Band size (base pairs) |
|---|---|---|
| VEGF | ttgggtgcattggagccttg (SEQ ID NO:17) | 327 |
|  | tggccttggtgaggtttgatc (SEQ ID NO:18) |  |
|  | ttgggtgcattggagccttg (SEQ ID NO:19) | 434 |
|  | tgagcaaggcccacagggat (SEQ ID NO:20) |  |
| FLT-1 | agatgtccaaataagcacaccacgc (SEQ ID NO:21) | 347 |
|  | tttcaagcacctgctgttttcga (SEQ ID NO: 22) |  |
|  | agatgtccaaataagcacaccacgc (SEQ ID NO:23) | 470 |
|  | ccacgagtcaaatagcgagcagatt (SEQ ID NO:24) |  |
| FLT-4 | catccagctgttgcccagga (SEQ ID NO:25) | 378 |
|  | ttcacgggcagcttcaccag (SEQ ID NO: 26) |  |
| FLK-1 | atgatgtggttctgagtccgtctca (SEQ ID NO:27) | 409 |
|  | gggggtgggtaaccaaggtactt (SEQ ID NO:28) |  |
|  | atgatgtggttctgagtccgtctca (SEQ ID NO:29) | 476 |
|  | catgccccgctttaattgtgtg (SEQ ID NO:30) |  |

Human stem cells were prepared and cultured as stated above. Total RNA isolated using Qiagen's RNeasy Mini Kit according to the manufacturer's instructions and DNase treated using Ambion Dnase I and according to protocol. Life Technology's One-Step RT-PCR Kit was used to detect the presence of vegf, flt-1, flt-4 and flk-1 mRNA. Briefly, 100 ng of total RNA was used in each reaction, with an annealing temperature of 54° C. To further ensure that genomic contamination of the total RNA did not give rise to false positive results, an identical reaction in which the RT-taq polymerase mix was replaced by taq polymerase alone and was run in parallel with the experimental RT-PCR. The reactions were electrophoresed on a 1.5% agarose gel containing ethidium bromide and the bands visualised under UV light.

VEGF and FLT-4 Genes are Expressed in Cultured Human Neural Stem Cells

Figure 34:
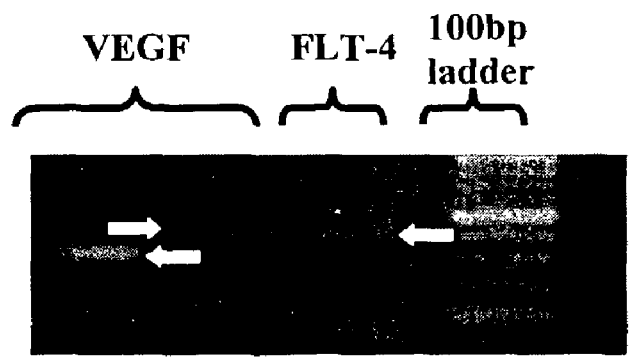
FIG. 34 shows that the VEGF and FLT-4 genes are expressed in cultured human neural stem cells.

RT-PCR was performed on total RNA prepared from cultured HSC using primer pairs specific for the above genes. The bands indicated with a white arrow correspond to the bands of the desired size (VEGF [lane 1, 327 bp; lane 2, 434 bp], FLT-4 [lane 3, 378 bp]), verifying that they represent correct product (FIG. 34). A parallel control experiment without using any reverse transcriptase, only taq polymerase, ruled out false positive bands through genomic contamination (data not shown).

FLT-1 and FLK-1 Genes are Expressed in Cultured Human Neural Stem Cells

Figure 35:
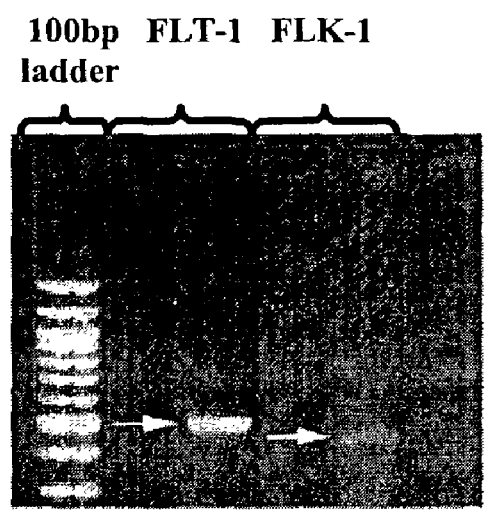
FIG. 35 shows that the FLT-1 and FLK-1 genes are expressed in cultured human neural stem cells.

RT-PCR was performed on total RNA prepared from cultured HSC using primer pairs specific for the above genes. The bands indicated with an arrow correspond to the bands of the desired size (FLT-1 [lane 2, 470 bp], FLK-1 [lane 4, 476 bp]), verifying that they represent correct product (FIG. 35).

Those skilled in the art will recognize, or be able to ascertain using no more than routine experimentation, many equivalents to the specific embodiments of the invention specifically described herein. Such equivalents are intended to be encompassed in the scope of the following claims.

We claim:

1. A method of treating a patient with Parkinson's disease or Parkinsonian disorders comprising administering PDGF-BB in vivo directly to the central nervous system of said patient, wherein the PDGF-BB is administered in an amount of between 0.5 ng/kg/day to 500 ng/kg/day.

2. A method for inducing the in situ proliferation or differentiation of neural stem cells or neural progenitor cells located in a neural tissue of a human, the method comprising administering an amount of PDGF-BB of between 0.5 ng/kg/day to 500 ng/kg/day, to the neural tissue to induce the proliferation or differentiation of the neural stem cells or neural progenitor cells.

3. A method of increasing the number of dopaminergic neurons in a patient suffering from Parkinson's disease or Parkinsonian disorders comprising the step of infusing the central nervous system of said patient with an amount of PDGF-BB of between 0.5 ng/kg/day to 500 ng/kg/day to increase the number of dopaminergic neurons.

4. The method of claim 1 wherein said method induces the differentiation, migration, proliferation or survival of neural stem cells or neural progenitor cell in said patient.

5. The method of claim 1 wherein said PDGF-BB is administered intracerebroventricularly, intraparenchymally, intrathecally, intracranially or nasally.

6. The method of claim 2 wherein said PDGF-BB is administered intracerebroventricularly, intraparenchymally, intrathecally, intracranially or nasally.

7. The method of claim 3 wherein said PDGF-BB is administered intracerebroventricularly, intraparenchymally, intrathecally, intracranially or nasally.

8. A method of treating a patient with Parkinson's disease or Parkinsonian disorders comprising administering PDGF-BB in vivo directly to the central nervous system of said patient, wherein the PDGF-BB is administered in an amount of between 0.1 ng/kg/day to 1 μg/kg/day.

9. The method of claim 8 wherein said method induces the differentiation, migration, proliferation or survival of neural stem cells or neural progenitor cell in said patient.

10. The method of claim 8 wherein said PDGF-BB is administered intracerebroventricularly, intraparenchymally, intrathecally, intracranially or nasally.

11. A method for inducing the in situ proliferation or differentiation of neural stem cells or neural progenitor cells located in a neural tissue of a human, the method comprising administering an amount of PDGF-BB of between 0.1 ng/kg/day to 1 μg/kg/day, to the neural tissue to induce the proliferation or differentiation of the neural stem cells or neural progenitor cells.

12. The method of claim 11 wherein said PDGF-BB is administered intracerebroventricularly, intraparenchymally, intrathecally, intracranially or nasally.

13. A method of increasing the number of dopaminergic neurons in a patient suffering from Parkinson's disease or Parkinsonian disorders comprising the step of infusing the central nervous system of said patient with an amount of PDGF-BB of between 0.1 ng/kg/day to 1 μg/kg/day to increase the number of dopaminergic neurons.

14. The method of claim 13 wherein said PDGF-BB is administered intracerebroventricularly, intraparenchymally, intrathecally, intracranially or nasally.

* * * * *

SEQUENCE LISTING

```
<160> NUMBER OF SEQ ID NOS: 32

<210> SEQ ID NO 1
<211> LENGTH: 2797
<212> TYPE: DNA
<213> ORGANISM: Homo sapiens

<400> SEQUENCE: 1
acgcgcgccc tgcggagccc gcccaactcc ggcgagccgg gcctgcgcct actcctcctc      60
ctcctctccc ggcggcggct gcggcggagg cgccgactcg gccttgcgcc cgccctcagg     120
cccgcgcggg cggcgcagcg aggccccggg cggcgggtgg tggctgccag gcggctcggc     180
cgcgggcgct gcccggcccc ggcgagcgga gggcggagcg cggcgccgga gccgagggcg     240
cgccgcggag ggggtgctgg gccgcgctgt gcccggccgg cggcggctg caagaggagg     300 ccggaggcga gcgcggggcc ggcggtgggc gcgcagggcg gctcgcagct cgcagccggg     360
gccgggccag gcgttcaggc aggtgatcgg tgtggcggcg gcggcggcgg cggccccaga     420
ctccctccgg agttcttctt ggggctgatg tccgcaaata tgcagaatta ccggccgggt     480
cgctcctgaa gccagcgcgg ggagcgagcg cggcggcggc cagcaccggg aacgcaccga     540
ggaagaagcc cagcccccgc cctccgcccc ttccgtcccc accccctacc cggcggccca     600
ggaggctccc cggctgcggc gcgcactccc tgtttctcct cctcctggct ggcgctgcct     660
gcctctccgc actcactgct cgccgggcgc cgtccgccag ctccgtgctc cccgcgccac     720
cctcctccgg gccgcgctcc ctaagggatg gtactgaatt tcgccgccac aggagaccgg     780
ctggagcgcc cgccccgcgc ctcgcctctc ctccgagcag ccagcgcctc gggacgcgat     840
gaggaccttg gcttgcctgc tgctcctcgg ctgcggatac ctcgcccatg ttctggccga     900
ggaagccgag atccccgcg aggtgatcga gaggctggcc cgcagtcaga tccacagcat     960
ccgggacctc cagcgactcc tggagataga ctccgtaggg agtgaggatt ctttggacac    1020
cagcctgaga gctcacgggg tccacgccac taagcatgtg cccgagaagc ggcccctgcc    1080
cattcggagg aagagaagca tcgaggaagc tgtccccgct gtctgcaaga ccaggacggt    1140
catttacgag attcctcgga gtcaggtcga ccccacgtcc gccaacttcc tgatctggcc    1200
cccgtgcgtg gaggtgaaac gctgcaccgg ctgctgcaac acgagcagtg tcaagtgcca    1260
gccctcccgc gtccaccacc gcagcgtcaa ggtggccaag gtggaatacg tcaggaagaa    1320
```

```
gccaaaatta aaagaagtcc aggtgaggtt agaggagcat ttggagtgcg cctgcgcgac    1380
cacaagcctg aatccggatt atcgggaaga ggacacggga aggcctaggg agtcaggtaa    1440
aaaacggaaa agaaaaaggt taaaacccac ctaagatgtg aggtgaggat gagccgcagc    1500
cctttcctgg gacatggatg tacatggcgt gttacattcc tgaacctact atgtacggtg    1560
ctttattgcc agtgtgcggt ctttgttctc ctccgtgaaa aactgtgtcc gagaacactc    1620
gggagaacaa agagacagtg cacatttgtt taatgtgaca tcaaagcaag tattgtagca    1680
ctcggtgaag cagtaagaag cttccttgtc aaaagagag agagagagag agagagagaa     1740
aacaaaacca caaatgacaa aaacaaaacg gactcacaaa aatatctaaa ctcgatgaga    1800
tggagggtcg ccccgtggga tggaagtgca gaggtctcag cagactggat ttctgtccgg    1860
gtggtcacag gtgctttttt gccgaggatg cagagcctgc tttgggaacg actccagagg    1920
ggtgctggtg ggctctgcag ggcccgcagg aagcaggaat gtcttggaaa ccgccacgcg    1980
aactttagaa accacacctc ctcgctgtag tatttaagcc catacagaaa ccttcctgag    2040
agccttaagt ggttttttt tttgtttttg ttttgttttt tttttttttg tttttttttt      2100
tttttttttt tttacacca taaagtgatt attaagcttc cttttactct ttggctagct      2160
tttttttttt tttttttttt tttttttttt aattatctct tggatgacat ttacaccgat    2220
aacacacagg ctgctgtaac tgtcaggaca gtgcgacggt attttttccta gcaagatgca     2280 aactaatgag atgtattaaa ataaacatgg tatacctacc tatgcatcat ttcctaaatg    2340
tttctggctt tgtgtttctc ccttaccctg ctttatttgt taatttaagc cattttgaaa    2400
gaactatgcg tcaaccaatc gtacgccgtc cctgcggcac ctgccccaga gcccgtttgt    2460
ggctgagtga caacttgttc cccgcagtgc acacctagaa tgctgtgttc ccacgcggca    2520
cgtgagatgc attgccgctt ctgtctgtgt tgttggtgtg ccctggtgcc gtggtggcgg    2580
tcactccctc tgctgccagt gtttggacag aacccaaatt cttttatttt ggtaagatat    2640
tgtgctttac ctgtattaac agaaatgtgt gtgtgtggtt tgtttttttg taaaggtgaa    2700
gtttgtatgt ttacctaata ttacctgttt tgtatacctg agagcctgct atgttcttct    2760
tttgttgatc caaaattaaa aaaaaaatac caccaac                             2797
```

<210> SEQ ID NO 2
<211> LENGTH: 3373
<212> TYPE: DNA
<213> ORGANISM: Homo sapiens

<400> SEQUENCE: 2

```
ggtggcaact tctcctcctg cggccgggag cggcctgcct gcctccctgc gcacccgcag      60
cctcccccgc tgcctcccta gggctcccct ccggccgcca gcgccatttt ttcattccct     120
agatagagat actttgcgcg cacacacata catacgcgcg caaaaaggaa aaaaaaaaa     180 aaaagcccac cctccagcct cgctgcaaag agaaaaccgg agcagccgca gctcgcagct    240
cgcagctcgc agcccgcagc ccgcagagga cgcccagagc ggcgagcagg cgggcagacg    300
gaccgacgga ctcgcgccgc gtccacctgt cggccgggcc cagccgagcg cgcagcgggc    360
acgccgcgcg cgcggagcag ccgtgcccgc cgcccgggcc cgccgccagg gcgcacacgc    420
tcccgccccc ctaccggcc cgggcggag tttgcacctc tccctgcccg ggtgctcgag       480
ctgccgttgc aaagccaact ttggaaaaag ttttttgggg gagacttggg ccttgaggtg    540
cccagctccg cgctttccga ttttggggc ctttccagaa aatgttgcaa aaagctaag      600 ccggcgggca gaggaaaacg cctgtagccg gcgagtgaag acgaaccatc gactgccgtg    660
```

```
ttccttttcc tcttggaggt tggagtcccc tgggcgcccc cacacggcta gacgcctcgg      720
ctggttcgcg acgcagcccc ccggccgtgg atgctgcact cgggctcggg atccgcccag      780
gtagccggcc tcggacccag gtcctgcgcc caggtcctcc cctgccccc  agcgacggag      840 ccggggccgg gggcggcggc gccggggggca tgcgggtgag ccgcggctgc agaggcctga     900
gcgcctgatc gccgcggacc tgagccgagc ccacccccct ccccagcccc ccaccctggc      960
cgcgggggcg cgcgctcga tctacgcgtc cggggcccg  cggggccggg cccggagtcg      1020
gcatgaatcg ctgctgggcg ctcttcctgt ctctctgctg ctacctgcgt ctggtcagcg     1080
ccgaggggga ccccattccc gaggagcttt atgagatgct gagtgaccac tcgatccgct     1140
cctttgatga tctccaacgc ctgctgcacg agaccccgg  agaggaagat ggggccgagt     1200
tggacctgaa catgcccgc  tcccactctg gaggcgagct ggagagcttg gctcgtggaa     1260
gaaggagcct gggttccctg accattgctg agccggccat gatcgccgag tgcaagacgc     1320
gcaccgaggt gttcgagatc tcccggcgcc tcatagaccg caccaacgcc aacttcctgg     1380
tgtggccgcc ctgtgtggag gtgcagcgct gctccggctg ctgcaacaac cgcaacgtgc     1440
agtgccgccc cacccaggtg cagctgcgac ctgtccaggt gagaaagatc gagattgtgc     1500
ggaagaagcc aatcttttaag aaggccacgg tgacgctgga agaccacctg gcatgcaagt     1560
gtgagacagt ggcagctgca cggcctgtga cccgaagccc gggggttcc  caggagcagc     1620 gagccaaaac gccccaaact cgggtgacca ttcggacggt gcgagtccgc cggcccccca     1680
agggcaagca ccggaaattc aagcacacgc atgacaagac ggcactgaag gagacccttg     1740
gagcctaggg gcatcggcag gagagtgtgt gggcagggtt atttaatatg gtatttgctg     1800
tattgccccc atggggtcct tggagtgata atattgtttc cctcgtccgt ctgtctcgat     1860
gcctgattcg gacggccaat ggtgcttccc ccaccctcc  acgtgtccgt ccacccttcc     1920
atcagcgggt ctcctcccag cggcctccgg tcttgcccag cagctcaaag aagaaaaaga     1980
aggactgaac tccatcgcca tcttcttccc ttaactccaa gaacttggga taagagtgtg     2040
agagagactg atggggtcgc tctttggggg aaacgggttc cttcccctgc acctggcctg     2100
ggccacacct gagcgctgtg gactgtcctg aggagccctg aggacctctc agcatagcct     2160
gcctgatccc tgaacccctg gccagctctg aggggaggca cctccaggca ggccaggctg     2220
cctcggactc catggctaag accacagacg ggcacacaga ctggagaaaa cccctcccac     2280
ggtgcccaaa caccagtcac ctcgtctccc tggtgcctct gtgcacagtg gcttctttc     2340 gttttcgttt tgaagacgtg gactcctctt ggtgggtgtg ccagcacac  caagtggctg     2400 ggtgccctct caggtgggtt agagatggag tttgctgttg aggtggtgta gatggtgacc     2460
tgggtatccc ctgcctcctg ccacccctttc ctccccatac tccactctga ttcacctctt     2520
cctctggttc ctttcatctc tctacctcca ccctgcattt tcctcttgtc ctggcccttc     2580
agtctgctcc accaagggc  tcttgaaccc cttattaagg cccagatga  ccccagtcac     2640 tcctctctag ggcagaagac tagaggccag ggcagcaagg gacctgctca tcatattcca     2700
acccagccac gactgccatg taaggttgtg cagggtgtgt actgcacaag gacattgtat     2760
gcagggagca ctgttcacat catagataaa gctgatttgt atatttatta tgacaatttc     2820
tggcagatga aggtaaagag gaaaaggatc cttttcctaa ttcacacaaa gactccttgt     2880
ggactggctg tgcccctgat gcagcctgtg gctgagtgg  ccaaatagga gggagactgt     2940
ggtaggggca gggaggcaac actgctgtcc acatgacctc catttcccaa agtcctctgc     3000
tccagcaact gcccttccag gtgggtgtgg gacacctggg agaaggtctc caagggaggg     3060
```

```
tgcagccctc ttgcccgcac ccctccctgc ttgcacactt ccccatcttt gatccttctg    3120
agctccacct ctggtggctc ctcctaggaa accagctcgt gggctgggaa tgggggagag    3180
aagggaaaag atccccaaga ccccctgggg tgggatctga gctcccacct cccttcccac    3240
ctactgcact ttccccttc ccgccttcca aaacctgctt ccttcagttt gtaaagtcgg    3300
tgattatatt tttgggggct ttcctttat ttttaaatg taaaatttat ttatattccg     3360
tatttaaagt tgt                                                       3373

<210> SEQ ID NO 3
<211> LENGTH: 1804
<212> TYPE: DNA
<213> ORGANISM: Homo sapiens

<400> SEQUENCE: 3
ggcacgagga ttatgtggaa actaccctgc gattctctgc tgccagagca ggctcggcgc      60
ttccacccca gtgcagcctt cccctggcgg tggtgaaaga gactcgggag tcgctgcttc     120
caaagtgccc gccgtgagtg agctctcacc ccagtcagcc aaatgagcct cttcgggctt     180
ctcctgctga catctgccct ggccggccag agacagggga ctcaggcgga tccaacctg     240 agtagtaaat tccagttttc cagcaacaag gaacagaacg gagtacaaga tcctcagcat    300
gagagaatta ttactgtgtc tactaatgga agtattcaca gcccaaggtt tcctcatact    360
tatccaagaa atacggtctt ggtatggaga ttagtagcag tagaggaaaa tgtatggata    420
caacttacgt ttgatgaaag atttgggctt gaagacccag aagatgacat atgcaagtat    480
gattttgtag aagttgagga acccagtgat ggaactatat tagggcgctg gtgtggttct    540
ggtactgtac caggaaaaca gatttctaaa ggaaatcaaa ttaggataag atttgtatct    600
gatgaatatt ttccttctga accagggttc tgcatccact acaacattgt catgccacaa    660
ttcacagaag ctgtgagtcc ttcagtgcta ccccttcag cttgccact ggacctgctt     720 aataatgcta taactgcctt tagtaccttg aagaccttag ttcgatatct tgaaccagag    780
agatggcagt tggacttaga agatctatat aggccaactt ggcaacttct tggcaaggct    840
tttgtttttg gaagaaaatc cagagtggtg atctgaacc ttctaacaga ggaggtaaga    900
ttatacagct gcacacctcg taacttctca gtgtccataa gggaagaact aaagagaacc    960
gataccattt tctggccagg ttgtctcctg gttaaacgct gtggtgggaa ctgtgcctgt   1020
tgtctccaca attgcaatga atgtcaatgt gtcccaagca agttactaa aaaataccac    1080 gaggtccttc agttgagacc aaagaccggt gtcaggggat tgcacaaatc actcaccgac   1140
gtggccctgg agcaccatga ggagtgtgac tgtgtgtgca gagggagcac aggaggatag   1200
ccgcatcacc accagcagct cttgcccaga gctgtgcagt gcagtggctg attctattag   1260
agaacgtatg cgttatctcc atccttaatc tcagttgttt gcttcaagga cctttcatct   1320
tcaggattta cagtgcattc tgaaagagga gacatcaaac agaattagga gttgtgcaac   1380 agctctttg agaggaggcc taaggacag agaaaaggt cttcaatcgt ggaaagaaaa     1440
ttaaatgttg tattaaatag atcaccagct agtttcagag ttaccatgta cgtattccac    1500
tagctgggtt ctgtatttca gttctttcga tacggcttag ggtaatgtca gtacaggaaa    1560
aaaactgtgc aagtgagcac ctgattccgt tgccttgctt aactctaaag ctccatgtcc   1620
tgggcctaaa atcgtataaa atctggattt ttttttttt ttttgctca tattcacata     1680 tgtaaaccag aacattctat gtactacaaa cctggttttt aaaaggaac tatgttgcta    1740 tgaattaaac ttgtgtcgtg ctgataggaa aaaaaaaaaa aaaaaaaaa aaaaaaaaa     1800
``` aaaa                                                                  1804

<210> SEQ ID NO 4
<211> LENGTH: 2253
<212> TYPE: DNA
<213> ORGANISM: Homo sapiens

<400> SEQUENCE: 4
cgctcggaaa gttcagcatg caggaagttt ggggagagct cggcgattag cacagcgacc     60
cgggccagcg cagggcgagc gcaggcggcg agagcgcagg gcggcgcggc gtcggtcccg    120
ggagcagaac ccggcttttt cttggagcga cgctgtctct agtcgctgat cccaaatgca    180
ccggctcatc tttgtctaca ctctaatctg cgcaaacttt tgcagctgtc gggacacttc    240
tgcaaccccg cagagcgcat ccatcaaagc tttgcgcaac gccaacctca ggcgagatga    300
gagcaatcac ctcacagact tgtaccgaag agatgagacc atccaggtga aggaaacgg     360
ctacgtgcag agtcctagat tcccgaacag ctaccccagg aacctgctcc tgacatggcg    420
gcttcactct caggagaata cacggataca gctagtgttt gacaatcagt ttggattaga    480
ggaagcagaa aatgatatct gtaggtatga ttttgtggaa gttgaagata tatccgaaac    540
cagtaccatt attagaggac gatggtgtgg acacaaggaa gttcctccaa ggataaaatc    600
aagaacgaac caaattaaaa tcacattcaa gtccgatgac tactttgtgg ctaaacctgg    660
attcaagatt tattattctt tgctggaaga tttccaaccc gcagcagctt cagagaccaa    720
ctgggaatct gtcacaagct ctatttcagg ggtatcctat aactctccat cagtaacgga    780
tcccactctg attgcggatg ctctggacaa aaaaattgca gaatttgata cagtggaaga    840
tctgctcaag tacttcaatc cagagtcatg gcaagaagat cttgagaata tgtatctgga    900
cacccctcgg tatcgaggca ggtcatacca tgaccggaag tcaaaagttg acctggatag    960
gctcaatgat gatgccaagc gttacagttg cactcccagg aattactcgg tcaatataag   1020
agaagagctg aagttggcca atgtggtctt ctttccacgt tgcctcctcg tgcagcgctg   1080
tggaggaaat tgtggctgtg gaactgtcaa ctggaggtcc tgcacatgca attcagggaa   1140
aaccgtgaaa agtatcatg aggtattaca gtttgagcct ggccacatca agaggagggg   1200
tagagctaag accatggctc tagttgacat ccagttggat caccatgaac gatgcgattg   1260
tatctgcagc tcaagaccac ctcgataaga gaatgtgcac atccttacat taagcctgaa   1320
agaacctta gtttaaggag ggtgagataa gagacccttt tcctaccagc aaccaaactt    1380
actactagcc tgcaatgcaa tgaacacaag tggttgctga gtctcagcct tgctttgtta   1440
atgccatggc aagtagaaag gtatatcatc aacttctata cctaagaata taggattgca   1500
tttaataata gtgtttgagg ttatatatgc acaaacacac acagaaatat attcatgtct   1560
atgtgtatat agatcaaatg ttttttttgg tatatataac caggtacacc agagcttaca   1620
tatgtttgag ttagactctt aaaatccttt gccaaaataa gggatggtca atatatgaa    1680
acatgtcttt agaaaattta ggagataaat ttatttttaa attttgaaac acaaaacaat   1740
tttgaatctt gctctcttaa agaaagcatc ttgtatatta aaaatcaaaa gatgaggctt   1800
tcttacatat acatcttagt tgattattaa aaaggaaaa aggtttccag agaaaaggcc    1860
aatacctaag cattttttcc atgagaagca ctgcatactt acctatgtgg actgtaataa   1920
cctgtctcca aaaccatgcc ataataatat aagtgcttta gaaattaaat cattgtgttt   1980
tttatgcatt ttgctgaggc atccttattc atttaacacc tatctcaaaa acttacttag   2040
aaggtttttt attatagtcc tacaaaagac aatgtataag ctgtaacaga attttgaatt   2100

```
gtttttcttt gcaaaacccc tccacaaaag caaatcctttt caagaatggc atgggcattc    2160
tgtatgaacc tttccagatg gtgttcagtg aaagatgtgg gtagttgaga acttaaaaag    2220
tgaacattga aacatcgacg taactggaaa ccg                                 2253
```

<210> SEQ ID NO 5
<211> LENGTH: 211
<212> TYPE: PRT
<213> ORGANISM: Homo sapiens

<400> SEQUENCE: 5

```
Met Arg Thr Leu Ala Cys Leu Leu Leu Gly Cys Gly Tyr Leu Ala
 1               5                  10                  15

His Val Leu Ala Glu Glu Ala Glu Ile Pro Arg Glu Val Ile Glu Arg
                20                  25                  30

Leu Ala Arg Ser Gln Ile His Ser Ile Arg Asp Leu Gln Arg Leu Leu
            35                  40                  45

Glu Ile Asp Ser Val Gly Ser Glu Asp Ser Leu Asp Thr Ser Leu Arg
        50                  55                  60

Ala His Gly Val His Ala Thr Lys His Val Pro Glu Lys Arg Pro Leu
    65                  70                  75                  80

Pro Ile Arg Arg Lys Arg Ser Ile Glu Glu Ala Val Pro Ala Val Cys
                85                  90                  95

Lys Thr Arg Thr Val Ile Tyr Glu Ile Pro Arg Ser Gln Val Asp Pro
               100                 105                 110

Thr Ser Ala Asn Phe Leu Ile Trp Pro Pro Cys Val Glu Val Lys Arg
           115                 120                 125

Cys Thr Gly Cys Cys Asn Thr Ser Ser Val Lys Cys Gln Pro Ser Arg
       130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
            180                 185                 190

Thr Gly Arg Pro Arg Glu Ser Gly Lys Lys Arg Lys Arg Lys Arg Leu
        195                 200                 205

Lys Pro Thr
    210
```

<210> SEQ ID NO 6
<211> LENGTH: 241
<212> TYPE: PRT
<213> ORGANISM: Homo sapiens

<400> SEQUENCE: 6

```
Met Asn Arg Cys Trp Ala Leu Phe Leu Ser Leu Cys Cys Tyr Leu Arg
 1               5                  10                  15

Leu Val Ser Ala Glu Gly Asp Pro Ile Pro Glu Glu Leu Tyr Glu Met
                20                  25                  30

Leu Ser Asp His Ser Ile Arg Ser Phe Asp Asp Leu Gln Arg Leu Leu
            35                  40                  45

His Gly Asp Pro Gly Glu Glu Asp Gly Ala Glu Leu Asp Leu Asn Met
        50                  55                  60

Thr Arg Ser His Ser Gly Gly Glu Leu Glu Ser Leu Ala Arg Gly Arg
    65                  70                  75                  80

Arg Ser Leu Gly Ser Leu Thr Ile Ala Glu Pro Ala Met Ile Ala Glu
```

```
              85                  90                  95
Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
            115                 120                 125

Arg Cys Ser Gly Cys Cys Asn Asn Arg Asn Val Gln Cys Arg Pro Thr
        130                 135                 140

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Val Ala Ala Ala Arg Pro Val Thr Arg Ser
                180                 185                 190

Pro Gly Gly Ser Gln Glu Gln Arg Ala Lys Thr Pro Gln Thr Arg Val
            195                 200                 205

Thr Ile Arg Thr Val Arg Val Arg Pro Pro Lys Gly Lys His Arg
            210                 215                 220

Lys Phe Lys His Thr His Asp Lys Thr Ala Leu Lys Glu Thr Leu Gly
225                 230                 235                 240

Ala

<210> SEQ ID NO 7
<211> LENGTH: 345
<212> TYPE: PRT
<213> ORGANISM: Homo sapiens

<400> SEQUENCE: 7

Met Ser Leu Phe Gly Leu Leu Leu Thr Ser Ala Leu Ala Gly Gln
 1               5                  10                  15

Arg Gln Gly Thr Gln Ala Glu Ser Asn Leu Ser Ser Lys Phe Gln Phe
                20                  25                  30

Ser Ser Asn Lys Glu Gln Asn Gly Val Gln Asp Pro Gln His Glu Arg
            35                  40                  45

Ile Ile Thr Val Ser Thr Asn Gly Ser Ile His Ser Pro Arg Phe Pro
    50                  55                  60

His Thr Tyr Pro Arg Asn Thr Val Leu Val Trp Arg Leu Val Ala Val
65                  70                  75                  80

Glu Glu Asn Val Trp Ile Gln Leu Thr Phe Asp Glu Arg Phe Gly Leu
                85                  90                  95

Glu Asp Pro Glu Asp Asp Ile Cys Lys Tyr Asp Phe Val Glu Val Glu
            100                 105                 110

Glu Pro Ser Asp Gly Thr Ile Leu Gly Arg Trp Cys Gly Ser Gly Thr
            115                 120                 125

Val Pro Gly Lys Gln Ile Ser Lys Gly Asn Gln Ile Arg Ile Arg Phe
130                 135                 140

Val Ser Asp Glu Tyr Phe Pro Ser Glu Pro Gly Phe Cys Ile His Tyr
145                 150                 155                 160

Asn Ile Val Met Pro Gln Phe Thr Glu Ala Val Ser Pro Ser Val Leu
                165                 170                 175

Pro Pro Ser Ala Leu Pro Leu Asp Leu Leu Asn Asn Ala Ile Thr Ala
            180                 185                 190

Phe Ser Thr Leu Glu Asp Leu Ile Arg Tyr Leu Glu Pro Glu Arg Trp
            195                 200                 205

Gln Leu Asp Leu Glu Asp Leu Tyr Arg Pro Thr Trp Gln Leu Leu Gly
210                 215                 220
```

```
Lys Ala Phe Val Phe Gly Arg Lys Ser Arg Val Val Asp Leu Asn Leu
225                 230                 235                 240

Leu Thr Glu Glu Val Arg Leu Tyr Ser Cys Thr Pro Arg Asn Phe Ser
            245                 250                 255

Val Ser Ile Arg Glu Glu Leu Lys Arg Thr Asp Thr Ile Phe Trp Pro
        260                 265                 270

Gly Cys Leu Leu Val Lys Arg Cys Gly Gly Asn Cys Ala Cys Cys Leu
            275                 280                 285

His Asn Cys Asn Glu Cys Gln Cys Val Pro Ser Lys Val Thr Lys Lys
        290                 295                 300

Tyr His Glu Val Leu Gln Leu Arg Pro Lys Thr Gly Val Arg Gly Leu
305                 310                 315                 320

His Lys Ser Leu Thr Asp Val Ala Leu Glu His His Glu Glu Cys Asp
                325                 330                 335

Cys Val Cys Arg Gly Ser Thr Gly Gly
            340                 345

<210> SEQ ID NO 8
<211> LENGTH: 370
<212> TYPE: PRT
<213> ORGANISM: Homo sapiens

<400> SEQUENCE: 8

Met His Arg Leu Ile Phe Val Tyr Thr Leu Ile Cys Ala Asn Phe Cys
1               5                   10                  15

Ser Cys Arg Asp Thr Ser Ala Thr Pro Gln Ser Ala Ser Ile Lys Ala
            20                  25                  30

Leu Arg Asn Ala Asn Leu Arg Arg Asp Glu Ser Asn His Leu Thr Asp
        35                  40                  45

Leu Tyr Arg Arg Asp Glu Thr Ile Gln Val Lys Gly Asn Gly Tyr Val
    50                  55                  60

Gln Ser Pro Arg Phe Pro Asn Ser Tyr Pro Arg Asn Leu Leu Leu Thr
65                  70                  75                  80

Trp Arg Leu His Ser Gln Glu Asn Thr Arg Ile Gln Leu Val Phe Asp
                85                  90                  95

Asn Gln Phe Gly Leu Glu Glu Ala Glu Asn Asp Ile Cys Arg Tyr Asp
            100                 105                 110

Phe Val Glu Val Glu Asp Ile Ser Glu Thr Ser Thr Ile Ile Arg Gly
        115                 120                 125

Arg Trp Cys Gly His Lys Glu Val Pro Pro Arg Ile Lys Ser Arg Thr
    130                 135                 140

Asn Gln Ile Lys Ile Thr Phe Lys Ser Asp Asp Tyr Phe Val Ala Lys
145                 150                 155                 160

Pro Gly Phe Lys Ile Tyr Tyr Ser Leu Leu Glu Asp Phe Gln Pro Ala
                165                 170                 175

Ala Ala Ser Glu Thr Asn Trp Glu Ser Val Thr Ser Ser Ile Ser Gly
            180                 185                 190

Val Ser Tyr Asn Ser Pro Ser Val Thr Asp Pro Thr Leu Ile Ala Asp
        195                 200                 205

Ala Leu Asp Lys Lys Ile Ala Glu Phe Asp Thr Val Glu Asp Leu Leu
    210                 215                 220

Lys Tyr Phe Asn Pro Glu Ser Trp Gln Glu Asp Leu Glu Asn Met Tyr
225                 230                 235                 240

Leu Asp Thr Pro Arg Tyr Arg Gly Arg Ser Tyr His Asp Arg Lys Ser
                245                 250                 255
```

-continued

```
Lys Val Asp Leu Asp Arg Leu Asn Asp Ala Lys Arg Tyr Ser Cys
            260                 265                 270

Thr Pro Arg Asn Tyr Ser Val Asn Ile Arg Glu Glu Leu Lys Leu Ala
        275                 280                 285

Asn Val Val Phe Phe Pro Arg Cys Leu Leu Val Gln Arg Cys Gly Gly
    290                 295                 300

Asn Cys Gly Cys Gly Thr Val Asn Trp Arg Ser Cys Thr Cys Asn Ser
305                 310                 315                 320

Gly Lys Thr Val Lys Lys Tyr His Glu Val Leu Gln Phe Glu Pro Gly
                325                 330                 335

His Ile Lys Arg Arg Gly Arg Ala Lys Thr Met Ala Leu Val Asp Ile
            340                 345                 350

Gln Leu Asp His His Glu Arg Cys Asp Cys Ile Cys Ser Ser Arg Pro
        355                 360                 365

Pro Arg
    370

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 9
aaccgtgtat aagtcagggg aaacg                                   25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 10
ccgcacctct acaacaaaat gtttg                                   25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 11
aaccgtgtat aagtcagggg aaacg                                   25

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 12
tggccactgt cttcttcctt agca                                    24

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: primer
```

-continued

```
<400> SEQUENCE: 13
gtctctgtga acgcagtgca gactg                                          25

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 14
gcaaattgta gtgtgcccac ctct                                           24

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 15
gtctctgtga acgcagtgca gactg                                          25

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 16
aggcctcgaa cactacctgc agtg                                           24

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 17
ttgggtgcat tggagccttg                                                20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 18
tggccttggt gaggtttgat c                                              21

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 19
ttgggtgcat tggagccttg                                                20

<210> SEQ ID NO 20
<211> LENGTH: 20
```

```
<212> TYPE: DNA
<213> ORGANISM: Artificial Sequence
<220> FEATURE:
<223> OTHER INFORMATION: Description of Artificial Sequence: primer

<400> SEQUENCE: 20
tgagcaaggc ccacagggat                                              20

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 21
agatgtccaa ataagcacac cacgc                                        25

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 22
tttcaagcac ctgctgtttt cga                                          23

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 23
agatgtccaa ataagcacac cacgc                                        25

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 24
ccacgagtca aatagcgagc agatt                                        25

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 25
catccagctg ttgcccagga                                              20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 26
ttcacgggca gcttcaccag                                              20
```

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 27
atgatgtggt tctgagtccg tctca                                              25

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 28
gggggtgggt aaccaaggta ctt                                                23

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 29
atgatgtggt tctgagtccg tctca                                              25

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 30
catgccccgc tttaattgtg tg                                                 22

<210> SEQ ID NO 31
<211> LENGTH: 576
<212> TYPE: DNA
<213> ORGANISM: Homo sapiens

<400> SEQUENCE: 31
atgaactttc tgctgtcttg ggtgcattgg agccttgcct tgctgctcta cctccaccat        60
gccaagtggt cccaggctgc acccatggca gaaggaggag ggcagaatca tcacgaagtg       120
gtgaagttca tggatgtcta tcagcgcagc tactgccatc caatcgagac cctggtggac       180
atcttccagg agtaccctga tgagatcgag tacatcttca gccatcctg tgtgccctg         240 atgcgatgcg ggggctgctg caatgacgag ggcctggagt gtgtgcccac tgaggagtcc       300
aacatcacca tgcagattat gcggatcaaa cctcaccaag gccagcacat aggagagatg       360
agcttcctac agcacaacaa atgtgaatgc agaccaaaga agatagagc aagacaagaa        420 aatccctgtg ggccttgctc agagcggaga aagcatttgt ttgtacaaga tccgcagacg       480
tgtaaatgtt cctgcaaaaa cacagactcg cgttgcaagg cgaggcagct tgagttaaac      540
gaacgtactt gcagatgtga caagccgagg cggtga                                 576

<210> SEQ ID NO 32
<211> LENGTH: 191

```
<212> TYPE: PRT
<213> ORGANISM: Homo sapiens

<400> SEQUENCE: 32

Met Asn Phe Leu Leu Ser Trp Val His Trp Ser Leu Ala Leu Leu Leu
 1               5                  10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190
```